(12) United States Patent
Fields et al.

(10) Patent No.: US 12,430,120 B2
(45) Date of Patent: Sep. 30, 2025

(54) AUTONOMOUS VEHICLE CONTROL ASSESSMENT AND SELECTION

(71) Applicant: State Farm Mutual Automobile Insurance Company, Bloomington, IL (US)

(72) Inventors: Brian Mark Fields, Normal, IL (US); Chien Che Huang, Normal, IL (US); Mohamed A. Wazeer, Normal, IL (US); Shawn C. Bennett, Le Roy, IL (US); Steven C. Cielocha, Bloomington, IL (US); Ronny S. Bryant, Bloomington, IL (US); Stephen Kohaus, Bloomington, IL (US); Terry Quakenbush, Normal, IL (US); Richard A. Novak, Bloomington, IL (US); Aaron Scott Chan, Lisle, IL (US); Craig M. Main, Hagerstown, MD (US); Weixin Wu, Aurora, IL (US); Torri Wollenschlager, Bloomington, IL (US); Carol Marie Csanda, Normal, IL (US); Stacey Gorsuch, Bloomington, IL (US); Todd Binion, Bloomington, IL (US)

(73) Assignee: State Farm Mutual Automobile Insurance Company, Bloomington, IL (US)

( * ) Notice: Subject to any disclaimer, the term of this patent is extended or adjusted under 35 U.S.C. 154(b) by 0 days.

(21) Appl. No.: 18/627,744

(22) Filed: Apr. 5, 2024

(65) Prior Publication Data
US 2024/0256260 A1 Aug. 1, 2024

Related U.S. Application Data

(63) Continuation of application No. 17/963,421, filed on Oct. 11, 2022, now Pat. No. 11,954,482, which is a
(Continued)

(51) Int. Cl.
*B60W 50/04* (2006.01)
*A61B 5/00* (2006.01)
(Continued)

(52) U.S. Cl.
CPC ............ *G06F 8/65* (2013.01); *A61B 5/02028* (2013.01); *A61B 5/4064* (2013.01);
(Continued)

(58) Field of Classification Search
CPC ..... G06F 8/65; A61B 5/02028; A61B 5/4064; A61B 5/4094; A61B 5/6893;
(Continued)

(56) References Cited

U.S. PATENT DOCUMENTS 8,665,118 B1 3/2014 Woodard et al.
8,698,639 B2 4/2014 Fung et al.
(Continued)

FOREIGN PATENT DOCUMENTS

EP 3239686 11/2017
EP 3578433 A1 4/2019
(Continued)

*Primary Examiner* — Ashley L Redhead, Jr.
(74) *Attorney, Agent, or Firm* — Lee & Hayes, P.C.

(57) ABSTRACT

According to certain aspects, a computer-implemented method for operating an autonomous or semi-autonomous vehicle may be provided. With the customer's permission, an identity of a vehicle operator may be identified and a vehicle operator profile may be retrieved. Operating data regarding autonomous operation features operating the vehicle may be received from vehicle-mounted sensors. When a request to disable an autonomous feature is received, a risk level for the autonomous feature is determined and compared with a driver behavior setting for the autonomous feature stored in the vehicle operator profile. Based upon the risk level comparison, the autonomous vehicle retains control of vehicle or the autonomous feature
(Continued)

is disengaged depending upon which is the safer driver—the autonomous vehicle or the vehicle human occupant. As a result, unsafe disengagement of self-driving functionality for autonomous vehicles may be alleviated. Insurance discounts may be provided for autonomous vehicles having this safety functionality.

20 Claims, 14 Drawing Sheets

Related U.S. Application Data continuation of application No. 16/750,038, filed on Jan. 23, 2020, now Pat. No. 11,500,377, which is a continuation of application No. 16/509,605, filed on Jul. 12, 2019, now Pat. No. 10,824,144, which is a continuation of application No. 14/934,388, filed on Nov. 6, 2015, now Pat. No. 10,416,670.

(60) Provisional application No. 62/103,836, filed on Jan. 15, 2015, provisional application No. 62/103,838, filed on Jan. 15, 2015, provisional application No. 62/103,840, filed on Jan. 15, 2015, provisional application No. 62/103,855, filed on Jan. 15, 2015, provisional application No. 62/103,831, filed on Jan. 15, 2015, provisional application No. 62/103,856, filed on Jan. 15, 2015, provisional application No. 62/103,891, filed on Jan. 15, 2015, provisional application No. 62/103,893, filed on Jan. 15, 2015, provisional application No. 62/103,895, filed on Jan. 15, 2015, provisional application No. 62/103,907, filed on Jan. 15, 2015, provisional application No. 62/103,911, filed on Jan. 15, 2015, provisional application No. 62/103,914, filed on Jan. 15, 2015, provisional application No. 62/079,533, filed on Nov. 13, 2014.

(51) Int. Cl.

| | | |
|---|---|---|
| *A61B 5/02* | (2006.01) | |
| *B60K 35/00* | (2006.01) | |
| *B60W 10/04* | (2006.01) | |
| *B60W 30/06* | (2006.01) | |
| *B60W 30/09* | (2012.01) | |
| *B60W 30/095* | (2012.01) | |
| *B60W 40/02* | (2006.01) | |
| *B60W 40/08* | (2012.01) | |
| *B60W 40/09* | (2012.01) | |
| *B60W 50/02* | (2012.01) | |
| *B60W 50/08* | (2020.01) | |
| *B60W 50/12* | (2012.01) | |
| *B60W 50/14* | (2020.01) | |
| *B60W 60/00* | (2020.01) | |
| *B62D 15/02* | (2006.01) | |
| *G01C 21/34* | (2006.01) | |
| *G05D 1/00* | (2006.01) | |
| *G05D 1/248* | (2024.01) | |
| *G05D 1/617* | (2024.01) | |
| *G06F 8/65* | (2018.01) | |
| *G06Q 30/0201* | (2023.01) | |
| *G06Q 30/0207* | (2023.01) | |
| *G06Q 30/0217* | (2023.01) | |
| *G06Q 40/08* | (2012.01) | |
| *G07C 5/02* | (2006.01) | |
| *G07C 5/08* | (2006.01) | |
| *G08B 25/10* | (2006.01) | |
| *G08G 1/09* | (2006.01) | |
| *G08G 1/0962* | (2006.01) | |
| *G08G 1/14* | (2006.01) | |
| *B60W 50/00* | (2006.01) | |

(52) U.S. Cl.
CPC .......... *A61B 5/4094* (2013.01); *A61B 5/6893* (2013.01); *A61B 5/7282* (2013.01); *B60K 35/00* (2013.01); *B60W 10/04* (2013.01); *B60W 30/06* (2013.01); *B60W 30/09* (2013.01); *B60W 30/0956* (2013.01); *B60W 40/02* (2013.01); *B60W 40/08* (2013.01); *B60W 40/09* (2013.01); *B60W 50/02* (2013.01); *B60W 50/0205* (2013.01); *B60W 50/045* (2013.01); *B60W 50/082* (2013.01); *B60W 50/12* (2013.01); *B60W 50/14* (2013.01); *B60W 60/0053* (2020.02); *B60W 60/0059* (2020.02); *B60W 60/007* (2020.02); *B62D 15/0285* (2013.01); *G01C 21/3407* (2013.01); *G05D 1/0055* (2013.01); *G05D 1/0214* (2013.01); *G05D 1/0278* (2013.01); *G05D 1/248* (2024.01); *G05D 1/617* (2024.01); *G06Q 30/0206* (2013.01); *G06Q 30/0207* (2013.01); *G06Q 30/0217* (2013.01); *G06Q 40/08* (2013.01); *G07C 5/02* (2013.01); *G07C 5/0808* (2013.01); *G08B 25/10* (2013.01); *G08G 1/091* (2013.01); *G08G 1/0962* (2013.01); *G08G 1/14* (2013.01); *B60W 2040/0809* (2013.01); *B60W 2040/0818* (2013.01); *B60W 2050/0071* (2013.01); *B60W 2050/0073* (2013.01); *B60W 2050/0075* (2013.01); *B60W 2050/0215* (2013.01); *B60W 2050/046* (2013.01); *B60W 2050/143* (2013.01); *B60W 2420/403* (2013.01); *B60W 2540/043* (2020.02); *B60W 2540/22* (2013.01); *B60W 2540/221* (2020.02); *B60W 2540/26* (2013.01); *B60W 2556/45* (2020.02); *B60W 2756/10* (2020.02); *B60W 2900/00* (2013.01)

(58) Field of Classification Search
CPC ...... A61B 5/7282; B60K 35/00; B60K 35/80; B60K 35/85; B60W 10/04; B60W 30/06; B60W 30/09; B60W 30/0956; B60W 40/02; B60W 40/08; B60W 40/09; B60W 50/02; B60W 50/0205; B60W 50/045; B60W 50/082; B60W 50/12; B60W 50/14; B60W 2540/221; B60W 2540/26; B60W 2556/45; B60W 2756/10; B60W 2900/00; B60W 60/0053; B60W 60/0059; B60W 60/007; B60W 2040/0809; B60W 2040/0818; B60W 2050/0071; B60W 2050/0073; B60W 2050/0075; B60W 2050/0215; B60W 2050/046; B60W 2050/143; B60W 2420/403; B60W 2540/043; B60W 2540/22; B62D 15/0285; G01C 21/3407; G05D 1/0055; G05D 1/0214; G05D 1/0278; G05D 1/248; G05D 1/617; G06Q 30/0206; G06Q 30/0207; G06Q 30/0217; G06Q 40/08; G07C 5/02; G07C 5/0808; G08B 25/10; G08G 1/091; G08G 1/0962; G08G 1/14
See application file for complete search history.

(56) References Cited

U.S. PATENT DOCUMENTS

| | | |
|---|---|---|
| 8,818,608 B2 | 8/2014 | Cullinane et al. |
| 8,874,301 B1 | 10/2014 | Rao et al. |
| 9,063,543 B2 | 6/2015 | An et al. |
| 9,075,413 B2 | 7/2015 | Cullinane et al. |
| 9,098,080 B2 | 8/2015 | Norris et al. |
| 9,235,211 B2 | 1/2016 | Davidsson et al. |
| 9,342,074 B2 | 5/2016 | Dolgov et al. |
| 9,352,752 B2 | 5/2016 | Cullinane et al. |
| 9,390,452 B1 | 7/2016 | Biemer et al. |
| 9,406,177 B2 | 8/2016 | Attard et al. |
| 9,511,779 B2 | 12/2016 | Cullinane et al. |
| 9,594,373 B2 | 3/2017 | Solyom et al. |
| 9,830,748 B2 | 11/2017 | Rosenbaum |
| 9,990,782 B2 | 6/2018 | Rosenbaum |
| 10,269,190 B2 | 4/2019 | Rosenbaum |
| 10,467,824 B2 | 11/2019 | Rosenbaum |
| 11,040,726 B2 | 6/2021 | Tao et al. |
| 11,227,452 B2 | 1/2022 | Rosenbaum |
| 11,285,968 B2 * | 3/2022 | Nguyen ................. G05D 1/0044 |
| 11,407,410 B2 | 8/2022 | Rosenbaum |
| 11,524,707 B2 | 12/2022 | Rosenbaum |
| 11,594,083 B1 | 2/2023 | Rosenbaum |
| 11,685,402 B2 * | 6/2023 | Lee .................. B60W 50/0205 701/27 |
| 2011/0106370 A1 | 5/2011 | Duddle et al. |
| 2011/0241862 A1 | 10/2011 | Debouk et al. |
| 2013/0131907 A1 | 5/2013 | Green et al. |
| 2013/0164714 A1 | 6/2013 | Hunt et al. |
| 2013/0231824 A1 | 9/2013 | Wilson et al. |
| 2013/0265174 A1 | 10/2013 | Scofield et al. |
| 2013/0268187 A1 | 10/2013 | Scofield et al. |
| 2013/0304513 A1 | 11/2013 | Hyde et al. |
| 2014/0088814 A1 * | 3/2014 | You ................. B60W 60/0054 701/23 |
| 2014/0148988 A1 | 5/2014 | Lathrop et al. |
| 2014/0156133 A1 | 6/2014 | Cullinane et al. |
| 2014/0156134 A1 | 6/2014 | Cullinane et al. |
| 2014/0244096 A1 | 8/2014 | An et al. |
| 2014/0303827 A1 | 10/2014 | Dolgov et al. |
| 2014/0330478 A1 | 11/2014 | Cullinane et al. |
| 2014/0336935 A1 * | 11/2014 | Zhu .................. G01N 21/4738 702/3 |
| 2015/0070160 A1 | 3/2015 | Davidsson et al. |
| 2015/0170287 A1 | 6/2015 | Tirone et al. |
| 2015/0187015 A1 | 7/2015 | Adams et al. |
| 2015/0187019 A1 | 7/2015 | Fernandes et al. |
| 2015/0253772 A1 | 9/2015 | Solyom et al. |
| 2015/0266488 A1 | 9/2015 | Solyom et al. |
| 2015/0284009 A1 | 10/2015 | Cullinane et al. |
| 2016/0042650 A1 | 2/2016 | Stenneth |
| 2016/0068103 A1 | 3/2016 | McNew et al. |
| 2016/0200326 A1 | 7/2016 | Cullinane et al. |
| 2016/0272219 A1 | 9/2016 | Ketfi-Cherif et al. |
| 2017/0023945 A1 | 1/2017 | Cavalcanti et al. |
| 2017/0176641 A1 | 6/2017 | Zhu et al. |
| 2017/0329346 A1 | 11/2017 | Latotzki |
| 2018/0014182 A1 * | 1/2018 | Jaegal .................. B60K 35/215 |
| 2018/0194343 A1 | 7/2018 | Lorenz |
| 2018/0233033 A1 | 8/2018 | Nordbruch |
| 2019/0128408 A1 * | 5/2019 | Kishi .................. F16H 61/0213 |
| 2020/0001891 A1 * | 1/2020 | Takano ................. B60W 50/00 |
| 2020/0164895 A1 * | 5/2020 | Boss ................. B60W 60/0053 |
| 2020/0209875 A1 * | 7/2020 | Marzani ................. G06V 20/58 |
| 2020/0342760 A1 * | 10/2020 | Vassilovski ............. H04W 4/40 |
| 2021/0094581 A1 * | 4/2021 | Lee .................. B60W 50/0205 |
| 2021/0339773 A1 * | 11/2021 | Lee .................. B60W 60/0059 |
| 2021/0403048 A1 * | 12/2021 | Nguyen ................. B60W 10/30 |
| 2022/0032963 A1 * | 2/2022 | Gäng .................... B60K 35/10 |
| 2022/0092893 A1 | 3/2022 | Rosenbaum |
| 2022/0340148 A1 | 10/2022 | Rosenbaum |
| 2023/0060300 A1 | 3/2023 | Rosenbaum |
| 2023/0331261 A1 * | 10/2023 | Oba .................. B60W 50/082 |
| 2024/0182083 A1 * | 6/2024 | Zhu .................. B60W 50/0205 |
| 2024/0248708 A1 | 7/2024 | Fields et al. |

FOREIGN PATENT DOCUMENTS

| | | |
|---|---|---|
| EP | 3730375 A1 | 4/2020 |
| EP | 3960576 A1 | 3/2022 |
| EP | 4190659 | 6/2023 |
| EP | 4190660 A1 | 6/2023 |

* cited by examiner

AUTONOMOUS VEHICLE CONTROL ASSESSMENT AND SELECTION

CROSS-REFERENCE TO RELATED APPLICATIONS

This application is a continuation of U.S. patent application Ser. No. 17/963,421 (filed Oct. 11, 2022) which is a continuation of, and claims the benefit of, U.S. patent application Ser. No. 16/750,038, filed Jan. 23, 2020, (now U.S. Pat. No. 11,500,377) which is a continuation of, and claims the benefit of, U.S. patent application Ser. No. 16/509,605 (now U.S. Pat. No. 10,824,144), filed Jul. 12, 2019 and entitled "Autonomous Vehicle Control Assessment and Selection," which is a continuation of, and claims the benefit of, U.S. patent application Ser. No. 14/934,388 (now U.S. Pat. No. 10,416,670), filed Nov. 6, 2015 and entitled "Autonomous Vehicle Control Assessment and Selection," which claims the benefit of U.S. Provisional Application No. 62/079,533 (filed Nov. 13, 2014); U.S. Provisional Application No. 62/103,831 (filed Jan. 15, 2015); U.S. Provisional Application No. 62/103,836 (filed Jan. 15, 2015); U.S. Provisional Application No. 62/103,838 (filed Jan. 15, 2015); U.S. Provisional Application No. 62/103,840 (filed Jan. 15, 2015); U.S. Provisional Application No. 62/103,855 (filed Jan. 15, 2015); U.S. Provisional Application No. 62/103,856 (filed Jan. 15, 2015); U.S. Provisional Application No. 62/103,891 (filed Jan. 15, 2015); U.S. Provisional Application No. 62/103,893 (filed Jan. 15, 2015); U.S. Provisional Application No. 62/103,895 (filed Jan. 15, 2015); U.S. Provisional Application No. 62/103,907 (filed Jan. 15, 2015); U.S. Provisional Application No. 62/103,911 (filed Jan. 15, 2015); and U.S. Provisional Application No. 62/103,914 (filed Jan. 15, 2015). The entirety of each of the foregoing applications is incorporated by reference herein.

Additionally, the present application is related to U.S. patent application Ser. No. 14/934,326 (filed Nov. 6, 2015); U.S. patent application Ser. No. 14/934,333 (filed Nov. 6, 2015); U.S. patent application Ser. No. 14/931,339 (filed Nov. 6, 2015); U.S. patent application Ser. No. 14/934,343 (filed Nov. 6, 2015); U.S. patent application Ser. No. 14/934,345 (filed Nov. 6, 2015); U.S. patent application Ser. No. 14/934,347 (filed Nov. 6, 2015); U.S. patent application Ser. No. 14/934,352 (filed Nov. 6, 2015); U.S. patent application Ser. No. 14/934,355 (filed Nov. 6, 2015); U.S. patent application Ser. No. 14/934,357 (filed Nov. 6, 2015); U.S. patent application Ser. No. 14/934,361 (filed Nov. 6, 2015); U.S. patent application Ser. No. 14/934,371 (filed Nov. 6, 2015); U.S. patent application Ser. No. 14/934,381 (filed Nov. 6, 2015); U.S. patent application Ser. No. 14/934,385 (filed Nov. 6, 2015); U.S. patent application Ser. No. 14/934,393 (filed Nov. 6, 2015); U.S. patent application Ser. No. 14/934,400 (filed Nov. 6, 2015); and U.S. patent application Ser. No. 14/934,405 (filed Nov. 6, 2015).

FIELD

The present disclosure generally relates to systems and methods for operating, monitoring, assessing, or insuring autonomous or semi-autonomous vehicles.

BACKGROUND

Vehicles are typically operated by a human vehicle operator who controls both steering and motive controls. Operator error, inattention, inexperience, misuse, or distraction leads to many vehicle accidents each year, resulting in injury and damage. Autonomous or semi-autonomous vehicles augment vehicle operators' information or replace vehicle operators' control commands to operate the vehicle in whole or in part with computer systems based upon information from sensors within the vehicle.

Vehicle or automobile insurance exists to provide financial protection against physical damage and/or bodily injury resulting from traffic accidents and against liability that could arise therefrom. Typically, a customer purchases a vehicle insurance policy for a policy rate having a specified term in exchange for payments from the insured customer, the insurer pays for damages to the insured which are caused by covered perils, acts, or events as specified by the language of the insurance policy. The payments from the insured are generally referred to as "premiums," and typically are paid on behalf of the insured over time at periodic intervals. An insurance policy may remain "in-force" while premium payments are made during the term or length of coverage of the policy as indicated in the policy. An insurance policy may "lapse" (or have a status or state of "lapsed"), for example, when premium payments are not being paid or if the insured or the insurer cancels the policy.

Premiums may be typically determined based upon a selected level of insurance coverage, location of vehicle operation, vehicle model, and characteristics or demographics of the vehicle operator. The characteristics of a vehicle operator that affect premiums may include age, years operating vehicles of the same class, prior incidents involving vehicle operation, and losses reported by the vehicle operator to the insurer or a previous insurer. Past and current premium determination methods do not, however, account for use of autonomous vehicle operating features. The present embodiments may inter alia, alleviate this and/or other drawbacks associated with conventional techniques.

BRIEF SUMMARY

The present embodiments may be related to autonomous or semi-autonomous vehicle functionality, including driverless operation, accident avoidance, or collision warning systems. These autonomous vehicle operation features may either assist the vehicle operator to more safely or efficiently operate a vehicle or may take full control of vehicle operation under some or all circumstances. The present embodiments may also facilitate risk assessment and premium determination for vehicle insurance policies covering vehicles with autonomous operation features. For instance, a consumer may opt-in to a rewards program that rewards them, such as in the form of insurance discounts, for affirmatively sharing data related to their vehicles and/or autonomous features with an insurance provider.

In accordance with the described embodiments, the disclosure herein generally addresses systems and methods for determining to transfer operation of an autonomous or semi-autonomous vehicle between autonomous operation features and a vehicle operator. A computer (such as an on-board computer, mobile device, or server communicatively connected to the vehicle) associated with the vehicle may (1) determine an identity of a vehicle operator; (2) receive a vehicle operator profile associated with the vehicle operator; (3) receive operating data regarding one or more autonomous operation features of the autonomous or semi-autonomous vehicle; (4) determine one or more autonomous operation risk levels associated with operation of the autonomous or semi-autonomous vehicle by the one or more autonomous operation features based upon (i) received operating data, and/or (ii) driving behavior settings for the vehicle operator that are pre-determined and/or stored in the vehicle operator profile; (5) determine one or more operator risk levels associated with operation of the autonomous or semi-autonomous vehicle by the vehicle operator based upon the received vehicle operating data and/or vehicle operator profile (such as by comparing the vehicle operating data and/or current environment conditions) with the vehicle operator profile); (6) determine to engage or disengage at least one of the one or more autonomous operation features based upon the determine one or more autonomous operation risk levels and the one or more operator risk levels; and/or (7) present an alert to the vehicle operator regarding engagement or disengagement of the at least one of the one or more autonomous operation features.

Determining to disengage the at least one of the one or more autonomous operation features may include determining that the one or more autonomous operation risk levels associated with operation of the autonomous or semi-autonomous vehicle by the at least one of the one or more autonomous operation features exceed the corresponding one or more operator risk levels associated with the same control functions of the autonomous or semi-autonomous vehicle as the at least one of the one or more autonomous operation features, such that manual operation may be safer than autonomous operation under the conditions. Determining to engage the at least one of the one or more autonomous operation features may include determining that the one or more operator risk levels associated with operation of the autonomous or semi-autonomous vehicle by the vehicle operator exceed the corresponding one or more autonomous operation risk levels at least one of the one or more autonomous operation features associated with the same control functions of the autonomous operation features of the autonomous or semi-autonomous vehicle, such that autonomous operation may be safer than manual operation under the conditions. As a result, the vehicle control system may allow the safer driver-either the autonomous vehicle or human driver/passenger/occupant—to remain or gain control of the vehicle.

The operating data may include data from one or more sensors disposed within the autonomous or semi-autonomous vehicle, which may include data regarding the vehicle environment, such as weather, traffic, and/or construction. In some embodiments, the computer may receive autonomous communication data from one or more external sources, which may also be used to determine whether to disengage at least one of the one or more autonomous operation features.

In some embodiments, the computer may further determine a preparedness level of the vehicle operator to assume control of one or more functions of operating the autonomous or semi-autonomous vehicle controlled by the at least one of the one or more autonomous operation features, which preparedness level may be used to determine whether to disengage at least one of the one or more autonomous operation features. When the preparedness level of the vehicle operator is below a transfer threshold, the computer may cause at least one of the one or more autonomous operation features not to disengage during operation of the autonomous or semi-autonomous vehicle. When the preparedness level is below the transfer threshold and above a minimum threshold, the alert may be presented to the vehicle operator and/or the preparedness level determined again after presentation of the alert. When the preparedness level is below a minimum threshold, the autonomous or semi-autonomous vehicle may discontinue operation. The computer may also cause the autonomous or semi-autonomous vehicle to discontinue operation when the autonomous operation risk levels exceed a critical risk threshold and the preparedness level is below a transfer threshold.

In further embodiments, the computer may adjust one or more costs associated with an insurance policy associated with the vehicle operator. The adjustment may be based upon the determination to disengage the at least one of the one or more autonomous operation features based upon the determined one or more autonomous operation risk levels and/or the one or more operator risk levels. The costs associated with the insurance policy may include one or more of the following: a premium, a discount, a surcharge, a rate level, a cost based upon a distance traveled, a cost based upon a vehicle trip, and/or a cost based upon a duration of vehicle operation.

In each of the embodiments or aspects described above, the methods may be provided in corresponding computer systems including at least one or more processors and a non-transitory program memory coupled to the one or more processors and storing executable instructions. The computer systems may further include or be communicatively connected to one or more sensors, communication components or devices, or other equipment as described herein. In yet another aspect, a tangible, non-transitory computer-readable medium storing instructions corresponding to each of the embodiments or aspects described above may be provided. Each of the methods or executable instructions of the computer systems or computer-readable media may include additional, fewer, or alternate actions, including those discussed elsewhere herein.

BRIEF DESCRIPTION OF THE DRAWINGS

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

The figures described below depict various aspects of the applications, methods, and systems disclosed herein. It should be understood that each figure depicts an embodiment of a particular aspect of the disclosed applications, systems and methods, and that each of the figures is intended to accord with a possible embodiment thereof. Furthermore, wherever possible, the following description refers to the reference numerals included in the following figures, in which features depicted in multiple figures are designated with consistent reference numerals.

DETAILED DESCRIPTION

Figure 1:
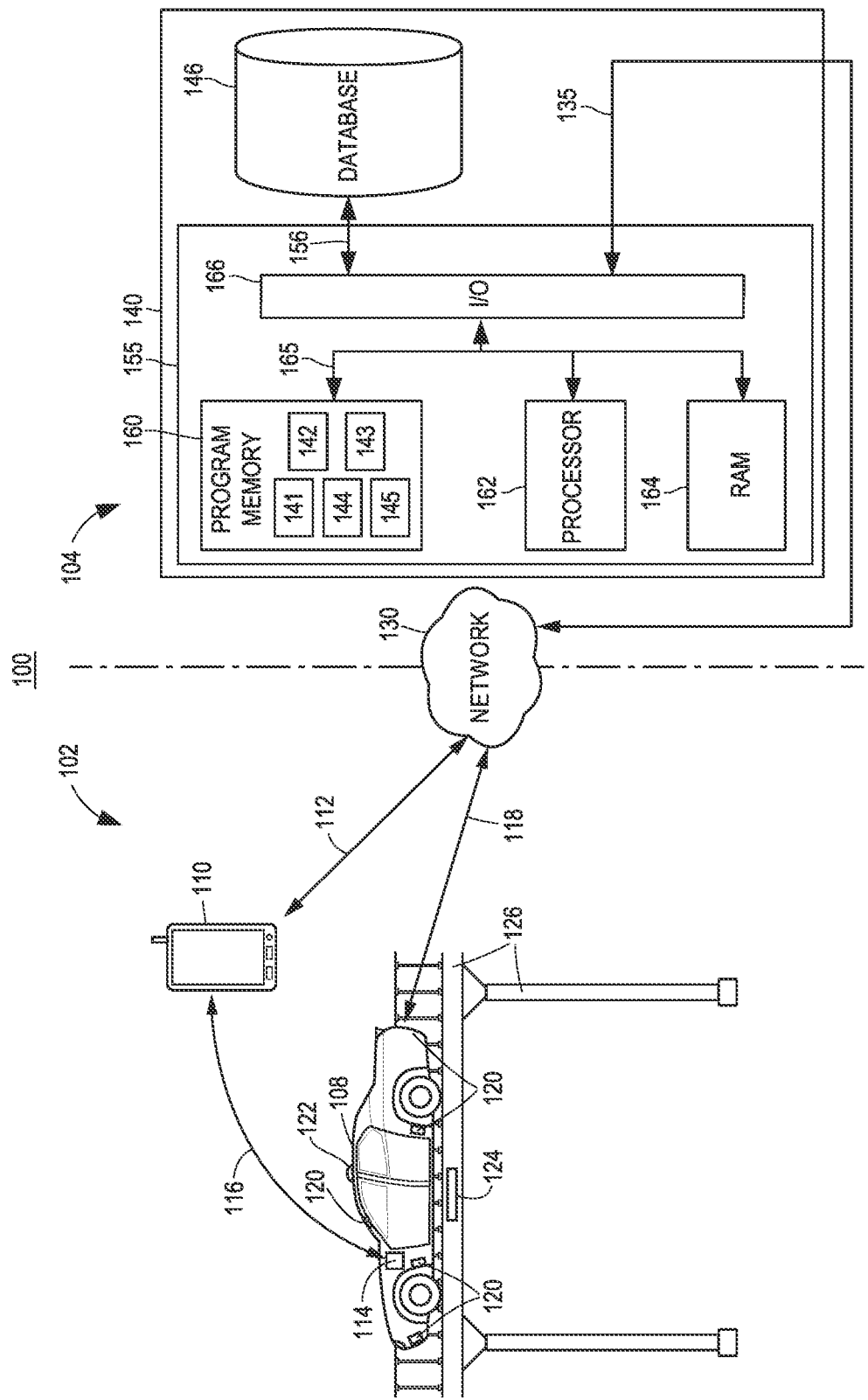
FIG. 1 illustrates a block diagram of an exemplary computer network, a computer server, a mobile device, and an on-board computer for implementing autonomous vehicle operation, monitoring, evaluation, and insurance processes in accordance with the described embodiments.

The systems and methods disclosed herein generally relate to evaluating, monitoring, and managing risks related to the operation of autonomous or semi-autonomous vehicles having autonomous (or semi-autonomous) operation features. The systems and methods further relate to pricing and processing vehicle insurance policies for autonomous or semi-autonomous vehicles. The autonomous operation features may take full control of the vehicle under certain conditions, viz. fully autonomous operation, or the autonomous operation features may assist the vehicle operator in operating the vehicle, viz. partially autonomous operation. Fully autonomous operation features may include systems within the vehicle that pilot the vehicle to a destination with or without a vehicle operator present (e.g., an operating system for a driverless car). Partially autonomous operation features may assist the vehicle operator in limited ways (e.g., automatic braking or collision avoidance systems).

The type and quality of the autonomous operation features may affect the risks related to operating a vehicle, both individually and/or in combination. In addition, configurations and settings of the autonomous operation features may further impact the risks. To account for the effects on such risks, some embodiments evaluate the quality of each autonomous operation feature and/or combination of features. Additional embodiments evaluate the risks associated with the vehicle operator interacting with the autonomous operation features. Further embodiments address the relative risks associated with control of some aspects of vehicle control by the autonomous operation features or by the vehicle operator. Still further embodiments address use of information received or generated by the autonomous operation features to manage risk and/or damage.

Some autonomous operation features may be adapted for use under particular conditions, such as city driving or highway driving. Additionally, the vehicle operator may be able to configure settings relating to the features or may enable or disable the features individually or in groups. For example, the vehicle operator may select a mode of operation for the autonomous or semi-autonomous vehicle, which may adjust settings for one or more autonomous operation features. Therefore, some embodiments monitor use of the autonomous operation features, which may include the settings or levels of feature use during vehicle operation, as well as the selection of features or settings of the autonomous operation features chosen by the vehicle operator.

Information obtained by monitoring feature usage may be used to determine risk levels associated with vehicle operation, either generally or in relation to a vehicle operator. In such situations, total risk may be determined by a weighted combination of the risk levels associated with operation while autonomous operation features are enabled (with relevant settings) and the risk levels associated with operation while autonomous operation features are disabled. For fully autonomous vehicles, settings or configurations relating to vehicle operation may be monitored and used in determining vehicle operating risk.

In addition to use in controlling the vehicle, information regarding the risks associated with vehicle operation with and without the autonomous operation features may then be used to determine risk categories or premiums for a vehicle insurance policy covering a vehicle with autonomous operation features. Risk category or price may be determined based upon factors relating to the evaluated effectiveness of the autonomous vehicle features. The risk or price determination may also include traditional factors, such as location, vehicle type, and level of vehicle use. For fully autonomous vehicles, factors relating to vehicle operators may be excluded entirely. For partially autonomous vehicles, factors relating to vehicle operators may be reduced in proportion to the evaluated effectiveness and monitored usage levels of the autonomous operation features. For vehicles with autonomous communication features that obtain information from external sources (e.g., other vehicles or infrastructure), the risk level and/or price determination may also include an assessment of the availability of external sources of information. Location and/or timing of vehicle use may thus be monitored and/or weighted to determine the risk associated with operation of the vehicle.

Autonomous Automobile Insurance

The present embodiments may relate to assessing and pricing insurance based upon autonomous (or semi-autonomous) functionality of a vehicle, utilization of the autonomous (or semi-autonomous) functionality of the vehicle, and/or operation of the vehicle by a human operator. In some embodiments, the vehicle operator may not control the operations of the vehicle directly, in which case the assessment, rating, and pricing of insurance may exclude consideration of the vehicle operator. A smart vehicle may maneuver itself without human intervention and/or include sensors, processors, computer instructions, and/or other components that may perform or direct certain actions conventionally performed by a human operator.

An analysis of how artificial intelligence facilitates avoiding accidents and/or mitigates the severity of accidents may be used to build a database and/or model of risk assessment. After which, automobile insurance risk and/or premiums (as well as insurance discounts, rewards, and/or points) may be adjusted based upon autonomous or semi-autonomous vehicle functionality, such as by groups of autonomous or semi-autonomous functionality or individual features. In one aspect, an evaluation may be performed on how artificial intelligence, and the usage thereof, impacts automobile accidents and/or automobile insurance claims.

The types of autonomous or semi-autonomous vehicle-related functionality or technology that may be used with the present embodiments to replace human driver actions may include and/or be related to the following types of functionality: (a) fully autonomous (driverless); (b) limited driver control; (c) vehicle-to-vehicle (V2V) wireless communication; (d) vehicle-to-infrastructure (and/or vice versa) wireless communication; (e) automatic or semiautomatic steering; (f) automatic or semi-automatic acceleration; (g) automatic or semiautomatic braking; (h) automatic or semi-automatic blind spot monitoring; (i) automatic or semiautomatic collision warning; (j) adaptive cruise control; (k) automatic or semi-automatic parking/parking assistance; (l) automatic or semi-automatic collision preparation (windows roll up, seat adjusts upright, brakes pre-charge, etc.); (m) driver acuity/alertness monitoring; (n) pedestrian detection; (o) autonomous or semi-autonomous backup systems; (p) road mapping systems; (q) software security and anti-hacking measures; (r) theft prevention/automatic return; (s) automatic or semi-automatic driving without occupants; and/or other functionality. Additionally or alternatively, the autonomous or semi-autonomous functionality or technology may include and/or may be related to: (t) driver alertness or responsive monitoring; (u) pedestrian detection; (v) artificial intelligence and/or back-up systems; (w) navigation or GPS related systems; (x) security and/or anti-hacking measures; and/or (y) theft prevention systems.

The adjustments to automobile insurance rates or premiums based upon the autonomous or semi-autonomous vehicle-related functionality or technology may take into account the impact of such functionality or technology on the likelihood of a vehicle accident or collision occurring. For instance, a processor may analyze historical accident information and/or test data involving vehicles having autonomous or semi-autonomous functionality. Factors that may be analyzed and/or accounted for that are related to insurance risk, accident information, or test data may include (1) point of impact; (2) type of road; (3) time of day; (4) weather conditions; (5) road construction; (6) type/length of trip; (7) vehicle style; (8) level of pedestrian traffic; (9) level of vehicle congestion; (10) atypical situations (such as manual traffic signaling); (11) availability of internet connection for the vehicle; and/or other factors. These types of factors may also be weighted according to historical accident information, predicted accidents, vehicle trends, test data, and/or other considerations.

In one aspect, the benefit of one or more autonomous or semi-autonomous functionalities or capabilities may be determined, weighted, and/or otherwise characterized. For instance, the benefit of certain autonomous or semi-autonomous functionality may be substantially greater in city or congested traffic, as compared to open road or country driving traffic. Additionally or alternatively, certain autonomous or semi-autonomous functionality may only work effectively below a certain speed, e.g., during city driving or driving in congestion. Other autonomous or semi-autonomous functionality may operate more effectively on the highway and away from city traffic, such as cruise control. Further individual autonomous or semi-autonomous functionality may be impacted by weather, such as rain or snow, and/or time of day (day light versus night). As an example, fully automatic or semi-automatic lane detection warnings may be impacted by rain, snow, ice, and/or the amount of sunlight (all of which may impact the imaging or visibility of lane markings painted onto a road surface, and/or road markers or street signs).

Automobile insurance premiums, rates, discounts, rewards, refunds, points, or other costs may be adjusted based upon the percentage of time or vehicle usage that the vehicle is the driver, i.e., the amount of time a specific driver uses each type of autonomous (or even semiautonomous) vehicle functionality. Such premiums, rates, discounts, rewards, refunds, points, or other costs may further be adjusted based upon the extent of use of the autonomous operation features, including settings or modes impacting the operation of the autonomous operation features. Moreover, information regarding the vehicle environment during use (e.g., weather, traffic, time of day, etc.) may be included in insurance adjustment determinations, as may traditional information regarding one or more vehicle operators (and the extent to which each vehicle operator uses the vehicle).

Such usage information for a particular vehicle may be gathered over time and/or via remote wireless communication with the vehicle. One embodiment may involve a processor on the vehicle, such as within a vehicle control system or dashboard, monitoring in real-time the vehicle operator and/or the use of autonomous operation features while the vehicle is operating. Other types of monitoring may be remotely performed, such as via wireless communication between the vehicle and a remote server, or wireless communication between a vehicle-mounted dedicated device (that is configured to gather autonomous or semi-autonomous functionality usage information) and a remote server.

Additionally, in some embodiments, the vehicle may transmit and/or receive communications to or from external sources, such as other vehicles (V2V), infrastructure (e.g., a bridge, traffic light, railroad crossing, toll both, marker, sign, or other equipment along the side of a road or highway), pedestrians, databases, or other information sources external to the vehicle. Such communication may allow the vehicle to obtain information regarding other vehicles, obstacles, road conditions, or environmental conditions that could not be detected by sensors disposed within the vehicle. For example, V2V communication may allow a vehicle to identify other vehicles approaching an intersection even when the direct line between the vehicle and the other vehicles is obscured by buildings. As another example, the V2V wireless communication from a first vehicle to a second vehicle (following the first vehicle) may indicate that the first vehicle is braking, which may include the degree to which the vehicle is braking. response, the second vehicle may automatically or autonomously brake in advance of detecting the deceleration of the first vehicle based upon sensor data.

Insurance premiums, rates, ratings, discounts, rewards, special offers, points, programs, refunds, claims, claim amounts, or other costs associated with an insurance policy may be adjusted for, or may otherwise take into account, the foregoing functionality and/or the other functionality described herein. For instance, insurance policies may be updated based upon installed autonomous operation features, the extent of use of the autonomous operation features, V2V wireless communication, and/or vehicle-to-infrastructure or infrastructure-to vehicle wireless communication. The present embodiments may assess and price insurance risks at least in part based upon autonomous operation features that replace some actions of the vehicle operator in controlling the vehicle, including settings and operating status of the autonomous operation features.

Exemplary Autonomous Vehicle Operation System

FIG. 1 illustrates a block diagram of an exemplary autonomous vehicle insurance system 100 on which the exemplary methods described herein may be implemented. The high-level architecture includes both hardware and software applications, as well as various data communications channels for communicating data between the various hardware and software components. The autonomous vehicle insurance system 100 may be roughly divided into frontend components 102 and back-end components 104. The front-end components 102 may obtain information regarding a vehicle 108 (e.g., a car, truck, motorcycle, etc.) and the surrounding environment. An on-board computer 114 may utilize this information to operate the vehicle 108 according to an autonomous operation feature or to assist the vehicle operator in operating the vehicle 108. To monitor the vehicle 108, the front-end components 102 may include one or more sensors 120 installed within the vehicle 108 that may communicate with the on-board computer 114. The front-end components 102 may further process the sensor data using the onboard computer 114 or a mobile device 110 (e.g., a smart phone, a tablet computer, a special purpose computing device, etc.) to determine when the vehicle is in operation and information regarding the vehicle. In some embodiments of the system 100, the front-end components 102 may communicate with the back-end components 104 via a network 130. Either the on-board computer 114 or the mobile device 110 may communicate with the back-end components 104 via the network 130 to allow the back-end components 104 to record information regarding vehicle usage. The back-end components 104 may use one or more servers 140 to receive data from the front-end components 102, determine use and effectiveness of autonomous operation features, determine risk levels or premium price, and/or facilitate purchase or renewal of an autonomous vehicle insurance policy.

The front-end components 102 may be disposed within or communicatively connected to one or more on-board computers 114, which may be permanently or removably installed in the vehicle 108. The on-board computer 114 may interface with the one or more sensors 120 within the vehicle 108 (e.g., an ignition sensor, an odometer, a system clock, a speedometer, a tachometer, an accelerometer, a gyroscope, a compass, a geolocation unit, a camera, a distance sensor, etc.), which sensors may also be incorporated within or connected to the on-board computer 114. The front-end components 102 may further include a communication component 122 to transmit information to and receive information from external sources, including other vehicles, infrastructure, or the back-end components 104. In some embodiments, the mobile device 110 may supplement the functions performed by the on-board computer 114 described herein by, for example, sending or receiving information to and from the mobile server 140 via the network 130. In other embodiments, the on-board computer 114 may perform all of the functions of the mobile device 110 described herein, in which case no mobile device 110 may be present in the system 100. Either or both of the mobile device 110 or on-board computer 114 may communicate with the network 130 over links 112 and 118, respectively. Additionally, the mobile device 110 and on-board computer 114 may communicate with one another directly over link 116.

The mobile device 110 may be either a general-use personal computer, cellular phone, smart phone, tablet computer, phablet, wearable electronics, PDA (personal digital assistant), smart glasses, smart watches, smart bracelet, pager, computing device configured for wired or wireless RF (radio frequency) communication, a dedicated vehicle use monitoring device, and/or other mobile computing device. Although only one mobile device 110 is illustrated, it should be understood that a plurality of mobile devices 110 may be used in some embodiments. The on-board computer 114 may be a general-use on-board computer capable of performing many functions relating to vehicle operation or a dedicated computer for autonomous vehicle operation. Further, the on-board computer 114 may be installed by the manufacturer of the vehicle 108 or as an aftermarket modification or addition to the vehicle 108. In some embodiments or under certain conditions, the mobile device 110 or on-board computer 114 may function as thin-client devices that outsource some or most of the processing to the server 140.

The sensors 120 may be removably or fixedly installed within the vehicle 108 and may be disposed in various arrangements to provide information to the autonomous operation features. Among the sensors 120 may be included one or more of a GPS (Global Positioning System) unit, other satellite-based navigation unit, a radar unit, a LIDAR (Light Detection and Ranging) unit, an ultrasonic sensor, an infrared sensor, a camera, an accelerometer, a tachometer, and/or a speedometer. Some of the sensors 120 (e.g., radar, LIDAR, or camera units) may actively or passively scan the vehicle environment for obstacles (e.g., other vehicles, buildings, pedestrians, etc.), lane markings, or signs or signals. Other sensors 120 (e.g., GPS, accelerometer, or tachometer units) may provide data for determining the location or movement of the vehicle 108. Other sensors 120 may be directed to the interior or passenger compartment of the vehicle 108, such as cameras, microphones, pressure sensors, thermometers, or similar sensors to monitor the vehicle operator and/or passengers within the vehicle 108. Information generated or received by the sensors 120 may be communicated to the on-board computer 114 or the mobile device 110 for use in autonomous vehicle operation.

In some embodiments, the communication component 122 may receive information from external sources, such as other vehicles or infrastructure. The communication component 122 may also send information regarding the vehicle 108 to external sources. To send and receive information, the communication component 122 may include a transmitter and a receiver designed to operate according to predetermined specifications, such as the dedicated short-range communication (DSRC) channel, wireless telephony, Wi-Fi, or other existing or later-developed communications protocols. The received information may supplement the data received from the sensors 120 to implement the autonomous operation features. For example, the communication component 122 may receive information that an autonomous vehicle ahead of the vehicle 108 is reducing speed, allowing the adjustments in the autonomous operation of the vehicle 108.

In further embodiments, the front-end components may include an infrastructure communication device 124 for monitoring the status of one or more infrastructure components 126. The infrastructure communication device 124 may include or be communicatively connected to one or more sensors (not shown) for detecting information relating to the condition of the infrastructure component 126. The sensors (not shown) may generate data relating to weather conditions, traffic conditions, or operating status of the infrastructure component 126. The infrastructure communication device 124 may be configured to receive the sensor data generated and determine a condition of the infrastructure component 126, such as weather conditions, road integrity, construction, traffic, available parking spaces, etc. The infrastructure communication device 124 may further be configured to communicate information to vehicles 108 via the communication component 122. In some embodiments, the infrastructure communication device 124 may receive information from the vehicles 108, while, in other embodiments, the infrastructure communication device 124 may only transmit information to the vehicles 108.

In addition to receiving information from the sensors 120, the on-board computer 114 may directly or indirectly control the operation of the vehicle 108 according to various autonomous operation features. The autonomous operation features may include software applications or routines implemented by the on-board computer 114 to control the steering, braking, or throttle of the vehicle 108. To facilitate such control, the on-board computer 114 may be communicatively connected to the controls or components of the vehicle 108 by various electrical or electromechanical control components (not shown). In embodiments involving fully autonomous vehicles, the vehicle 108 may be operable only through such control components (not shown). In other embodiments, the control components may be disposed within or supplement other vehicle operator control components (not shown), such as steering wheels, accelerator or brake pedals, or ignition switches.

In some embodiments, the front-end components 102 may communicate with the back-end components 104 via the network 130. The network 130 may be a proprietary network, a secure public internet, a virtual private network or some other type of network, such as dedicated access lines, plain ordinary telephone lines, satellite links, cellular data networks, combinations of these. Where the network 130 comprises the Internet, data communications may take place over the network 130 via an Internet communication protocol.

The back-end components 104 may include one or more servers 140. Each server 140 may include one or more computer processors adapted and configured to execute various software applications and components of the autonomous vehicle insurance system 100, in addition to other software applications. The server 140 may further include a database 146, which may be adapted to store data related to the operation of the vehicle 108 and its autonomous operation features. Such data might include, for example, dates and times of vehicle use, duration of vehicle use, use and settings of autonomous operation features, speed of the vehicle 108, RPM or other tachometer readings of the vehicle 108, lateral and longitudinal acceleration of the vehicle 108, incidents or near collisions of the vehicle 108, communication between the autonomous operation features and external sources, environmental conditions of vehicle operation (e.g., weather, traffic, road condition, etc.), errors or failures of autonomous operation features, or other data relating to use of the vehicle 108 and the autonomous operation features, which may be uploaded to the server 140 via the network 130. The server 140 may access data stored in the database 146 when executing various functions and tasks associated with the evaluating feature effectiveness or assessing risk relating to an autonomous vehicle.

Although the autonomous vehicle insurance system 100 is shown to include one vehicle 108, one mobile device 110, one on-board computer 114, and one server 140, it should be understood that different numbers of vehicles 108, mobile devices 110, on-board computers 114, and/or servers 140 may be utilized. For example, the system 100 may include a plurality of servers 140 and hundreds of mobile devices 110 or on-board computers 114, all of which may be interconnected via the network 130. Furthermore, the database storage or processing performed by the one or more servers 140 may be distributed among a plurality of servers 140 in an arrangement known as "cloud computing." This configuration may provide various advantages, such as enabling near real-time uploads and downloads of information as well as periodic uploads and downloads of information. This may in turn support a thin-client embodiment of the mobile device 110 or on-board computer 114 discussed herein.

The server 140 may have a controller 155 that is operatively connected to the database 146 via a link 156. It should be noted that, while not shown, additional databases may be linked to the controller 155 in a known manner. For example, separate databases may be used for autonomous operation feature information, vehicle insurance policy information, and vehicle use information. The controller 155 may include a program memory 160, a processor 162 (which may be called a microcontroller or a microprocessor), a random-access memory (RAM) 164, and an input/output (I/O) circuit 166, all of which may be interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM 164 and program memories 160 may be implemented as semiconductor memories, magnetically readable memories, or optically readable memories, for example. The controller 155 may also be operatively connected to the network 130 via a link 135.

The server 140 may further include a number of software applications stored in a program memory 160. The various software applications on the server 140 may include an autonomous operation information monitoring application 141 for receiving information regarding the vehicle 108 and its autonomous operation features, a feature evaluation application 142 for determining the effectiveness of autonomous operation features under various conditions, a compatibility evaluation application 143 for determining the effectiveness of combinations of autonomous operation features, a risk assessment application 144 for determining a risk category associated with an insurance policy covering an autonomous vehicle, and an autonomous vehicle insurance policy purchase application 145 for offering and facilitating purchase or renewal of an insurance policy covering an autonomous vehicle. The various software applications may be executed on the same computer processor or on different computer processors.

The various software applications may include various software routines stored in the program memory 160 to implement various modules using the process 162. Additionally, or alternatively, the software applications or routines may interact with various hardware modules that may be installed within or connected to the server 140. Such modules may implement part of all of the various exemplary methods discussed herein or other related embodiments. Such modules may include a vehicle control module for determining and implementing control decisions to operate the vehicle 108, a system status module for determining the operating status of autonomous operation features, a monitoring module for monitoring the operation of the vehicle 108, a remediation module for correcting abnormal operating states of autonomous operation features, an insurance module for determining risks and costs associated with operation of the vehicle 108, an alert module for generating and presenting alerts regarding the vehicle 108 or the vehicle operator, a risk assessment module for determining risks associated with operation of the vehicle 108 by the autonomous operation features or by the vehicle operator, an identification module for identifying or verifying the identity of the vehicle operator, an information module for obtaining information regarding a vehicle operator or vehicle 108, a use cost module for determining costs associated with operation of the vehicle 108, a comparison module for comparing one or more costs associated with owning or operating the vehicle 108, an update module for updating an autonomous operation feature of the vehicle 108, or other modules.

Exemplary Mobile Device or on-Board Computer

Figure 2:
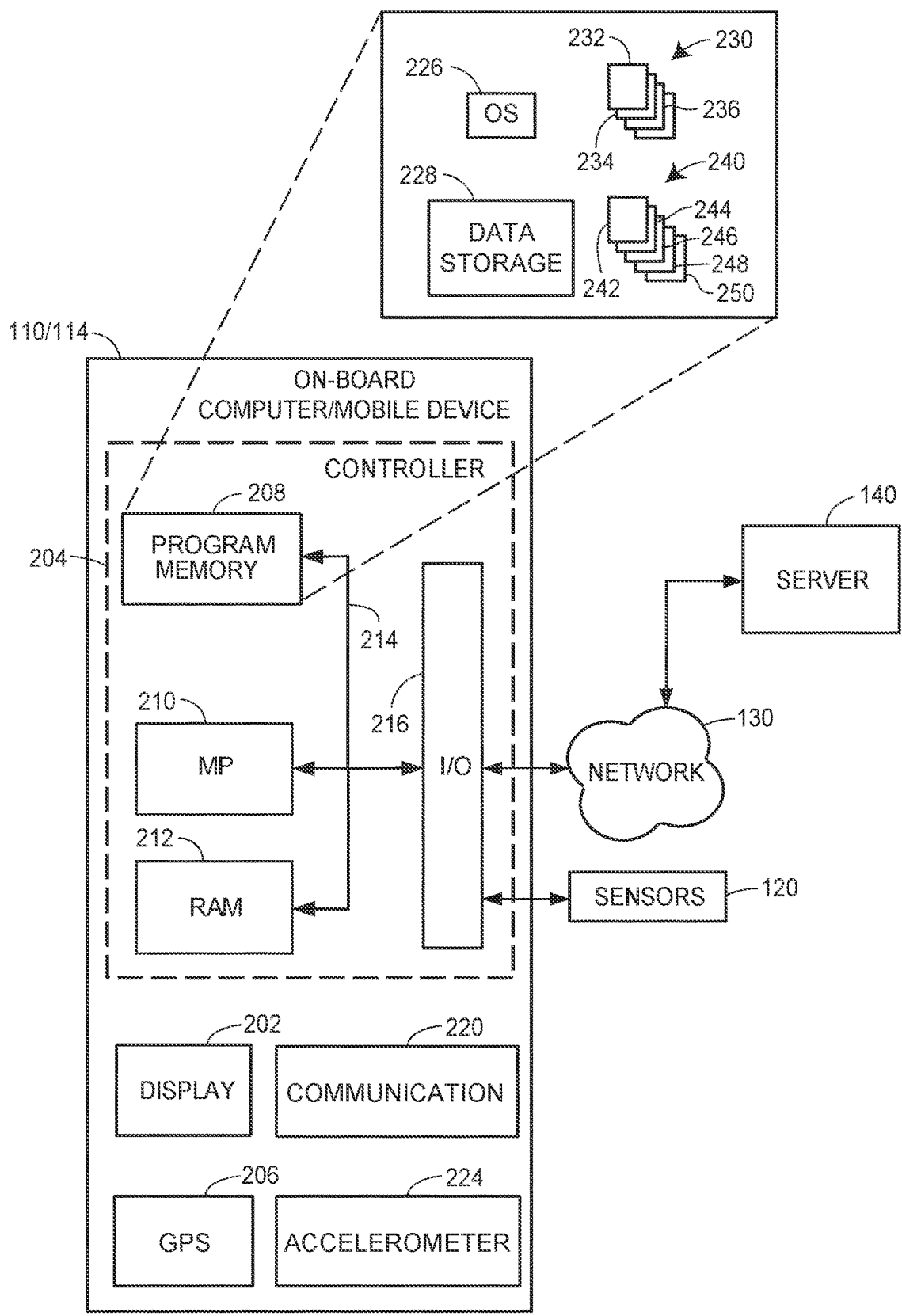
FIG. 2 illustrates a block diagram of an exemplary on-board computer or mobile device.

FIG. 2 illustrates a block diagram of an exemplary mobile device 110 and/or an exemplary on-board computer 114 consistent with the system 100. The mobile device 110 and/or on-board computer 114 may include a display 202, a GPS unit 206, a communication unit 220, an accelerometer 224, one or more additional sensors (not shown), a user-input device (not shown), and/or, like the server 140, a controller 204. In some embodiments, the mobile device 110 and on-board computer 114 may be integrated into a single device, or either may perform the functions of both. The on-board computer 114 (or mobile device 110) may interface with the sensors 120 to receive information regarding the vehicle 108 and its environment, which information may be used by the autonomous operation features to operate the vehicle 108.

Similar to the controller 155, the controller 204 may include a program memory 208, one or more microcontrollers or microprocessors (MP) 210, a RAM 212, and an I/O circuit 216, all of which are interconnected via an address/data bus 214. The program memory 208 may include an operating system 226, a data storage 228, a plurality of software applications 230, and/or a plurality of software routines 240. The operating system 226, for example, may include one of a plurality of general purpose or mobile platforms, such as the Android™, iOS®, or Windows® systems, developed by Google Inc., Apple Inc., and Microsoft Corporation, respectively. Alternatively, the operating system 226 may be a custom operating system designed for autonomous vehicle operation using the on-board computer 114. The data storage 228 may include data such as user profiles and preferences, application data for the plurality of applications 230, routine data for the plurality of routines 240, and other data related to the autonomous operation features. In some embodiments, the controller 204 may also include, or otherwise be communicatively connected to, other data storage mechanisms (e.g., one or more hard disk drives, optical storage drives, solid state storage devices, etc.) that reside within the vehicle 108.

As discussed with reference to the controller 155, it should be appreciated that although FIG. 2 depicts only one microprocessor 210, the controller 204 may include multiple microprocessors 210. Similarly, the memory of the controller 204 may include multiple RAMs 212 and multiple program memories 208. Although FIG. 2 depicts the I/O circuit 216 as a single block, the I/O circuit 216 may include a number of different types of I/O circuits. The controller 204 may implement the RAMs 212 and the program memories 208 as semiconductor memories, magnetically readable memories, or optically readable memories, for example.

The one or more processors 210 may be adapted and configured to execute any of one or more of the plurality of software applications 230 or any one or more of the plurality of software routines 240 residing in the program memory 204, in addition to other software applications. One of the plurality of applications 230 may be an autonomous vehicle operation application 232 that may be implemented as a series of machine-readable instructions for performing the various tasks associated with implementing one or more of the autonomous operation features according to the autonomous vehicle operation method 300. Another of the plurality of applications 230 may be an autonomous communication application 234 that may be implemented as a series of machine-readable instructions for transmitting and receiving autonomous operation information to or from external sources via the communication unit 220. Still another application of the plurality of applications 230 may include an autonomous operation monitoring application 236 that may be implemented as a series of machine-readable instructions for sending information regarding autonomous operation of the vehicle to the server 140 via the network 130.

The plurality of software applications 230 may call various of the plurality of software routines 240 to perform functions relating to autonomous vehicle operation, monitoring, or communication. In some embodiments, the plurality of software routines may further assess risk levels or determine insurance policy costs and adjustments. One of the plurality of software routines 240 may be a configuration routine 242 to receive settings from the vehicle operator to configure the operating parameters of an autonomous operation feature. Another of the plurality of software routines 240 may be a sensor control routine 244 to transmit instructions to a sensor 120 and receive data from the sensor 120. Still another of the plurality of software routines 240 may be an autonomous control routine 246 that performs a type of autonomous control, such as collision avoidance, lane centering, and/or speed control. In some embodiments, the autonomous vehicle operation application 232 may cause a plurality of autonomous control routines 246 to determine control actions required for autonomous vehicle operation. Similarly, one of the plurality of software routines 240 may be a monitoring and reporting routine 248 that monitors and transmits information regarding autonomous vehicle operation to the server 140 via the network 130. Yet another of the plurality of software routines 240 may be an autonomous communication routine 250 for receiving and transmitting information between the vehicle 108 and external sources to improve the effectiveness of the autonomous operation features.

Any of the plurality of software routines 240 may be designed to operate independently of the software applications 230 or in conjunction with the software applications 230 to implement modules associated with the methods discussed herein using the microprocessor 210 of the controller 204. Additionally, or alternatively, the software applications 230 or software routines 240 may interact with various hardware modules that may be installed within or connected to the mobile device 110 or the on-board computer 114. Such modules may implement part of all of the various exemplary methods discussed herein or other related embodiments.

For instance, such modules may include a vehicle control module for determining and implementing control decisions to operate the vehicle 108, a system status module for determining the operating status of autonomous operation features, a monitoring module for monitoring the operation of the vehicle 108, a remediation module for correcting abnormal operating states of autonomous operation features, an insurance module for determining risks and costs associated with operation of the vehicle 108, an alert module for generating and presenting alerts regarding the vehicle 108 or the vehicle operator, a risk assessment module for determining risks associated with operation of the vehicle 108 by the autonomous operation features or by the vehicle operator, an identification module for identifying or verifying the identity of the vehicle operator, an information module for obtaining information regarding a vehicle operator or vehicle 108, a use cost module for determining costs associated with operation of the vehicle 108, a comparison module for comparing one or more costs associated with owning or operating the vehicle 108, an update module for updating an autonomous operation feature of the vehicle 108, and/or other modules.

When implementing the exemplary autonomous vehicle operation method 300, the controller 204 of the on-board computer 114 may implement a vehicle control module by the autonomous vehicle operation application 232 to communicate with the sensors 120 to receive information regarding the vehicle 108 and its environment and process that information for autonomous operation of the vehicle 108. In some embodiments, including external source communication via the communication component 122 or the communication unit 220, the controller 204 may further implement a communication module based upon the autonomous communication application 234 to receive information for external sources, such as other autonomous vehicles, smart infrastructure (e.g., electronically communicating roadways, traffic signals, or parking structures), or other sources of relevant information (e.g., weather, traffic, local amenities). Some external sources of information may be connected to the controller 204 via the network 130, such as the server 140 or internet-connected third-party databases (not shown). Although the autonomous vehicle operation application 232 and the autonomous communication application 234 are shown as two separate applications, it should be understood that the functions of the autonomous operation features may be combined or separated into any number of the software applications 230 or the software routines 240.

In some embodiments, the controller 204 may further implement a monitoring module by the autonomous operation monitoring application 236 to communicate with the server 140 to provide information regarding autonomous vehicle operation. This may include information regarding settings or configurations of autonomous operation features, data from the sensors 120 regarding the vehicle environment, data from the sensors 120 regarding the response of the vehicle 108 to its environment, communications sent or received using the communication component 122 or the communication unit 220, operating status of the autonomous vehicle operation application 232 and the autonomous communication application 234, and/or commands sent from the on-board computer 114 to the control components (not shown) to operate the vehicle 108. The information may be received and stored by the server 140 implementing the autonomous operation information monitoring application 141, and the server 140 may then determine the effectiveness of autonomous operation under various conditions by implementing the feature evaluation application 142 and the compatibility evaluation application 143. The effectiveness of autonomous operation features and the extent of their use may be further used to determine risk associated with operation of the autonomous vehicle by the server 140 implementing a risk assessment module or insurance module associated with the risk assessment application 144.

In addition to connections to the sensors 120, the mobile device 110 or the on-board computer 114 may include additional sensors, such as the GPS unit 206 or the accelerometer 224, which may provide information regarding the vehicle 108 for autonomous operation and other purposes.

Furthermore, the communication unit 220 may communicate with other autonomous vehicles, infrastructure, or other external sources of information to transmit and receive information relating to autonomous vehicle operation. The communication unit 220 may communicate with the external sources via the network 130 or via any suitable wireless communication protocol network, such as wireless telephony (e.g., GSM, CDMA, LTE, etc.), Wi-Fi (802.11 standards), WiMAX, Bluetooth, infrared or radio frequency communication, etc. Furthermore, the communication unit 220 may provide input signals to the controller 204 via the I/O circuit 216. The communication unit 220 may also transmit sensor data, device status information, control signals, and/or other output from the controller 204 to one or more external sensors within the vehicle 108, mobile devices 110, on-board computers 114, and/or servers 140.

The mobile device 110 and/or the on-board computer 114 may include a user-input device (not shown) for receiving instructions or information from the vehicle operator, such as settings relating to an autonomous operation feature. The user-input device (not shown) may include a "soft" keyboard that is displayed on the display 202, an external hardware keyboard communicating via a wired or a wireless connection (e.g., a Bluetooth keyboard), an external mouse, a microphone, or any other suitable user-input device. The user-input device (not shown) may also include a microphone capable of receiving user voice input.

Exemplary Autonomous Vehicle Operation Method

Figure 3:
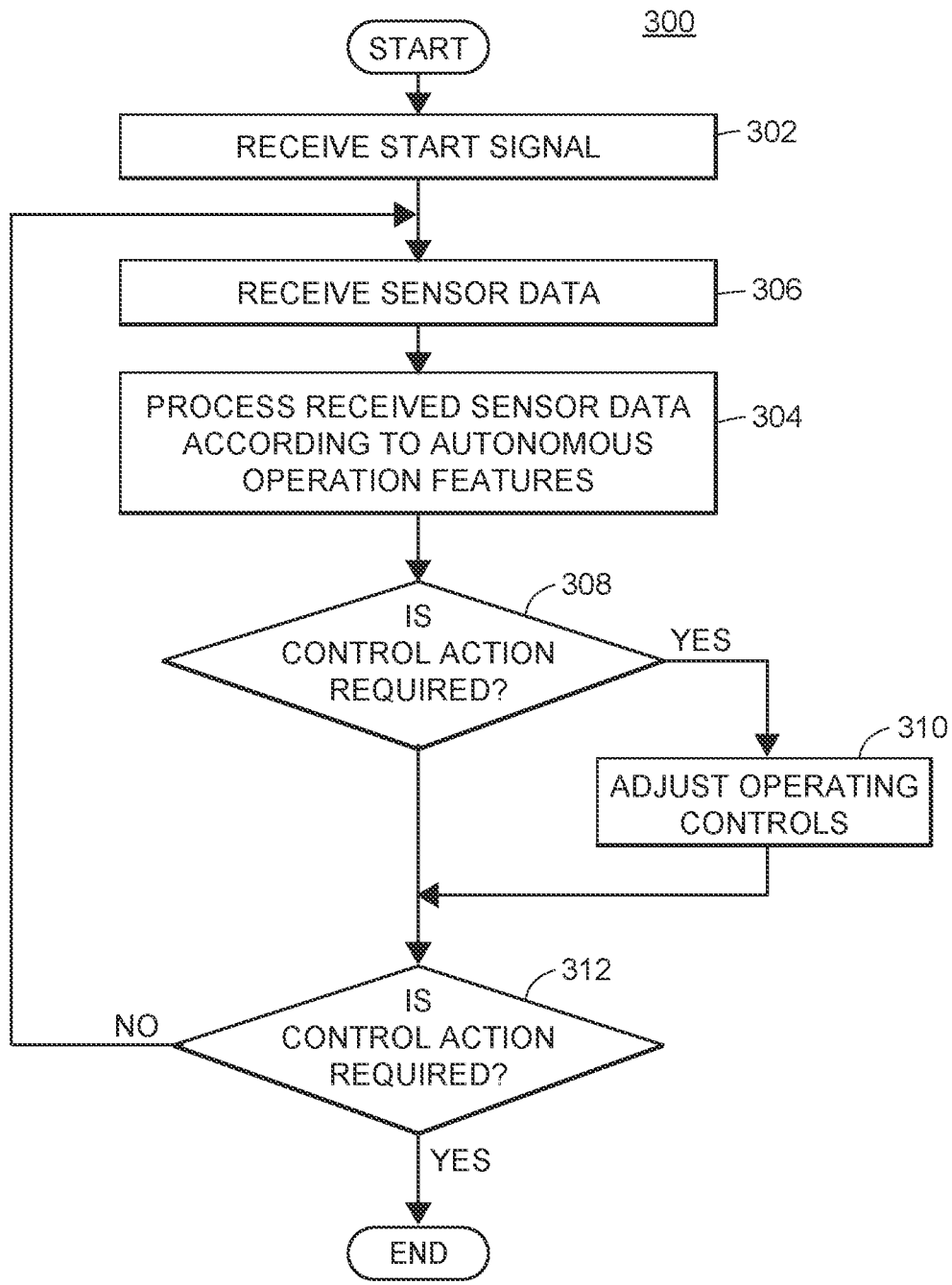
FIG. 3 illustrates a flow diagram of an exemplary autonomous vehicle operation method in accordance with the presently described embodiments.

FIG. 3 illustrates a flow diagram of an exemplary autonomous vehicle operation method 300, which may be implemented by the autonomous vehicle insurance system 100. The method 300 may begin at block 302 when the controller 204 receives a start signal. The start signal may be a command from the vehicle operator through the user-input device to enable or engage one or more autonomous operation features of the vehicle 108. In some embodiments, the vehicle operator 108 may further specify settings or configuration details for the autonomous operation features. For fully autonomous vehicles, the settings may relate to one or more destinations, route preferences, fuel efficiency preferences, speed preferences, and/or other configurable settings relating to the operation of the vehicle 108. In some embodiments, fully autonomous vehicles may include additional features or settings permitting them to operate without passengers or vehicle operators within the vehicle. For example, a fully autonomous vehicle may receive an instruction to find a parking space within the general vicinity, which the vehicle may do without the vehicle operator. The vehicle may then be returned to a selected location by a request from the vehicle operator via a mobile device 110 or otherwise. This feature may further be adapted to return a fully autonomous vehicle if lost or stolen.

For other autonomous vehicles, the settings may include enabling or disabling particular autonomous operation features, specifying thresholds for autonomous operation, specifying warnings or other information to be presented to the vehicle operator, specifying autonomous communication types to send or receive, specifying conditions under which to enable or disable autonomous operation features, and/or specifying other constraints on feature operation. For example, a vehicle operator may set the maximum speed for an adaptive cruise control feature with automatic lane centering. In some embodiments, the settings may further include a specification of whether the vehicle 108 should be operating as a fully or partially autonomous vehicle. In embodiments where only one autonomous operation feature is enabled, the start signal may consist of a request to perform a particular task (e.g., autonomous parking) and/or to enable a particular feature (e.g., autonomous braking for collision avoidance). In other embodiments, the start signal may be generated automatically by the controller 204 based upon predetermined settings (e.g., when the vehicle 108 exceeds a certain speed and/or is operating in low-light conditions). In some embodiments, the controller 204 may generate a start signal when communication from an external source is received (e.g., when the vehicle 108 is on a smart highway or near another autonomous vehicle).

After receiving the start signal at block 302, the controller 204 may receive sensor data from the sensors 120 during vehicle operation at block 304. In some embodiments, the controller 204 may also receive information from external sources through the communication component 122 and/or the communication unit 220. The sensor data may be stored in the RAM 212 for use by the autonomous vehicle operation application 232. In some embodiments, the sensor data may be recorded in the data storage 228 and/or transmitted to the server 140 via the network 130. The sensor data may alternately either be received by the controller 204 as raw data measurements from one of the sensors 120 and/or may be preprocessed by the sensor 120 prior to being received by the controller 204. For example, a tachometer reading may be received as raw data and/or may be preprocessed to indicate vehicle movement or position. As another example, a sensor 120 comprising a radar and/or LIDAR unit may include a processor to preprocess the measured signals and send data representing detected objects in 3-dimensional space to the controller 204.

The autonomous vehicle operation application 232, other applications 230, and/or routines 240 may cause the controller 204 to process the received sensor data at block 306 in accordance with the autonomous operation features. The controller 204 may process the sensor data to determine whether an autonomous control action is required and/or to determine adjustments to the controls of the vehicle 108. For example, the controller 204 may receive sensor data indicating a decreasing distance to a nearby object in the vehicle's path and process the received sensor data to determine whether to begin braking (and, if so, how abruptly to slow the vehicle 108). As another example, the controller 204 may process the sensor data to determine whether the vehicle 108 is remaining with its intended path (e.g., within lanes on a roadway). If the vehicle 108 is beginning to drift or slide (e.g., as on ice or water), the controller 204 may determine appropriate adjustments to the controls of the vehicle to maintain the desired bearing. If the vehicle 108 is moving within the desired path, the controller 204 may nonetheless determine whether adjustments are required to continue following the desired route (e.g., following a winding road). Under some conditions, the controller 204 may determine to maintain the controls based upon the sensor data (e.g., when holding a steady speed on a straight road).

When the controller 204 determines an autonomous control action is required at block 308, the controller 204 may cause the control components of the vehicle 108 to adjust the operating controls of the vehicle to achieve desired operation at block 310. For example, the controller 204 may send a signal to open or close the throttle of the vehicle 108 to achieve a desired speed. Alternatively, the controller 204 may control the steering of the vehicle 108 to adjust the direction of movement. In some embodiments, the vehicle 108 may transmit a message or indication of a change in velocity or position using the communication component 122 and/or the communication unit 220, which signal may be used by other autonomous vehicles to adjust their controls. As discussed further below, the controller 204 may also log or transmit the autonomous control actions to the server 140 via the network 130 for analysis.

The controller 204 may continue to receive and process sensor data at blocks 304 and 306 until an end signal is received by the controller 204 at block 312. The end signal may be automatically generated by the controller 204 upon the occurrence of certain criteria (e.g., the destination is reached or environmental conditions require manual operation of the vehicle 108 by the vehicle operator). Additionally, or alternatively, the vehicle operator may pause, terminate, and/or disable the autonomous operation feature or features using the user-input device or by manually operating the vehicle's controls, such as by depressing a pedal or turning a steering instrument. When the autonomous operation features are disabled or terminated, the controller 204 may either continue vehicle operation without the autonomous features or may shut off the vehicle 108, depending upon the circumstances.

Where control of the vehicle 108 must be returned to the vehicle operator, the controller 204 may alert the vehicle operator in advance of returning to manual operation. The alert may include a visual, audio, and/or other indication to obtain the attention of the vehicle operator. In some embodiments, the controller 204 may further determine whether the vehicle operator is capable of resuming manual operation before terminating autonomous operation. If the vehicle operator is determined not be capable of resuming operation, the controller 204 may cause the vehicle to stop and/or take other appropriate action.

Exemplary Monitoring Method During Operation

Figure 4:
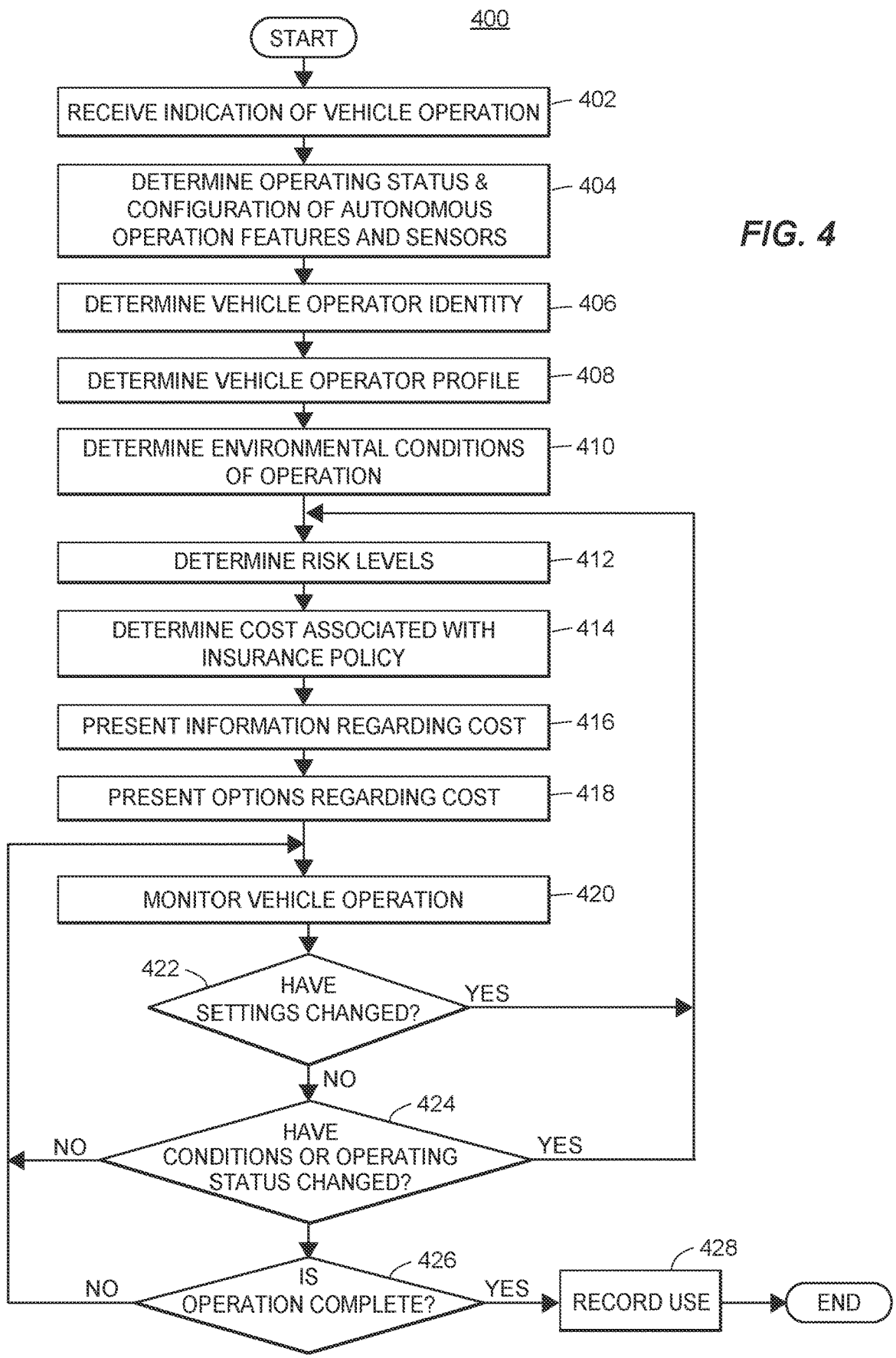
FIG. 4 illustrates a flow diagram of an exemplary monitoring method during vehicle operation in accordance with the presently described embodiments.

FIG. 4 illustrates a flow diagram depicting an exemplary monitoring method 400 during vehicle operation, which may be implemented by the autonomous vehicle insurance system 100. The method 400 may monitor the operation of the vehicle 108 and adjust risk levels and rates based upon vehicle use. Although the exemplary embodiment is described as primarily performed by the on-board computer 114, the method 400 may be implemented by the mobile device 110, the on-board computer 114, the server 140, or a combination thereof. Upon receiving an indication of vehicle operation at block 402, the on-board computer 114 may determine the configuration and operating status of the autonomous operation features (including the sensors 120 and the communication component 122) at block 404. The identity of the vehicle operator may be determined and/or verified at block 406, which identity may be used to determine or receive a vehicle operator profile at block 408. The vehicle operator profile may contain information regarding the vehicle operator's ability to manually operate the vehicle and/or past use of autonomous operation features by the vehicle operator. Information from the sensors 120 and/or external data from the communication component 122 may be used at block 410 to determine environmental conditions in which the vehicle 108 is operating. Together, this information determined at blocks 404-410 may be used at block 412 to determine one or more risk levels associated with operation of the vehicle, from which may be determined a costs associated with an insurance policy at block 414. In some embodiments, information regarding the determined cost may be presented to the vehicle operator or other insurance customer associated with the vehicle 108 at block 416. In still further embodiments, the vehicle operator and/or insurance customer may be presented with recommendations or options regarding the cost associated with the insurance policy at block 418. Presentation of options may assist the vehicle operator and/or insurance customer in reducing the cost by allowing the vehicle operator and/or insurance customer to select a lower-cost option (e.g., by adjusting the settings associated with the autonomous operation features). In some embodiments, the vehicle operator and/or insurance customer may be able to select one or more of the options to effect an adjustment in the risk levels and/or insurance cost.

The method 400 may continue monitoring operation of the vehicle 108 at block 420, and adjustments may be made to the risk levels and insurance costs. If the settings associated with the autonomous operation features are determined to have changed at block 422 (e.g., as a result of the vehicle operator taking manual operation of additional controls), the one or more risk levels may be determined based upon the new settings at block 412, in which case the blocks 414-422 may be repeated. When no changes have been made to the settings, the method 400 may further check for changes to the environmental conditions and/or operating status of the autonomous operation features at block 424. If changes are determined to have occurred at block 424, the one or more risk levels may be determined based upon the new settings at block 412, as at block 422. When no changes have occurred, the method 400 may determine whether vehicle operations are ongoing or whether operation is complete at block 426. When vehicle operation is ongoing, the method 400 may continue to monitor vehicle operation at block 420. When vehicle operation is complete, information regarding operation of the vehicle may be recorded at block 428, at which point the method 400 may terminate.

At block 402, the on-board computer 114 may receive an indication of vehicle operation. This indication may be received from the vehicle operator (either directly or through the mobile device 110), and/or it may be generated automatically. For example, the on-board computer 114 or the mobile device 110 may automatically generate an indication of vehicle operation when the vehicle starts operation (e.g., upon engine ignition, system power-up, movement of the vehicle 108, etc.). Upon receiving the indication of vehicle operation, the onboard computer 114 may initiate a system check and/or begin recording information regarding operation of the vehicle 108.

At block 404, the on-board computer 114 may determine the configuration and operating status of one or more autonomous operation features of the vehicle 108. This may include determining the configuration, settings, and/or operating status of one or more hardware or software modules for controlling part or all of the vehicle operation, aftermarket components disposed within the vehicle to provide information regarding vehicle operation, and/or sensors 120 disposed within the vehicle. In some embodiments, a software version, model version, and/or other identification of the feature or sensor may be determined. In further embodiments, the autonomous operation feature may be tested to assess proper functioning, which may be accomplished using a test routine or other means. Additionally, the sensors 120 or the communication component 122 may be assessed to determine their operating status (e.g., quality of communication connections, signal quality, noise, responsiveness, accuracy, etc.). In some embodiments, test signals may be sent to one or more of the sensors 120, responses to which may be received and/or assessed by the on-board computer to determine operating status. In further embodiments, signals received from a plurality of sensors may be compared to determine whether any of the sensors are malfunctioning. Additionally, signals received from the sensors may be used, in some embodiments, to calibrate the sensors.

At block 406, the on-board computer 114 may determine the identity of the vehicle operator. To determine the identity of the vehicle operator, the on-board computer 114 may receive and process information regarding the vehicle operator. In some embodiments, the received information may include sensor data from one or more sensors 120 configured to monitor the interior of the vehicle. For example, a camera or other photographic sensor may provide photographic information regarding the vehicle operator, which may be processed and compared with other photographic data for a plurality of persons to determine the identity of the vehicle operator. In further embodiments, the on-board computer may receive information from a mobile computing device associated with the vehicle operator, such as a mobile phone or wearable computing device. For example, a mobile phone may connect to the on-board computer 114, which may identify the vehicle operator. Additional steps may be taken to verify the identity of the vehicle operator, such as comparing a weight sensed on a seat or use of voice recognition algorithms.

At block 408, the on-board computer 114 may determine and/or access a vehicle operator profile based upon the identity of the vehicle operator determined at block 406. The vehicle operator profile may include information regarding the vehicle operator's style of operating the vehicle, including information regarding past operation of one or more vehicles by the vehicle operator. This information may further contain past vehicle operator selections of settings for one or more autonomous operation features. In some embodiments, the on-board computer 114 may request or access the vehicle operator profiled based upon the determined identity. In other embodiments, the on-board computer 114 may generate the vehicle operator profile from information associated with the identified vehicle operator. The vehicle operator profile may include information relating to one or more risks associated with operation of the vehicle by the vehicle operator. For example, the vehicle operator profile for a driver may include information relating to risk levels based upon past driving patters or habits in a variety of relevant environments, which may include risk levels associated with manual operation of the vehicle by the driver. In some embodiments, the vehicle operator profile may include information regarding default settings used by the vehicle operator for the autonomous operation features.

At block 410, the on-board computer 114 may determine environmental conditions within which the vehicle 108 is or is likely to be operating. Such environmental conditions may include weather, traffic, road conditions, time of day, location of operation, type of road, and/or other information relevant to operation of the vehicle. The environmental conditions may be determined based upon signals received from the sensors 120, from external data received through the communication component 122, and/or from a combination of sources. The environmental conditions may then be used in determining risk levels associated with operation of the vehicle 108.

At block 412, the on-board computer may determine one or more risk levels associated with operation of the vehicle 108. The risk levels may be determined based upon a combination of risk factors relating to the autonomous operation features and/or risk factors relating to the vehicle operation. Risks associated with the autonomous operation features may be determined based upon the configuration and/or operating status of the autonomous operation features, the settings of the autonomous operation features, and the vehicle environment. Risks associated with the vehicle operation may be determined based upon the autonomous operation features settings (i.e., the extent to which the vehicle operator will be controlling vehicle operations) and/or the vehicle operator profile. The combined risk may account for the likelihood of the autonomous operation features and/or the vehicle operator controlling vehicle operations with respect to relevant functions of the vehicle 108.

At block 414, the on-board computer 114 may determine a cost associated with an insurance policy based upon the one or more risks. In some embodiments, the server 140 may receive information regarding the vehicle operator and the autonomous operation features and/or may determine the cost associated with the insurance policy based upon the risks. The cost may be based upon risk levels associated with separate autonomous operation features, interaction between autonomous operation features, the design and capabilities of the vehicle 108, the past operating history of the vehicle operator as included in the vehicle operator profile, and/or other information regarding the probability of an accident, collision, and/or other loss event involving the vehicle 108. Each of the separate risks may depend upon the environmental conditions, and the risks may be weighted based upon the likelihood of each situation. In some embodiments, a total risk may be determined relating to operation of the vehicle under foreseeable conditions with specific settings and configurations of autonomous operation features by a specific vehicle operator. The total risk may be used to determine one or more costs associated with the insurance policy, such as a premium and/or discount.

In some embodiments, information regarding the cost associated with the insurance policy may be presented to the vehicle operator or insurance customer at block 416. The information may be presented by a display, such as the display 202 of the on-board computer 114 or the mobile device 110. The information may be presented either for informational purposes or to receive acceptance of the vehicle operator or insurance customer. The insurance cost information may include an indication of one or more of a premium, rate, rating, discount, reward, special offer, points level, program, refund, and/or other costs associated with one or more insurance policies. Additionally, or alternatively, summary information may be presented regarding insurance costs, including a risk level (e.g., high risk, low risk, a risk/cost level on a spectrum, etc.). In some embodiments, presentation of insurance cost information may be suppressed or delayed (e.g., cost information may be presented in summary form on a periodic billing statement).

In further embodiments, options or recommendations regarding the cost associated with the insurance policy may be presented to the vehicle operator or insurance customer at block 418. The options or recommendations may likewise be presented by a display, such as the display 202 of the on-board computer 114 and/or the mobile device 110. The options or recommendations may include information regarding costs associated with other settings or configurations of the autonomous operation features (e.g., enabling additional features, selecting an operating mode with lower risks under the determined environmental conditions, etc.). In some embodiments, the recommendations or options may be presented for informational purposes only, requiring the vehicle operator or insurance customer to make any adjustments separately (e.g., through a settings module or other means of adjusting settings for the autonomous operation features). In other embodiments, the vehicle operator or insurance customer may select one or more of the options, whereby adjustments to the configuration or settings of the autonomous operation features may be caused to be implemented by the on-board computer 114 or other controlling device. In some embodiments, the options or recommendations may include options or recommendations to update the software version of one or more autonomous operation features, in which case information regarding a cost associated with updating the features (if applicable) may be presented. Once the information and/or options or recommendations regarding insurance costs have been presented at blocks 416-418 (including, in some embodiments, while such presentation is occurring), the on-board computer 114 may monitor operation of the vehicle 108.

At block 420, the on-board computer 114 may monitor operation of the vehicle 108, including autonomous operation feature control decisions, signals from the sensors 120, external data from the communication component 122, and/or control decisions of the vehicle operator. Monitoring vehicle operation may include monitoring data received directly from the features, sensors, and/or other components, as well as summary information regarding the condition, movement, and/or environment of the vehicle 108. The on-board computer 114 and/or mobile device 110 may cause the operating data to be stored or recorded, either locally in the data storage 228 and/or via server 140 in the program memory 160 and/or the database 146. Monitoring may continue until vehicle operation is complete (e.g., the vehicle has reached its destination and shut down), including during any updates or adjustments.

At block 422, the on-board computer 114 may determine whether any changes have been made to the settings or configuration of the autonomous operation features. If such changes or adjustments have been made, the on-board computer 114 may proceed to determine new risk levels and insurance costs at blocks 412-414 and/or present the information to the vehicle operator or insurance customer at blocks 416-418, as discussed above. In some embodiments, minor changes below a minimum change threshold may be ignored when determining whether any changes have been made. In further embodiments, the cumulate effect of a plurality of such minor changes below the minimum change threshold may be considered as a change at block 422 when the cumulative effect of the minor changes reaches and/or exceeds the minimum change threshold. When no changes to the settings or configuration of the autonomous operation features are determined to have been made at block 422, the on-board computer 114 may further determine whether any changes in the environmental conditions and/or operating status of the autonomous operation features or sensors have occurred. Although these steps are illustrated separately for clarity, it should be understood that they may be further divided or combined in various embodiments.

At block 424, the on-board computer 114 may determine whether any changes have occurred to the environmental conditions of the vehicle 108 and/or the operating status of the autonomous operation features, sensors 120, or communication component 122. Such changes may occur when weather or traffic conditions change, when sensors 120 malfunction or become blocked by debris, and/or when the vehicle 108 leaves an area where external data is available via the communication component 122. When such changes occur, the risk levels associated with control of the vehicle 108 by the vehicle operator and the autonomous operation features may likewise change. Therefore, it may be advantageous to adjust the use of the autonomous operation features to account for such changes. Thus, the on-board computer 114 may proceed to determine new risk levels and insurance costs at blocks 412-414 and/or present the information to the vehicle operator or insurance customer at blocks 416-418, as discussed above, when such changes are determined to have occurred at block 424. Similar to the determination at block 422, minor changes below a minimum change threshold may be ignored at block 424, unless the cumulative effect of the changes reaches or exceeds the minimum change threshold. When no changes are determined to have occurred at block 424, the method 400 may continue to monitor the operation of the vehicle 108 until vehicle operation is determined to have ended.

At block 426, the on-board computer 114 may determine whether vehicle operations are complete. This may include determining whether a command to shut down the vehicle 108 has been received, whether the vehicle 108 has remained idle at a destination for a predetermined period of time, and/or whether the vehicle operator has exited the vehicle 108. Until operation is determined at block 426 to be complete (i.e., when the vehicle trip has concluded), the on-board computer 114 may continue to monitor vehicle operation at block 420, as discussed above. When operation is determined to be complete at block 426, the on-board computer 114 may further cause a record of the operation of the vehicle 108 to be made or stored. Such records may include operating data (in full or summary form) and may be used for assessing risks associated with one or more autonomous operation features or the vehicle operator. As noted above, in some embodiments, records of operating data may be generated and stored continually during operation. In some embodiments, the partial or completed records may be transmitted to the server 140 to be stored in the database 146. After completion and recordation of the vehicle operation, the method 400 may terminate.

Exemplary Methods for Determining Operating Status

Figure 5:
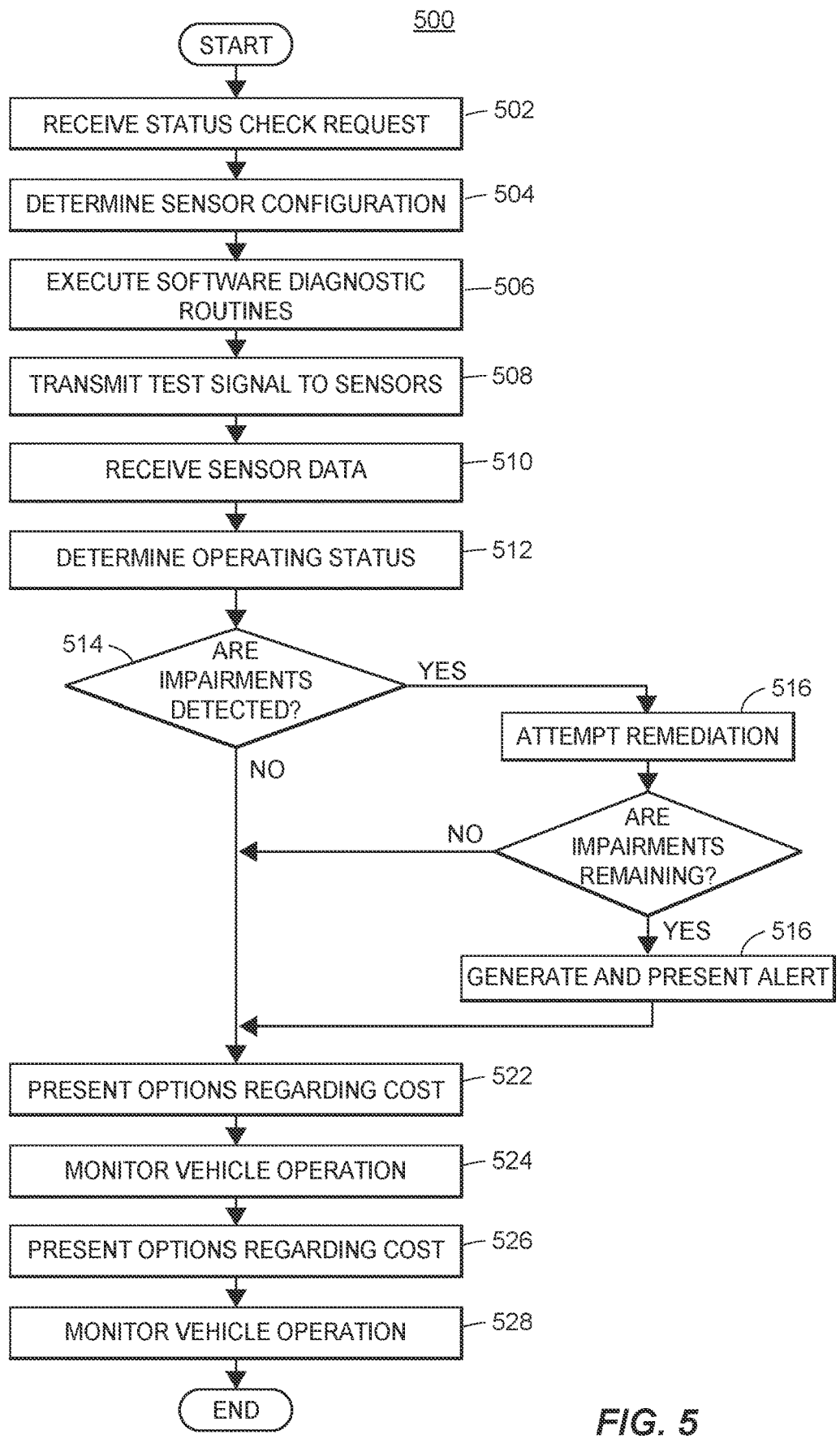
FIG. 5 illustrates a flow diagram of an exemplary operating status assessment method in accordance with the presently described embodiments.

FIG. 5 illustrates a flow diagram depicting an exemplary operating status assessment method 500 that may be used to determine operation status of the autonomous operation features, sensors 120, and/or communication component 122, as indicated in blocks 404 and 424 above. The method 500 may evaluate the autonomous operation features of the vehicle 108 (including sensors 120) and determine whether they are operating correctly, are malfunctioning, and/or are operating with impaired or degraded quality. Such determinations may be particularly important as the vehicle 108 ages or in environments that may block or damage sensors 120. In such cases, the original effectiveness of the autonomous operation features may be reduced as sensors become less accurate or processing of the sensor data is slowed (such as by software version updates that improve accuracy but require greater computational resources). The exemplary method 500 may be implemented regularly to ensure appropriate risk assessment, as well as periodically to certify the operating status level of the vehicle for roadworthiness or insurance rate adjustment. In some embodiments, periodic evaluation may be performed using special purpose computing devices and/or by licensed or authorized third parties. Periodic evaluation may further include more thorough testing and analysis of the vehicle 108, which may include testing at a test environment. Although the exemplary embodiment is described as primarily performed by the on-board computer 114, the method 500 may be implemented by the mobile device 110, the on-board computer 114, the server 140, or a combination thereof.

Upon receiving a request to determine the operating status of the autonomous operation features of the vehicle 108 at block 502, the configuration of the sensors 120 may be determined at block 504. The functioning of autonomous operation feature software routines may further be determined at block 506. A test signal may be transmitted to the sensors 120 at block 508, and/or sensor data may be received at block 510. The sensor data may include a response to the test signal, as well as other signals from the sensors based upon the vehicle environment or operation of the vehicle 108. Based upon the received information, the operating status of the autonomous operation features and components may be determined at block 512. If any impairments are detected at block 514, the method 500 may attempt to remediate the impairments at block 516. If impairments are detected to remain at block 518 after the remediation attempt, an alert may be generated and presented to the vehicle operator or an insurance customer at block 520. When no impairments are detected or after presentation of the alert, a report indicating the operational status of the autonomous operation features may be generated at block 522. In some embodiments, the report may be transmitted to an insurer at block 524, and/or a cost associated with an insurance policy associated with the vehicle 108 may be determined at block 526. The determined cost may be presented with the report at block 528 to the vehicle operator or insurance customer. Once the report has been presented, the exemplary method may end.

Figure 6:
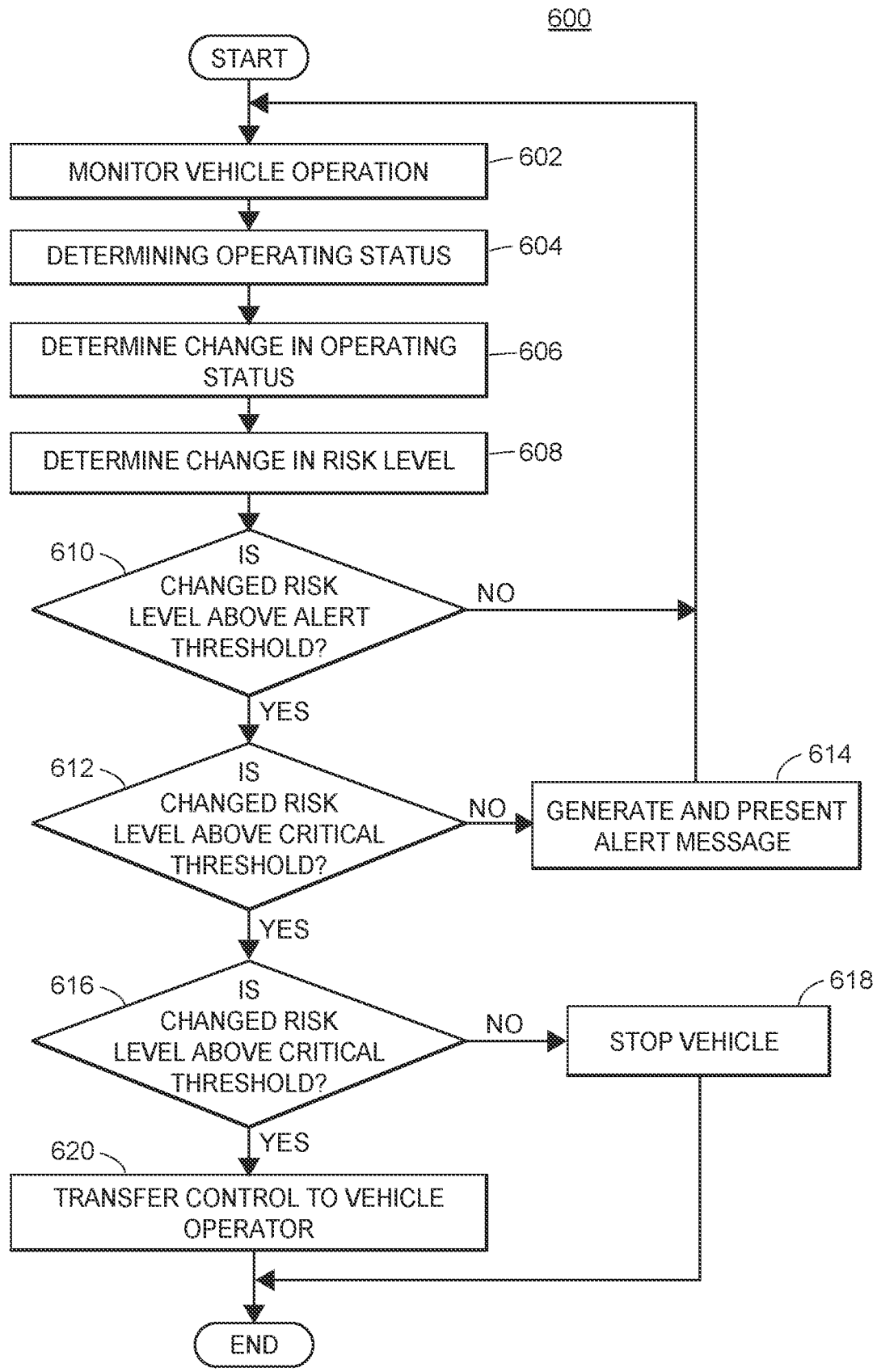
FIG. 6 illustrates a flow diagram of an exemplary operating status monitoring method in accordance with the presently described embodiments.

FIG. 6 illustrates a flow diagram of an exemplary operating status monitoring method 600 that may be used to determine operation status of the autonomous operation features, sensors 120, and/or communication component 122, in addition to or alternatively to the exemplary method 500 above. The method 600 may be implemented while the vehicle 108 is in operation to monitor the operating status of the autonomous operation features and components. The method 600 may monitor the vehicle operating data at block 602 to determine operating status of the autonomous operation features and components at block 604. When a change in operating status is detected at block 606, one or more corresponding changes in risk levels may be determined at block 608. If the changes in risk levels are determined to cause the risk levels to exceed an alert threshold but not a critical threshold at blocks 610 and 612, respectively, an alert is generated and presented to the vehicle operator at block 614. If the risk levels are determined to exceed the critical threshold at block 612, the method 600 may determine whether control of the vehicle 108 can be safely transferred to the vehicle operator at block 616. If the vehicle operator is prepared and able to assume control of the vehicle 108, then vehicle operation may be transferred to the vehicle operator at block 620. If control cannot be safely transferred, the vehicle 108 may cease operations and shut down at block 618. Once the vehicle 108 is no longer operating, the method 600 may terminate. Although the exemplary embodiment is described as primarily performed by the on-board computer 114, the method 600 may be implemented by the mobile device 110, the on-board computer 114, the server 140, or a combination thereof.

Exemplary Methods for Control Hand-Off

Figure 7A:
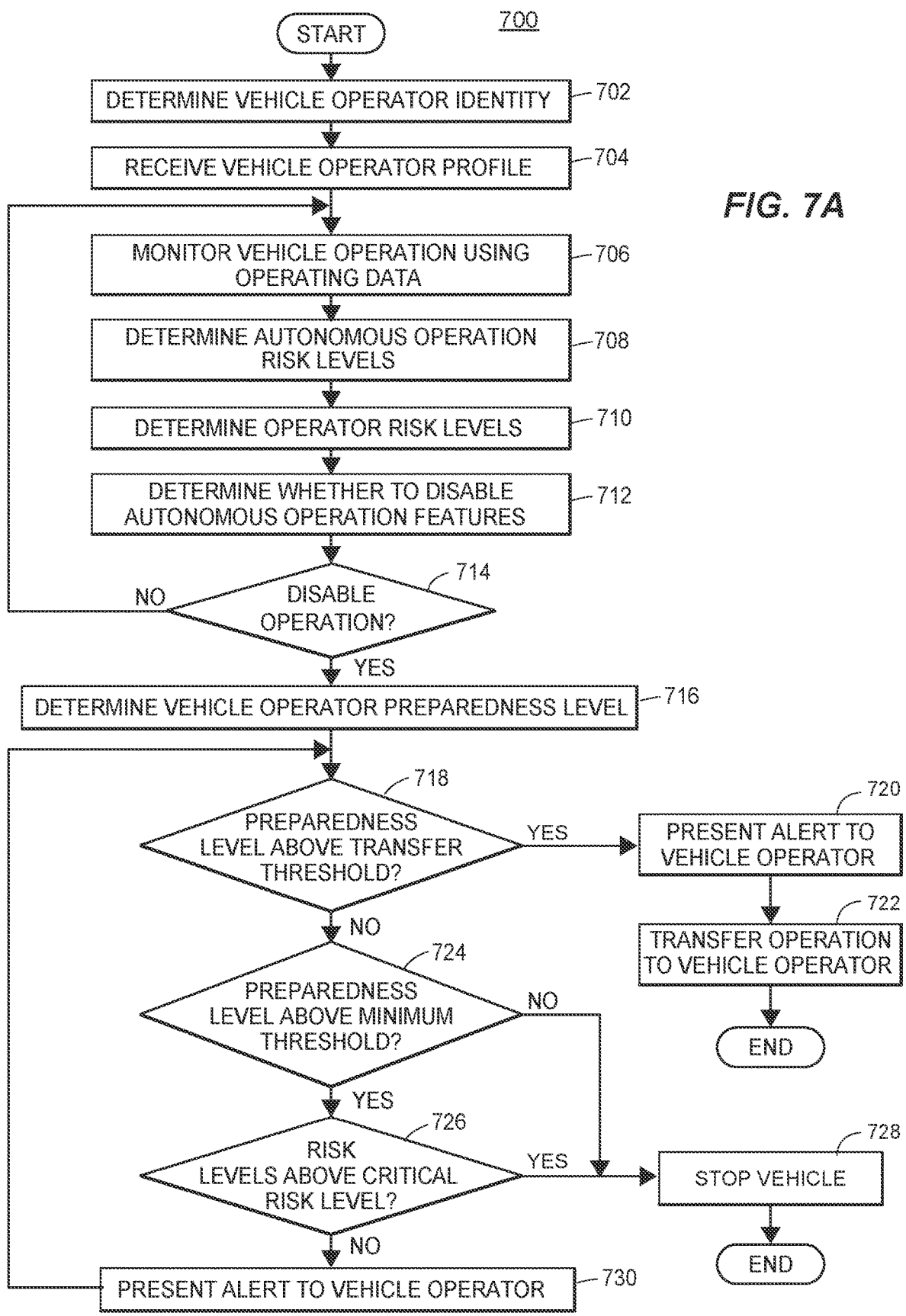
FIGS. 7A-B illustrate flow diagrams depicting exemplary vehicle operation hand-off methods in accordance with the presently described embodiments.
Figure 7B:
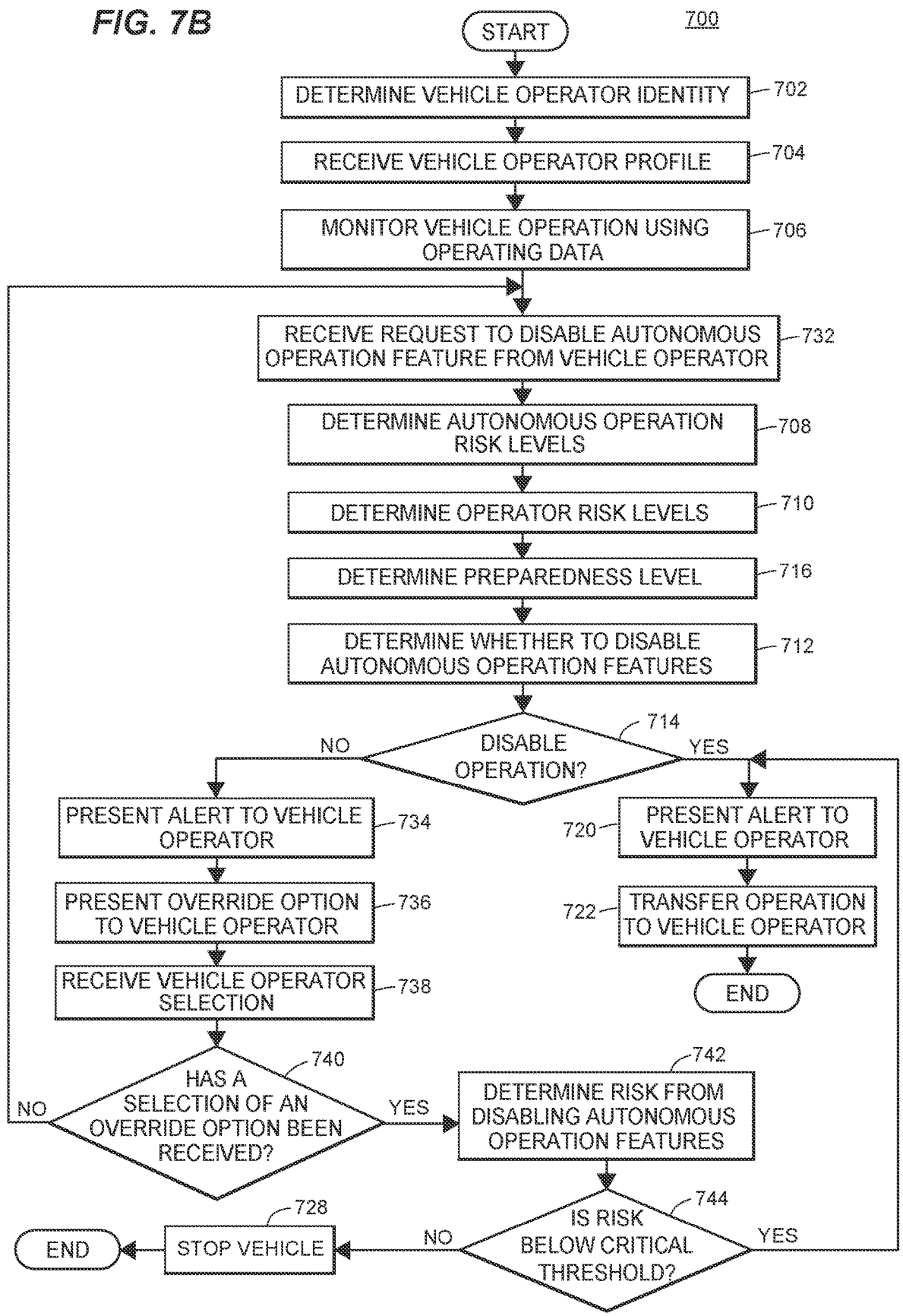

FIGS. 7A-B illustrate flow diagrams depicting exemplary vehicle operation handoff methods 700 that may be used to transfer operation of the vehicle 108 from one or more autonomous operation features to the vehicle operator. FIG. 7A illustrates hand-off of control when determined necessary based upon heightened risk levels associated with operation by the one or more autonomous operation features under the environmental conditions. FIG. 7B illustrates hand-off of control when requested by the vehicle operator while one or more autonomous operation features are performing vehicle control tasks. The methods 700 illustrated in FIGS. 7A and 7B may be combined or separately implemented in various embodiments. Although the exemplary embodiment is described as primarily performed by the on-board computer 114, the exemplary method 700 may be implemented by the mobile device 110, the on-board computer 114, the server 140, and/or a combination thereof.

Exemplary vehicle operation hand-off method 700 may be implemented at any time when one or more autonomous operation features are controlling part or all of the operation of the vehicle 108. The method 700 may begin by identifying the vehicle operator at block 702 and receiving a vehicle operator profile for the vehicle operator at block 704. At block 706, the operating data (including, in some embodiments, sensor data and external data) may be received and used to monitor operation of the vehicle 108. In some embodiments, a request to disable one or more autonomous operation features may be received from the vehicle operator at block 732. Autonomous risk levels associated with operation of the vehicle 108 by the autonomous operation features and operator risk levels associated with operation of the vehicle 108 by the vehicle operator may be determined at block 708 and 710, respectively. The determined risk levels may be used at block 712 to determine whether to disable one or more autonomous operation features. In some embodiments, the determination of whether to disable one or more autonomous operation features may further be based upon the preparedness level of the vehicle operator determined at block 716.

When it is determined to disable one or more autonomous operation features at block 714, the method 700 may transfer control to the vehicle operator. In some embodiments, this may include determining whether the vehicle operator is able to safely assume control by determining whether the vehicle operator's preparedness level is above a transfer threshold level at block 718. If so, an alert may be presented to the vehicle operator at block 720 to notify the vehicle operator of the transfer of control from the one or more autonomous operation features before transferring operation at block 722. If the vehicle operator's preparedness level is determined to be below the transfer threshold but above a minimum threshold at block 724, an alert may be presented at block 730 to attempt to prepare the vehicle operator to assume control if the risk levels associated with continued operation by the autonomous operation features do not exceed a critical risk threshold at block 726. Once the alert is presented to the vehicle operator at block 730, the vehicle operator's preparedness level may be determined again at block 716 and evaluated at block 718. If the risk levels exceed the critical threshold at block 726 or the vehicle operator's preparedness level is below the minimum threshold at block 724, the vehicle 108 may discontinue operation at block 728 and the method 700 may end.

When it is determined not to disable the one or more autonomous operation features at block 714, the method 700 may continue to monitor the operating data at block 706. If the vehicle operator requested that one or more autonomous operation features be disabled, the method 700 may present an alert at block 734 to notify the vehicle operator that disabling the autonomous operation features is not recommended. In some embodiments, options to override the determination not to disable the autonomous operation features may be presented to the vehicle operator at block 736, which the vehicle operator may select at block 738. If the vehicle operator is determined at block 740 to have not selected an option to override the determination, the method 700 may continue to monitor operation data at block 706. If the vehicle operator is determined at block 740 to have selected an option to override the determination, control of operation may be transferred from the one or more autonomous operation features to the vehicle operator. In some embodiments, one or more risk levels associated with disabling the autonomous operation features may be determined at block 742. If the risk levels are determined to be below a critical threshold at block 744, control may be transferred to the vehicle operator. If the risk levels meet or exceed the critical threshold at block 744, the vehicle 108 may instead discontinue operation at block 728 and the method 700 may end.

The method 700 as illustrated in FIG. 7A may begin at block 702 by determining the vehicle operator identity. The on-board computer 114 may determine the identity of the vehicle operator based upon information from one or more sensors 120 within the vehicle 108 and/or an indication of the vehicle operator identity from the mobile device 110 and/or another device carried or worn by the vehicle operator, as discussed further below. Once the identity of the vehicle operator is determined, the on-board computer 114 may request, access, and/or receive a vehicle operator profile associated with the vehicle operator at block 704, which may include information regarding risk levels associated with manual vehicle operation by the vehicle operator under various conditions, as discussed elsewhere herein. Such profile may for example, include details of past behavior of the vehicle operator under particular conditions, such as weather conditions, traffic conditions, time of day, time spent continuously operating the vehicle, health, distraction levels, etc.

At block 706, the on-board computer 114 may receive operating data for the vehicle 108 and/or monitor vehicle operation by one or more autonomous operation features and/or the vehicle operator. In some embodiments, the on-board computer 114 may receive operating data relating to the operation of the autonomous operation features, such as settings, configurations, software versions, control decisions, and/or other information indicating the actual or potential operation of the vehicle 108 by one or more autonomous operation features. The operating data may further include information from one or more sensors 120 communicatively connected to the on-board computer 114, which may include direct sensor signals generated by the sensors and/or processed or summarized sensor data based upon the direct sensor signals. In some embodiments, the operating data may further include external data from the communication component 122.

At block 708, the on-board computer 114 may determine one or more autonomous operation risk levels associated with operation of the vehicle 108 by one or more autonomous operation features based upon the operating data. The autonomous operation risk levels may further be based upon risk levels determined for the same or similar autonomous operation features, which risk levels may be determined by testing and/or actual loss data from other vehicles having the same or similar autonomous operation features. In some embodiments, information regarding risks associated with the one or more autonomous operation features may be obtained from the server 140 via the network 130. In further embodiments, the on-board computer 114 may transmit information regarding the operating data to the server 140 and/or receive one or more autonomous operation risk levels determined by the server 140. Additionally, or alternatively, the on-board computer 114 may transmit operating data or information regarding the autonomous operation risk levels to the server 140 to determine and/or adjust one or more costs associated with an insurance policy.

At block 710, the on-board computer 114 may determine one or more operator risk levels associated with operation of the vehicle 108 by the vehicle operator. Such operator risk levels may specifically correspond to the conditions of the vehicle, the vehicle's environment, or the vehicle operator. For example, such operator risk levels may indicate a risk assessment of the vehicle being driven manually by the vehicle operator at night, in heavy traffic, with an underinflated tire, or when the vehicle operator is showing indications of drowsiness. This information regarding the vehicle operator's risk levels may be used to determine whether the vehicle operator or the autonomous operation features are best suited to safely operate the vehicle based upon current conditions, as described below. In some embodiments, the operator risk levels may be based upon operating data recorded while the vehicle 108 or another vehicle was previously controlled in whole or part by the vehicle operator, and such data may be stored in a vehicle operator profile, as discussed elsewhere herein. Additionally, or alternatively, traditional actuarial risk factors may be included in determining the operator risk levels (e.g., age, vehicle, past accidents, etc.). This may be particularly useful, for example, where detailed operating data is not available for the vehicle operator. Similarly, operating data from a plurality of other vehicle operators may be used to predict or estimate vehicle operator risk levels.

Regardless of how the operator risk levels are generated, such operator risk levels may be generated in advance of vehicle operation and stored until needed. For example, a risk profile or risk table may be generated for the vehicle operator periodically (e.g., weekly or monthly) and stored in the data storage 228 of the mobile device 110 or on-board computer 114 for later use. In such embodiments, determining the one or more operator risk levels may include accessing the stored profile or table to obtain the risk levels during vehicle operation. As above, information regarding the vehicle operator and/or the operator risk levels may be received from, determined by, and/or transmitted to the server 140. In some embodiments, the server 140 may further use the information for determining and/or adjusting one or more costs associated with an insurance policy.

In one embodiment, the operator risk levels may be determined from a comparison of current road, environment, traffic, construction, or weather conditions with level settings indicating how the vehicle operator typically drives in such conditions. Such actual driving or driver behavior settings may be stored in the vehicle operator's vehicle operator profile. The driving behavior settings may be associated with road, weather, traffic, construction, or other traveling conditions through which the vehicle is currently traveling, including urban or rural roads, and daylight versus night time driving. The driving behavior settings may be associated with autonomous or semi-autonomous vehicle features, including those discussed elsewhere herein. Further driving behavior settings may be associated with the physical or mental condition of the vehicle operator, including alertness or emotional state.

At block 712, the on-board computer 114 may determine whether to disable the operation of one or more autonomous operation features based upon the determined autonomous operation risk levels and the determined operator risk levels. The determination may be based upon the one or more autonomous operation risk levels applicable to operation of the vehicle 108 by the one or more autonomous operation features under environmental conditions in which the vehicle 108 is operating. For example, the on-board computer 114 may determine that an autonomous operation feature (or combination of features) should be disabled because accuracy and/or reliability of the feature has dropped below an acceptable level for safe operation of the vehicle. Additionally, or alternatively, the determination may be based upon the relative risks associated with operation of the vehicle 108 by the one or more autonomous operation features and by the vehicle operator. For example, the on-board computer 114 may determine that the autonomous operation feature (or combination of features) should be disabled when the associated autonomous operation risk levels exceed the associated operator risk levels under the conditions of the vehicle environment. As another example, the on-board computer 114 may determine that the autonomous operation feature (or combination of features) should be disabled based upon the autonomous operation risk levels, but may further determine that the autonomous operation feature should not be disabled (notwithstanding the autonomous operation risk levels) because the corresponding operator risk levels are greater than the autonomous operation risk levels. Thus, the risk associated with autonomous operation may be high, but the risk associated with manual operation by the vehicle operator may be higher still. In such instances, the on-board computer 114 may determine whether the vehicle can be operated within certain critical safety levels and/or whether stopping the vehicle 108 until risk levels are reduce may be feasible under the conditions (e.g., whether the vehicle can pull off of a road until heavy rain passes, etc.).

In some embodiments, the on-board computer 114 may only determine that one or more autonomous operation features should be disabled if the autonomous operation risk levels exceed the corresponding operator risk levels by a minimum incremental amount and/or for a certain period of time. In further embodiments, the determination at block 712 may be based at least in part upon the availability and/or preparedness of the vehicle operator to assume control of relevant aspects of vehicle operation from the one or more autonomous operation features. It should be understood that the determination to disable the one or more autonomous operation features may be made for all autonomous operation features of the vehicle 108, for groups of autonomous operation features of the vehicle 108 (e.g., all autonomous operation features related to steering the vehicle), and/or for individual autonomous operation features of the vehicle 108.

When it is determined at block 714 that no autonomous operation features should be disabled, the on-board computer 114 may continue to monitor the operation of the vehicle 108 at block 706, as discussed above. When it is determined at block 714 that one or more autonomous operation features should be disabled, however, the on-board computer 114 may further determine a preparedness level of the vehicle operator at block 716. The preparedness level may indicate the ability of the vehicle operator to assume control of one or more functions of operating the vehicle 108 performed by the one or more autonomous operation features that should be disabled. Preparedness levels may be based upon sensor data regarding the vehicle operator (e.g., data from operator-facing cameras, biometric sensors, or physiological sensors). For example, sensor data may determine that the vehicle operator may be asleep and/or drowsy, resulting in a low preparedness level. In some embodiments, a plurality of preparedness levels may be determined, corresponding to a plurality of aspects of the vehicle operator's ability to make and/or execute control decisions regarding the vehicle 108, including alertness, distraction, irritation, fatigue, emotional state, and/or physical health. The determined preparedness level of the vehicle operator may then be used to determine whether and/or how to transfer operational control of the vehicle 108 to the vehicle operator.

At block 718, the on-board computer 114 may determine whether the vehicle operator's preparedness level is above a transfer threshold where the vehicle operator may be able to safely assume control functions from the one or more autonomous operation features. In some embodiments, the transfer threshold may be a predetermined value. In other embodiments, the transfer threshold may be determined based upon the operating status of the one or more autonomous operation features, the autonomous operation risk levels, the vehicle environment, and/or the estimated time available to transfer control. When the preparedness level exceeds the transfer threshold, the on-board computer 114 may present an alert to the vehicle operator to warn the vehicle operator of the transfer of operation at block 720. This alert may notify the vehicle operator that the one or more autonomous operation features will be disabled and provide time for the vehicle operator to assume control of the operations. The alert may include auditory, visual, haptic, and/or other types of alerts to attract the vehicle operator's attention, and information regarding the alert may be presented via the display 202 or by other means. In some embodiments, the alert may request or require a response from the vehicle operator to indicate attentiveness before transferring control. After presenting the alert to the vehicle operator at block 720, the on-board computer 114 may disable the one or more autonomous operation features, thereby transferring control of the associated aspects of vehicle operation to the vehicle operator at block 722.

In some embodiments, the on-board computer 114 may cause an indication of the transfer of the control functions of the one or more autonomous operation features to the vehicle operator to be generated and/or transmitted to the server 140. The indication may further include information regarding the one or more operator risk levels, operation data, and/or other information relevant to risk determination and/or insurance pricing. Transmission may occur via the network 130, either at the time of the transfer or at a later time. The server 140 may determine and/or adjust a cost associated with an insurance policy based upon the indication of the transfer of control, in any manner discussed herein.

When the preparedness level is determined to be at or below the transfer threshold at block 718, in some embodiments, the on-board computer 114 may further determine whether the preparedness level is above a minimum threshold at block 724. The minimum threshold may be set to a level indicating the vehicle operator may be prepared to assume operation of the vehicle functions within a sufficiently short period of time, which may be predetermined or determined based upon the circumstances of the hand-off in a manner similar to that discussed above. For example, the minimum threshold may indicate a level where the vehicle operator is awake. If the vehicle operator's preparedness level is above the minimum threshold at block 724, the on-board computer 114 may attempt to alert the vehicle operator that control should be transferred and/or one or more autonomous operation features should be disabled at blocks 726-730.

If the vehicle operator's preparedness level is below the minimum threshold, the on-board computer 114 may cause the vehicle 108 to discontinue operation and/or shut down at block 728. In order to safely discontinue operation of the vehicle 108, the on-board computer 114 may cause the vehicle 108 to navigate to a location where it can safely stop and/or shut down (e.g., a parking lot or road shoulder). In some embodiments, the determination of a location to discontinue operations may be based in part upon the one or more autonomous operation risk levels associated with continuing operation of the vehicle 108 by the autonomous operation features.

In some embodiments, the on-board computer 114 may determine whether the one or more autonomous operation risk levels exceed a critical risk threshold at block 726. The critical risk level may be predetermined or determined based upon the operating data, indicating a risk level above which the vehicle 108 should immediately begin stopping and discontinuing operations. For example, the total failure of a LIDAR system of the vehicle 108 may require immediate reversion to manual operation or cessation of vehicle operation. If the one or more autonomous operation risks are above the critical risk threshold (either individually or cumulatively), the vehicle 108 may discontinue operation at block 728, as discussed above. If the one or more autonomous operation risks do not exceed the critical risk threshold, however, the on-board computer 114 may cause an alert to be presented to the vehicle operator at block 730 to attempt to increase the vehicle operator's preparedness level. In addition to attempting to attract the vehicle operator's attention, the alert may indicate that the one or more autonomous operation features should be disabled. In some embodiments, presentation of the alert may include adjusting the vehicle operator's environment (e.g., interrupting music playback, adjusting temperature, and/or varying fan speed). Following presentation of the alert at block 730, the on-board computer 114 may continue to monitor and/or assess the vehicle operator to determine a new preparedness level at block 716. The blocks 716-730 may be implemented repeatedly until either a transfer of control to the vehicle operator occurs at block 722 or vehicle operation is discontinued at block 728.

The method 700 as illustrated in FIG. 7B may likewise be implemented by the onboard computer 114 to handle transfers of control from one or more autonomous operation features to the vehicle operator. At blocks 702 and 704, the on-board computer 114 may determine the vehicle operator's identity and receive an associated vehicle operator profile, as discussed above. At block 706, the on-board computer 114 may proceed to receive and/or monitor operating data, as discussed above. At block 732, the on-board computer 114 may receive from the vehicle operator and/or a third party a request to disable one or more autonomous operation features. The request may indicate specific autonomous operation features or groups of autonomous operation features to disable, and/or the request may include a request to implement a mode or profile including adjusting settings for one or more autonomous operation features. At blocks 708 and 710, the on-board computer 114 may determine one or more autonomous operation risk levels and one or more operator risk levels, as discussed above. Similarly, the on-board computer 114 may determine a preparedness level of the vehicle operator at block 716, as discussed above.

At block 712, the on-board computer 114 may determine whether to disable the one or more autonomous operation features based upon the autonomous operation risk levels, the operator risk levels, and/or the preparedness level. As discussed above, the determination may be based upon the absolute and/or relative risks associated with operation by the one or more autonomous operation features and/or the vehicle operator. In some embodiments, determining whether to disable the one or more autonomous operation features may include determining whether the absolute and/or relative risk level associated with operation of the vehicle by the vehicle operator without the autonomous operation features is within an acceptable range of risk levels. In some embodiments, the on-board computer 114 may determine not to disable autonomous operation features if the operator risk levels associated with manual control of the vehicle 108 may lead to a sharp increase in risk above a critical threshold under the environmental conditions in which the vehicle is operating. For example, a vehicle operator unaccustomed to driving in snow may request to disable autonomous operation features on a snow-covered road, in which case the on-board computer 114 may determine not to disable the autonomous operation features if the operator risk levels are too high. In further embodiments, the one or more operator risk levels may be adjusted based upon the vehicle operator's preparedness level. In other embodiments, the vehicle operator's preparedness level may be used to determine whether to disable the one or more autonomous operation features, as discussed with respect to FIG. 7A.

When it is determined that the one or more autonomous operation features may be disabled at block 714, the on-board computer 114 may cause an alert to be presented to the vehicle operator at block 720 in advance of transferring control at block 722, as discussed above. When it is determined not to disable the one or more autonomous operation features at block 714, the on-board computer 114 may cause another alert to be presented to the vehicle operator at block 734, indicating the determination not to disable the one or more autonomous operation features. In some embodiments, the alert at block 734 may indicate the reasons for not disabling the one or more autonomous operation features, the strength of the recommendation against disabling the one or more autonomous operation features, an indication of a change in risk levels associated with disabling the one or more autonomous operation features, an adjustment to a cost associated with an insurance policy related to disabling the one or more autonomous operation features, and/or other relevant information regarding disabling the one or more autonomous operation features.

At block 736, in some embodiments, the on-board computer 114 may further cause an option to override the determination not to disable the one or more autonomous operation features to be presented to the vehicle operator. In some embodiments, multiple options may be presented to allow the vehicle operator to override the determination with respect to some or all of the autonomous operation features. When the vehicle operator selects the option to override the determination, the on-board computer 114 may receive an indication of the selection at block 738. At block 740, the on-board computer 114 may determine whether an indication of a selection of an option to override the determination has been received. If no such indication has been received, the one or more autonomous operation features may continue to operate, and the on-board computer 114 may continue to monitor the operating data at block 706.

If an indication of a selection by the vehicle operator of an option to override the determination is received, the on-board computer 114 may still, in some embodiments, determine whether the risk from disabling the one or more autonomous operation features is within an acceptable range. At block 742, the on-board computer may determine one or more risk levels associated with disabling the one or more autonomous operation features based upon one or more of the operation data, the operator risk levels, and/or the autonomous operation risk levels. For example, the risk level associated with overriding a determination not to disable antilock brakes on an icy road may lead to a significant increase in the risk level associated with hard braking, as well as a high risk level for sliding or loss of steering control, particularly for a vehicle operator unfamiliar with such driving conditions. At block 744, the on-board computer 114 may determine whether the one or more risk levels are below a critical threshold. The critical threshold may represent a minimum standard of safe operation of the vehicle 108. In some embodiments, the on-board computer 114 may cause the one or more autonomous operation features to be disabled only if the one or more risk levels associated with disabling the one or more autonomous operation features are below the critical threshold. If the one or more risk levels are below the critical threshold, the vehicle 108 may discontinue operations at block 728, as discussed above. If the one or more risk levels meet or exceed the critical threshold, the on-board computer 114 may present an alert at block 720 and transfer control to the vehicle operator by disabling the one or more autonomous operation features at block 722, as above. In some embodiments, the on-board computer 114 may further transmit an indication that the one or more autonomous operation features have been disabled to the server 140, which may determine and/or adjust a cost associated with an insurance policy based upon a change in risk levels, as discussed elsewhere herein.

According to certain aspects, a computer-implemented method for operating an autonomous or semi-autonomous vehicle may be provided. With the customer's permission, an identity of a vehicle operator may be identified and a vehicle operator profile may be retrieved. Operating data regarding autonomous operation features operating the vehicle may be received from vehicle-mounted sensors. When a request to disable an autonomous feature is received, a risk level for the autonomous feature is determined and compared with a driver behavior setting for the autonomous feature stored in the vehicle operator profile. Based upon the risk level comparison, the autonomous vehicle retains control of vehicle or the autonomous feature is disengaged depending on which is the safer driver—the autonomous vehicle or the vehicle human occupant. As a result, unsafe disengagement of self-driving functionality for autonomous vehicles may be alleviated. Insurance discounts may be provided for autonomous vehicles having this safety functionality.

With all of the foregoing, a customer may opt into a rewards or other type of program, and willingly share their vehicle data with an insurance provider. In return, risk averse drivers and vehicle owners may receive discounts or insurance cost savings related to auto and other types of insurance from the insurance provider.

Selecting Best "Driver"

A. Current Road Conditions

In one aspect, a computer-implemented method of enhancing vehicle operation safety may be provided. The method may include (1) determining, via one or more processors (such as one or more local or remote processors, e.g., vehicle-mounted local processors or insurance provider remote processors), a current environment (or condition) through which a vehicle is traveling or about to travel through, the current environment (or condition) being associated with, or including, weather, traffic, construction, and/or road conditions, the vehicle being equipped with autonomous or semi-autonomous functionality or technology; (2) determining, via the one or more processors, whether it is safer for a human to drive the vehicle or for the vehicle to automatically drive itself (or otherwise engage the autonomous or semi-autonomous functionality or technology) based upon, or given, the current environment (or condition); and/or (3) generating, via the one or more processors, (i) an indication or recommendation to a driver to drive the vehicle if it is determined that it is safer for an average or typical human (or even that specific driver) to drive the vehicle given the current environment (or condition), or (ii) an indication or recommendation to the driver to engage the autonomous or semi-autonomous functionality or technology if it is determined that it is safer for the vehicle to automatically drive itself (or otherwise engage the autonomous or semi-autonomous functionality or technology) given the current environment (or condition) to facilitate safer vehicle travel and/or vehicle accident prevention. The method may include additional, fewer, or alternate actions, including those discussed elsewhere herein.

For instance, when it is determined that it is safer for the vehicle to automatically drive itself given the current environment (or condition), the one or more processors may automatically engage the autonomous or semi-autonomous functionality or technology. Additionally or alternatively, when it is determined that it is safer for an average human (or the specific driver, e.g., based upon a driver profile for the specific driver) to drive the vehicle given the current environment (or condition), the one or more processors may prevent engagement of the autonomous or semi-autonomous functionality or technology.

The method may also include gathering or collecting, at or via the one or more processors, driver behavior data of a specific driver over time, such as from one or more vehicle-mounted sensors that are in wired or wireless communication with the one or more processors; and/or building or updating a driver profile for the specific driver, at or via the one or more processors, from the driver behavior data gathered or collected over time. As a result, determining, via the one or more processors, whether it is safer for a human to drive the vehicle or for the vehicle to automatically drive itself based upon, or given, the current environment (or condition) may take into consideration the driver profile and/or driver behavior data associated with the specific driver.

The driver behavior data and/or driver profile may indicate how well the specific driver drives in rain, snow, sleet, ice, heavy traffic, road construction, stop-and-go traffic, bumper-to-bumper traffic, country or rural traffic, and/or city or downtown street traffic. The current environment (or condition) may include or be rain, ice, snow, fog, heavy traffic, bumper-to-bumper traffic, road construction, city traffic, country or rural traffic, and/or may be associated with a type of road, such as a two-lane or four-lane highway, or downtown city street or other street having several traffic lights.

The method may include updating or adjusting an insurance policy, premium, rate, reward, rewards or points program, and/or discount based upon the driver accepting or following the recommendation (regarding vehicle driver or mode of operation).

Determining, via one or more processors, a current environment (or condition) through which a vehicle is traveling or about to travel through may include the one or more processors receiving current or updated information regarding weather, traffic, construction, and/or road conditions via a wired or wireless communication network, such as over the internet and/or from third party or government websites. Additionally or alternatively, determining, via one or more processors, a current environment (or condition) through which a vehicle is traveling or about to travel through may include the one or more processors receiving current or updated information regarding weather, traffic, construction, and/or road conditions from one or more vehicle mounted sensors or cameras. Further, determining, via one or more processors, a current environment (or condition) through which a vehicle is traveling or about to travel through may include the one or more processors receiving current or updated information regarding weather, traffic, construction, and/or road conditions via wireless communication, such as via wireless communication or data transmission from another vehicle (vehicle-to-vehicle communication), from smart infrastructure (infrastructure-to-vehicle communication) (e.g., from smart traffic lights, smart street signs, smart exit ramps, smart bridges, and/or smart tollbooths), and/or from mobile devices (pedestrian-to-vehicle communication).

The method may include adjusting or updating, at or via an insurance provider remote processor or server, a life, home, renters, and/or health insurance policy (or associated premium, rate, rewards or points program, and/or discount) based upon driver usage of autonomous or semi-autonomous functionality or technology; an amount that the driver uses one or more different autonomous or semi-autonomous functionalities or technologies; and/or how well the specific driver uses, engages, and/or operates one or more autonomous or semi-autonomous functionalities or technologies.

B. Current Environment

In another aspect, a computer-implemented method of enhancing vehicle operation safety may be provided. The method may include (a) determining, via one or more processors (such as one or more local or remote processors, e.g., vehicle-mounted local processors or insurance provider remote processors), a current environment (or condition) through which a vehicle is traveling or about to travel through, the current environment (or condition) being associated with, or including, weather, traffic, construction, and/or road conditions, the vehicle being equipped with autonomous or semi-autonomous functionality or technology; (b) determining, via the one or more processors, that it is unsafe for the vehicle to operate with the autonomous or semi-autonomous functionality or technology engaged in, or given, the current environment (or condition) through which the vehicle is traveling or about to travel through; and/or (c) generating, via the one or more processors, an indication or recommendation to a driver to (1) continue to personally drive the vehicle; (2) take over human control of the vehicle (if the vehicle is driving itself); (3) not engage the autonomous or semi-autonomous functionality or technology; and/or (4) disengage the autonomous or semi-autonomous functionality or technology when it is determined that it is unsafe for the vehicle to operate with the autonomous or semi-autonomous functionality or technology engaged in, or given, the current environment (or condition) through which the vehicle is traveling or about to travel through to facilitate safe vehicle travel and/or vehicle accident prevention. The method may include additional, fewer, or alternate actions, including those discussed elsewhere herein.

For instance, the current environment (or condition) through which it is determined that it is unsafe for the vehicle to operate with the autonomous or semi-autonomous functionality or technology engaged may be or include rain, ice, snow, heavy traffic, bumper-to-bumper traffic, road construction, and/or may be associated with a certain type of road, such as a two-lane or four-lane highway, or downtown city street.

The method may include updating or adjusting an insurance policy, premium, rate, reward, rewards or point program, and/or discount based upon the driver accepting or following the recommendation (regarding vehicle driver (such as either human or vehicle) or mode of operation), or a percentage of time that the driver follows the recommendations provided.

Determining, via one or more processors, a current environment (or condition) through which a vehicle is traveling or about to travel through may include the one or more processors receiving current or updated information regarding weather, traffic, construction, and/or road conditions via a wired or wireless communication network, such as over the internet and/or from third party or government websites. Additionally or alternatively, determining, via one or more processors, a current environment (or condition) through which a vehicle is traveling or about to travel through may include the one or more processors receiving current or updated information regarding weather, traffic, construction, and/or road conditions from one or more vehicle-mounted sensors, cameras, or communication networks that capture information regarding conditions external to, and/or in front of, the vehicle. Further, determining, via one or more processors, a current environment (or condition) through which a vehicle is traveling or about to travel through may include the one or more processors receiving current or updated information regarding weather, traffic, construction, and/or road conditions via wireless communication, such as via wireless communication or data transmission from another vehicle (vehicle-to-vehicle communication), from smart infrastructure (infrastructure-to-vehicle communication) (e.g., from smart traffic lights, smart street signs, smart bridges or exit ramps, or smart tollbooths or overpasses), and/or from mobile devices (pedestrian-to-vehicle communication).

The method may include adjusting or updating, at or via an insurance provider remote processor or server, a life, home, renters, and/or health insurance policy (or associated premium, rate, rewards or points program, and/or discount) based upon driver usage of autonomous or semi-autonomous functionality or technology; an amount that the driver uses one or more different autonomous or semi-autonomous functionalities or technologies; and/or how well the specific driver uses, engages, and/or operates one or more autonomous or semi-autonomous functionalities or technologies.

C. Safety Comparison & Recommendations

In another aspect, a computer-implemented method of enhancing vehicle operation safety may be provided. The method may include (i) determining, via one or more processors (such as one or more local or remote processors, e.g., vehicle-mounted local processors or insurance provider remote processors), a current environment (or condition) through which a vehicle is traveling or about to travel through, the current environment (or condition) being associated with, or including, weather, traffic, construction, and/or road conditions, the vehicle being equipped with autonomous or semi-autonomous functionality or technology; (ii) determining, via the one or more processors, whether it is safer for (1) a human driver to drive the vehicle, or (2) the vehicle to operate with the autonomous or semi-autonomous functionality or technology engaged based upon, or given, the current environment (or condition) through which the vehicle is traveling or about to travel through; and/or (iii) generating, via the one or more processors, an indication or recommendation to the human driver whether it is safer for (a) the human driver to drive the vehicle, or (b) the vehicle to operate with the autonomous or semiautonomous functionality or technology engaged based upon, or given, the current environment (or condition) through which the vehicle is traveling or about to travel through to facilitate vehicle accident prevention and/or safer vehicle operation or travel. The method may include additional, fewer, or alternate actions, including those discussed elsewhere herein.

For instance, determining, via the one or more processors, whether it is safer for (1) a human driver to drive the vehicle, or (2) the vehicle to operate with the autonomous or semi-autonomous functionality or technology engaged based upon, or given, the current environment (or condition) through which the vehicle is traveling or about to travel through may be based upon (such as based upon a comparison of): (a) driving behavior or characteristic data for typical human drivers, or a driving profile for a specific driver built over time; and/or (b) safety ratings, profiles, or characteristic data for the autonomous or semi-autonomous functionality or technology.

The method may include updating or adjusting an insurance policy, premium, rate, reward, rewards or points program, and/or discount based upon the driver accepting or following the recommendation (regarding vehicle driver (human or vehicle) or mode of operation), or a percentage of time that the driver follows recommendations provided. Determining, via one or more processors, a current environment (or condition) through which a vehicle is traveling or about to travel through may include the one or more processors receiving current or updated information regarding weather, traffic, construction, and/or road conditions via a wired or wireless communication network, such as over the internet and/or from third party or government websites.

Determining, via one or more processors, a current environment (or condition) through which a vehicle is traveling or about to travel through may include the one or more processors receiving current or updated information regarding weather, traffic, construction, and/or road conditions from one or more vehicle-mounted sensors, cameras and/or communication networks that capture information regarding conditions external to, and/or in front of, the vehicle. Additionally or alternatively, determining, via one or more processors, a current environment (or condition) through which a vehicle is traveling or about to travel through may include the one or more processors receiving current or updated information regarding weather, traffic, construction, and/or road conditions via wireless communication, such as via wireless communication or data transmission from another vehicle (vehicle-to-vehicle communication) (e.g., from another vehicle traveling ahead of the vehicle or from a smart train); from smart infrastructure (infrastructure-to-vehicle communication) (e.g., from smart traffic lights, smart street signs, smart tollbooths, smart overpasses, smart buildings, smart bridges, smart train or bus system); and/or from mobile devices (pedestrian-to-vehicle communication).

The method may include adjusting or updating, at or via an insurance provider remote processor or server, a life, home, renters, or health insurance policy (or associated premium, rate, rewards or points program, and/or discount) based upon driver usage of autonomous or semiautonomous functionality or technology; an amount that the driver uses one or more different autonomous or semi-autonomous functionalities or technologies; and/or how well the specific driver uses, engages, and/or operates one or more autonomous or semi-autonomous functionalities or technologies.

D. Automatic Engagement

In another aspect, a computer-implemented method of enhancing vehicle operation safety may be provided. The method may include automatically engaging, via one or more processors (such as one or more local or remote processors, e.g., vehicle-mounted local processors or insurance provider remote processors), an autonomous or semi-autonomous functionality or technology of a vehicle when it is determined, by the one or more processors, that it is safer for the vehicle to operate with the autonomous or semi-autonomous functionality or technology engaged based upon, and/or comparison of: (a) one or more current environmental or road conditions through which the vehicle is currently traveling, or about to travel through, that are automatically determined by the one or more processors; (b) safety ratings, profiles, and/or characteristic data for the autonomous or semi-autonomous functionality or technology; and/or (c) driving behavior data and/or a driver profile for a specific driver that indicates how well the specific driver drives or otherwise operates the vehicle in the one or more current environmental or road conditions. The method may include additional, fewer, or alternate actions, including those discussed elsewhere herein.

For instance, the one or more current environmental or road conditions may include one or more weather, traffic, construction, road, and/or time of day conditions, and/or a weather condition indicates rain, snow, sun, clear, ice, cloudy, foggy, visibility, day (light outside), and/or night (dark outside). The method may include updating or adjusting an insurance policy, premium, rate, rewards or points program, and/or discount based upon the vehicle being configured to automatically engage the autonomous or semi-autonomous functionality or technology.

The method may include adjusting or updating, at or via an insurance provider remote processor or server, a life, home, renters, and/or health insurance policy (or associated premium, rate, rewards or points program, and/or discount) based upon driver usage of autonomous or semi-autonomous functionality or technology; an amount that the driver uses one or more different autonomous or semi-autonomous functionalities or technologies; and/or how well the specific driver uses, engages, and/or operates one or more autonomous or semi-autonomous functionalities or technologies.

E. Driving Behavior

In another aspect, a computer-implemented method of enhancing vehicle operation safety may be provided. The method may include (1) gathering or collecting, at or via one or more processors (such as one or more local or remote processors, e.g., vehicle-mounted local processors or insurance provider remote processors), driving behavior and/or characteristic data of a specific driver while the specific driver is driving a vehicle (or otherwise operating the vehicle) over time, the driving behavior and/or characteristic data being associated with, scoring, or indicative of, how well the driver drives (or otherwise operates the vehicle) in certain conditions, the certain conditions being associated with weather, traffic, construction, road, and/or other environmental conditions; (2) building a driver profile for the specific driver, via the one or more processors, from the driving behavior and/or characteristic data of the specific driver gathered or collected over time; (3) identifying or receiving, via the one or more processors, a current condition, such as a current weather, traffic, construction, and/or road condition (through which the vehicle is traveling through, or about to travel through); (4) determining, via the one or more processors, that a driving score or rating for the specific driver is below a certain threshold (such as a driving score or rating for an autonomous or semiautonomous functionality or technology) based upon analysis or comparison of (a) the current condition, and (b) the driver profile, and/or the driving behavior and/or characteristic data of the specific driver; and/or (5) in response, via the one or more processors, generating a message or recommendation for the driver to engage the autonomous or semi-autonomous functionality or technology of the vehicle and/or automatically engaging the autonomous or semi-autonomous functionality or technology to facilitate safer vehicle travel or accident prevention in unfavorable driving conditions, such as bad weather or road conditions. The method may include additional, fewer, or alternate actions, including those discussed elsewhere herein.

For instance, the method may further include, when it is determined, via the one or more processors, that the driving score and/or rating for the specific driver is below the certain threshold (such as the driving score or rating for an autonomous or semi-autonomous functionality or technology) given the current condition-which may indicate that the autonomous or semi-autonomous functionality or technology drives better in the unfavorable condition than the specific driver—the one or more processors may (i) prevent the specific driver from turning off the autonomous or semi-autonomous functionality or technology if previously engaged, or (ii) automatically engage the autonomous or semi-autonomous functionality or technology if not previously engaged to facilitate safer vehicle travel and/or accident prevention in unfavorable conditions.

The method may include updating or adjusting, via the one or more processors, an insurance policy, premium, rate, rewards or points program, and/or discount based upon the driver accepting or following the recommendation (regarding vehicle driver (such as either a human or vehicle driver being recommended) or mode of operation), or a percentage of time that the driver follows recommendations provided.

Identifying or receiving, via the one or more processors, the current condition through which a vehicle is traveling, or about to travel through, may include the one or more processors receiving current or updated information regarding weather, traffic, construction, and/or road conditions via a wired or wireless communication network, such as over the internet and/or from third party or government websites. Additionally or alternatively, identifying or receiving, via one or more processors, the current condition through which a vehicle is traveling, or about to travel through, may include the one or more processors receiving current or updated information regarding weather, traffic, construction, and/or road conditions from one or more vehicle mounted sensors, cameras, and/or communication networks that capture information regarding conditions external to, and/or in front of, the vehicle. Also, identifying or receiving, via one or more processors, a current condition through which a vehicle is traveling, or about to travel through, may include the one or more processors receiving current or updated information regarding weather, traffic, construction, and/or road conditions via wireless communication, such as via wireless communication or data transmission from another vehicle (vehicle-to-vehicle communication) (e.g., from another vehicle traveling ahead of the vehicle); from smart infrastructure (infrastructure-to-vehicle communication) (e.g., from smart traffic lights, smart street signs, smart tollbooths, smart overpasses, smart bridges, or smart buildings); and/or from mobile devices (pedestrian-to-vehicle communication).

The method may include adjusting or updating, at or via an insurance provider remote processor or server, a life, home, renters, and/or health insurance policy (or associated premium, rate, rewards or points program, and/or discount) based upon driver usage of autonomous or semi-autonomous functionality or technology; an amount that the driver uses one or more different autonomous or semi-autonomous functionalities or technologies; and/or how well the specific driver uses, engages, and/or operates one or more autonomous or semi-autonomous functionalities or technologies.

F. Driver Profile

In another aspect, a computer-implemented method of providing or enhancing vehicle operation safety may be provided. The method may include (1) building a driver profile over time, via one or more processors (such as one or more local or remote processors, e.g., vehicle mounted local processors or insurance provider remote processors), the driving profile including driving behavior and/or characteristic data associated with a specific driver of a vehicle, the driver behavior and/or characteristic data associated with driving scores or ratings for different environmental or roads conditions, such as different weather, traffic, construction, or road conditions; (2) identifying (or receiving data indicative of), via the one or more processors, one or more current environmental or road conditions (or other unfavorable driving condition) through which a vehicle is traveling or approaching; and/or (3) determining, via the one or more processors, that an autonomous or semi-autonomous functionality or technology drives the vehicle better than the specific driver in the one or more current environmental or road conditions based upon analysis or comparison of, via the one or more processors: (a) the current environmental or road conditions (or other unfavorable driving condition); (b) the driving profile, and/or driving behavior and/or characteristic data associated with the specific driver; and/or (c) driving score or rating of the autonomous or semi-autonomous functionality or technology, such as a score or rating associated with individual environmental or road conditions for that autonomous or semi-autonomous functionality or technology. The method may also include, when it is determined that the autonomous or semi-autonomous functionality or technology drives (or operates) the vehicle better than the specific driver in the one or more current environmental or road conditions, via the one or more processors: (i) preventing the specific driver from turning off the autonomous or semi-autonomous functionality or technology; (ii) automatically engaging the autonomous or semi-autonomous functionality to facilitate safer driving; and/or (iii) recommending that the specific driver employ or engage the autonomous or semi-autonomous functionality or technology to facilitate safer vehicle operation or accident prevention. The method may include additional, fewer, or alternate actions, including those discussed elsewhere herein.

For instance, the method may include updating or adjusting an insurance policy, premium, rate, rewards or points program, and/or discount based upon the driver accepting or following the recommendation (regarding vehicle driver or mode of operation), or a percentage of time that the driver follows recommendations provided. Identifying (or receiving data indicative of), via one or more processors, a current environmental or road condition (or other unfavorable driving condition) through which the vehicle is traveling, or approaching, may include the one or more processors receiving current or updated information regarding weather, traffic, construction, and/or road conditions via a wired or wireless communication network, such as over the internet and/or from third party or government websites.

Identifying (or receiving data indicative of), via one or more processors, a current environmental or road condition (or other unfavorable driving condition) through which the vehicle is traveling, or approaching, may include the one or more processors receiving current or updated information regarding weather, traffic, construction, and/or road conditions from one or more vehicle-mounted sensors or cameras that capture information regarding conditions external to, and/or in front of, the vehicle. Additionally or alternatively, identifying (or receiving data indicative of), via one or more processors, a current environmental or road condition (or other unfavorable driving condition) through which the vehicle is traveling or approaching may include the one or more processors receiving current or updated information regarding weather, traffic, construction, and/or road conditions via wireless communication, such as via wireless communication or data transmission from another vehicle (vehicle-to-vehicle communication) (e.g., from another vehicle traveling ahead of the vehicle); from smart infrastructure (infrastructure-to-vehicle communication) (e.g., from smart traffic lights, smart street signs, or smart tollbooths); and/or from mobile devices (pedestrian-to-vehicle communication).

The method may include adjusting or updating, at or via an insurance provider remote processor or server, a life, home, renters, and/or health insurance policy (or associated premium, rate, rewards or points program, and/or discount) based upon driver usage of autonomous or semi-autonomous functionality or technology; an amount that the driver uses one or more different autonomous or semi-autonomous functionalities or technologies; and/or how well the specific driver uses, engages, and/or operates one or more autonomous or semi-autonomous functionalities or technologies.

G. Driving Score

In another aspect, a computer-implemented method of providing or enhancing vehicle operation safety may be provided. The method may include (1) building a driver profile over time, via one or more processors (such as one or more local or remote processors, e.g., vehicle mounted local processors or insurance provider remote processors), the driving profile including driving behavior and/or characteristic data associated with a specific driver of a vehicle, the driver behavior and/or characteristic data associated with driving scores or ratings for different environmental or roads conditions, such as different weather, traffic, construction, or road conditions; (2) identifying (or receiving data indicative of), via the one or more processors, one or more current environmental or road conditions (or other unfavorable driving condition) through which a vehicle is traveling or approaching; (3) determining, via the one or more processors, that the specific driver drives or operates the vehicle better than an autonomous or semi-autonomous functionality or technology in the one or more current environmental or road conditions based upon analysis or comparison of, via the one or more processors: (a) the one or more current environmental or road conditions (or other unfavorable driving condition); (b) the driving profile, and/or driving behavior and/or characteristic data associated with the specific driver; and/or (c) a driving score or rating of the autonomous or semi-autonomous functionality or technology, such as a score or rating associated with individual environmental or road conditions for the autonomous or semi-autonomous functionality or technology. The method may include, when it is determined that the specific driver drives or operates the vehicle better than the autonomous or semi-autonomous functionality or technology in the one or more environmental or road conditions, via the one or more processors: (i) preventing the specific driver from turning on, switching to, or otherwise engaging, the autonomous or semi-autonomous functionality or technology; (ii) alerting the specific driver and then automatically dis-engaging the autonomous or semi-autonomous functionality or technology, or otherwise transferring driving responsibility back to the specific driver; and/or (iii) issuing a warning or recommendation to the specific driver to take control of the vehicle and/or manually dis-engage the autonomous or semi-autonomous functionality or technology to facilitate safer driving or vehicle operation. The method may include additional, fewer, or alternate actions, including those discussed elsewhere herein.

The method may include updating or adjusting, via the one or more processors, an insurance policy, premium, rate, rewards or points program, and/or discount based upon the driver accepting or following the recommendation (regarding vehicle driver (i.e., who should drive or operate the vehicle-a person or the vehicle) or mode of operation), or a percentage of time that the driver follows recommendations provided.

Identifying (or receiving data indicative of), via the one or more processors, a current environmental or road condition (or other unfavorable driving condition) through which the vehicle is traveling, or approaching, may include the one or more processors receiving current or updated information regarding weather, traffic, construction, and/or road conditions via a wired or wireless communication network, such as over the internet and/or from third party or government websites. Identifying (or receiving data indicative of), via the one or more processors, a current environmental or road condition (or other unfavorable driving condition) through which the vehicle is traveling, or approaching, may also include the one or more processors receiving current or updated information regarding weather, traffic, construction, and/or road conditions from one or more vehicle-mounted sensors or cameras that capture information regarding conditions external to, and/or in front of, the vehicle.

Additionally or alternatively, identifying (or receiving data indicative of), via the one or more processors, a current environmental or road condition (or other unfavorable driving condition) through which the vehicle is traveling, or approaching, may include the one or more processors receiving current or updated information regarding weather, traffic, construction, and/or road conditions via wireless communication, such as via wireless communication or data transmission from another vehicle (vehicle-to-vehicle communication)(e.g., from another vehicle traveling ahead of the vehicle or a train); from smart infrastructure (infrastructure-to-vehicle communication) (e.g., from smart traffic lights, smart street signs, or smart tollbooths); and/or from mobile devices (pedestrian-to-vehicle communication).

The method may include adjusting or updating, at or via an insurance provider remote processor or server, a life, home, renters, and/or health insurance policy (or associated premium, rate, rewards or points program, and/or discount) based upon driver usage of autonomous or semi-autonomous functionality or technology; an amount that the driver uses one or more different autonomous or semi-autonomous functionalities or technologies; and/or how well the specific driver uses, engages, and/or operates one or more autonomous or semi-autonomous functionalities or technologies.

Drowsy Driver

In one aspect, a computer-implemented method of enhancing vehicle safety may be provided. The method may include (1) capturing or gathering, via one or more processors (such as one or more local or remote processors, e.g., vehicle-mounted local processors or insurance provider remote processors), driver characteristic data associated with driver acuity of a driver of a vehicle (and/or including image or audio data); (2) comparing, via the one or more processors, the driver characteristic data with a first baseline of acuity information of normal drivers, or with a second baseline of acuity information for the driver collected over time, the first or second baseline being stored in a memory unit accessible by the one or more processors; (3) based upon the comparison, via the one or more processors, determining that the driver is drowsy and/or is otherwise associated with a higher than normal risk of vehicle accident; and/or (4) in response, via the one or more processors, engaging autonomous or semi-autonomous functionality or technology (or self-driving functionality) of the vehicle, and/or recommending to the driver to engage the autonomous or semi-autonomous functionality or technology (or self-driving functionality) of the vehicle to facilitate accident prevention and/or safer driving or vehicle operation. The method may include additional, fewer, or alternate actions, including those discussed elsewhere herein.

For instance, the one or more processors may determine that the driver is drowsy based upon images of the driver, and facial recognition software techniques and/or analysis of eyes or eye behavior of the driver, and/or body or head position or behavior of the driver. The method may include updating or adjusting, via the one or more processors, an insurance policy, premium, rate, rewards or points program, and/or discount based upon the driver accepting or following the recommendation (regarding vehicle driver (such as either a human or vehicle driver) or mode of operation), or a percentage of time that the driver follows recommendations provided.

Unsafe Driver

In another aspect, a computer-implemented method of enhancing vehicle operation safety may be provided. The method may include (1) gathering or collecting, at or via one or more processors (such as one or more local or remote processors, e.g., vehicle-mounted local processors or insurance provider remote processors), driving behavior or characteristic data of a specific driver while the specific driver is driving a vehicle, the data being generated or collected by one or more vehicle-mounted sensors, cameras, processors, and/or systems (and/or including image and/or audio data); (2) determining, at or via one or more processors, that the driver is driving the vehicle in an unsafe manner based upon computer analysis of the driving behavior or characteristic data; and/or (3) automatically engaging, via one or more processors, an autonomous or semi-autonomous functionality or technology of a vehicle when it is determined, by the one or more processors, that it is safer for the vehicle to operate with the autonomous or semi-autonomous functionality or technology engaged based upon computer analysis of the driving behavior or characteristic data and/or the determination that the driver is driving or operating the vehicle in an unsafe manner. The method may include additional, fewer, or alternate actions, including those discussed elsewhere herein.

For instance, the computer analysis of the driving behavior or characteristic data and/or the determination that the driver is driving or operating the vehicle in an unsafe manner may be based upon, or may include, a determination, via the one or more processors, that the vehicle is swerving; not staying in the correct lane; not staying on the road; switching or crossing lanes improperly; not stopping at stop signs or traffic lights; not signaling correctly; traveling in the wrong direction or lane; traveling on the wrong side of a two-lane road; traveling too slow for road conditions or a posted speed limit; and/or traveling too fast for road conditions or the posted speed limit. The determination that the driver is driving or operating the vehicle in an unsafe manner may be based upon a determination that the vehicle is being operated in an unsafe manner or not according to, or in accordance with, driving laws or statutes, or posted speed limits.

Inattentive or Distracted Driver

In one aspect, a computer-implemented method of enhancing vehicle safety or operation may be provided. The method may include (1) capturing or gathering, via one or more processors (such as one or more local or remote processors, e.g., vehicle-mounted local processors or insurance provider remote processors), driver characteristic or behavior data associated with driver attentiveness, or lack thereof, of a specific driver of a vehicle, the driver characteristic or behavior data including image or audio data associated with the specific driver and/or an interior of the vehicle; (2) comparing, via the one or more processors, the driver characteristic or behavior data with a first baseline of attentiveness information of normal or average drivers, or with a second baseline of attentiveness for the specific driver collected over time, the first or second baseline being stored in a memory unit; (3) based upon the comparison, via the one or more processors, determining that the specific driver is un-attentive, distracted, or is otherwise associated with a higher than normal risk of vehicle accident; and/or (4) in response, via the one or more processors, engaging autonomous or semi-autonomous functionality or technology (or self-driving functionality) of the vehicle, and/or recommending to the specific driver to engage the autonomous or semi-autonomous functionality or technology (or self-driving functionality) of the vehicle to facilitate accident prevention and/or safer driving or vehicle operation. The method may include additional, fewer, or alternate actions, including those discussed elsewhere herein.

For instance, the one or more processors may determine that the specific driver is un-attentive or distracted based upon computer analysis of images of the specific driver, and/or the computer analysis of the image data may indicate that the driver is not looking forward, or otherwise not looking in the direction of vehicle travel. The one or more processors may determine that the specific driver is un-attentive or distracted based upon computer analysis of images of the specific driver, and/or the computer analysis of the image data may indicate that the specific driver is looking toward the passenger seat, looking down (such as texting), is looking into the back seat area of the vehicle, and/or not looking forward or in the direction of vehicle travel.

The one or more processors may determine that the specific driver is un-attentive or distracted based upon computer analysis of images of the specific driver, and/or the computer analysis of the image data may indicate that the specific driver is texting or talking on a smart phone. Additionally or alternatively, the one or more processors may determine that the specific driver is un-attentive or distracted based upon computer analysis of images of the specific driver, and/or the computer analysis of the image data may indicate that the specific driver is moving their arms or head in a manner abnormal for driving.

The one or more processors may determine that the specific driver is un-attentive or distracted based upon computer analysis of images of the specific driver, and/or the computer analysis of the image data may indicate an abnormal position for driving, or unsafe for driving position, of one or more hands of the specific driver or the head of the specific driver. Additionally or alternatively, the one or more processors may determine that the specific driver is un-attentive or distracted based upon computer analysis of the audio data, and/or the computer analysis of the audio data may indicate abnormal noise, sounds, or voices within the interior of the vehicle.

The method may include updating or adjusting, via the one or more processors, an insurance policy, premium, rate, rewards or points program, and/or discount based upon the specific driver accepting or following the recommendation (regarding vehicle driver, such as either recommending a human or vehicle driver, or mode of operation), or a percentage of time that the specific driver follows recommendations provided.

Prevent Autonomous Functionality Engagement During Inclement Weather

In one aspect, a computer-implemented method of enhancing vehicle operation or safety may be provided. The method may include (1) determining, via one or more processors, that an autonomous or semi-autonomous functionality or technology of a vehicle is not operating correctly or optimally, or otherwise is unsafe for current weather or road conditions; (2) generating, via the one or more processors, a warning to a driver of the vehicle indicating that the autonomous or semi-autonomous functionality or technology is not operating correctly or optimally, or otherwise is unsafe for current weather or road conditions; and/or (3) preventing, via the one or more processors, the driver of the vehicle from engaging or switching on the autonomous or semi-autonomous functionality or technology that is not operating correctly or optimally, or otherwise is unsafe for current weather or road conditions. The method may include additional, fewer, or alternate actions, including those discussed elsewhere herein.

For instance, the method may include (a) generating, via the one or more processors, a wireless communication indicating that the autonomous or semi-autonomous functionality or technology is not operating correctly or optimally, or otherwise is unsafe for current weather or road conditions; (b) transmitting, via the one or more processors, the wireless communication to an insurance provider remote processor or server; and/or (c) adjusting or updating, at or via the insurance provider remote processor or server, an insurance policy, premium, rate, rewards or points program, and/or discount for the vehicle based upon the autonomous or semi-autonomous functionality or technology not operating correctly or optimally, or otherwise being unsafe for current weather or road conditions.

The method may include (1) receiving, at or via the insurance provider remote processor or server, via wireless communication from a mobile device of an insured that the autonomous or semi-autonomous functionality or technology that was not operating correctly or optimally was repaired and/or received maintenance, and/or is now operating correctly or optimally, or otherwise operating safely; and/or (2) adjusting or updating, at or via the insurance provider remote processor or server, an insurance policy, premium, rate, rewards or points program, and/or discount for the vehicle based upon the autonomous or semi-autonomous functionality or technology operating correctly or optimally.

Determining, via the one or more processors, that the autonomous or semi-autonomous functionality or technology of a vehicle is not operating correctly or optimally, or otherwise is unsafe for current weather or road conditions may be based upon rain, snow, fog, and/or limited visibility conditions. Additionally or alternatively, determining, via the one or more processors, that the autonomous or semi-autonomous functionality or technology of a vehicle is not operating correctly or optimally, or otherwise is unsafe for current weather or road conditions may be based upon one or more vehicle-mounted sensors not operating correctly or being covered by snow, ice, salt, dirt, dust, mud, and/or new or touch-up paint.

Further, determining, via one or more processors, that the autonomous or semiautonomous functionality or technology of the vehicle is not operating correctly or optimally, or otherwise is unsafe for current weather or road conditions may be based upon recognizing an abnormal or unusual condition, such as one or more pedestrians or traffic policeman being identified or recognized within a vicinity of, or approaching, the vehicle. Additionally or alternatively, determining, via one or more processors, that the autonomous or semi-autonomous functionality or technology of the vehicle is not operating correctly or optimally, or otherwise is unsafe for current weather or road conditions may be based upon recognizing an abnormal condition, such as a traffic light being identified or recognized within a vicinity of, or approaching, the vehicle as not working or operating correctly.

Engage Autonomous Functionality in Bad Weather

In one aspect, a computer-implemented method of enhancing safe vehicle operation may be provided. The method may include (1) determining, via one or more processors (such as a vehicle mounted processor and/or an insurance provider remote processor), that a current (or approaching) weather condition (such as rain, snow, ice, or hail) presents a hazard or potential hazard to a vehicle, the vehicle being equipped with autonomous or semi-autonomous functionality or technology; and/or (2) in response (or based upon the foregoing determination), via the one or more processors, the vehicle may engage the autonomous or semi-autonomous functionality or technology, or may recommend to the driver to engage the autonomous or semi-autonomous functionality or technology, to facilitate safer vehicle operation, driving, or travel and/or accident prevention. The method may include additional, fewer, or alternate actions, including those discussed elsewhere herein.

For instance, the method may include updating or adjusting, via the one or more processors or at an insurance provider remote processor or server, an insurance policy, premium, rate, rewards or points program, and/or discount based upon the vehicle automatically engaging the autonomous or semi-autonomous functionality or technology when it is determined that the current (or approaching) weather condition (such as rain, snow, ice, or hail) presents the hazard or potential hazard to the vehicle. The method may further include adjusting or updating, at or via an insurance provider remote processor or server, a life, home, renters, and/or health insurance policy (or associated premium, rate, rewards or points program, and/or discount) based upon driver usage of autonomous or semi-autonomous functionality or technology; an amount that the driver uses one or more different autonomous or semi-autonomous functionalities or technologies; and/or how well the specific driver uses, engages, and/or operates one or more autonomous or semi-autonomous functionalities or technologies.

Exemplary Methods for Vehicle Operator Identification

Figure 8:
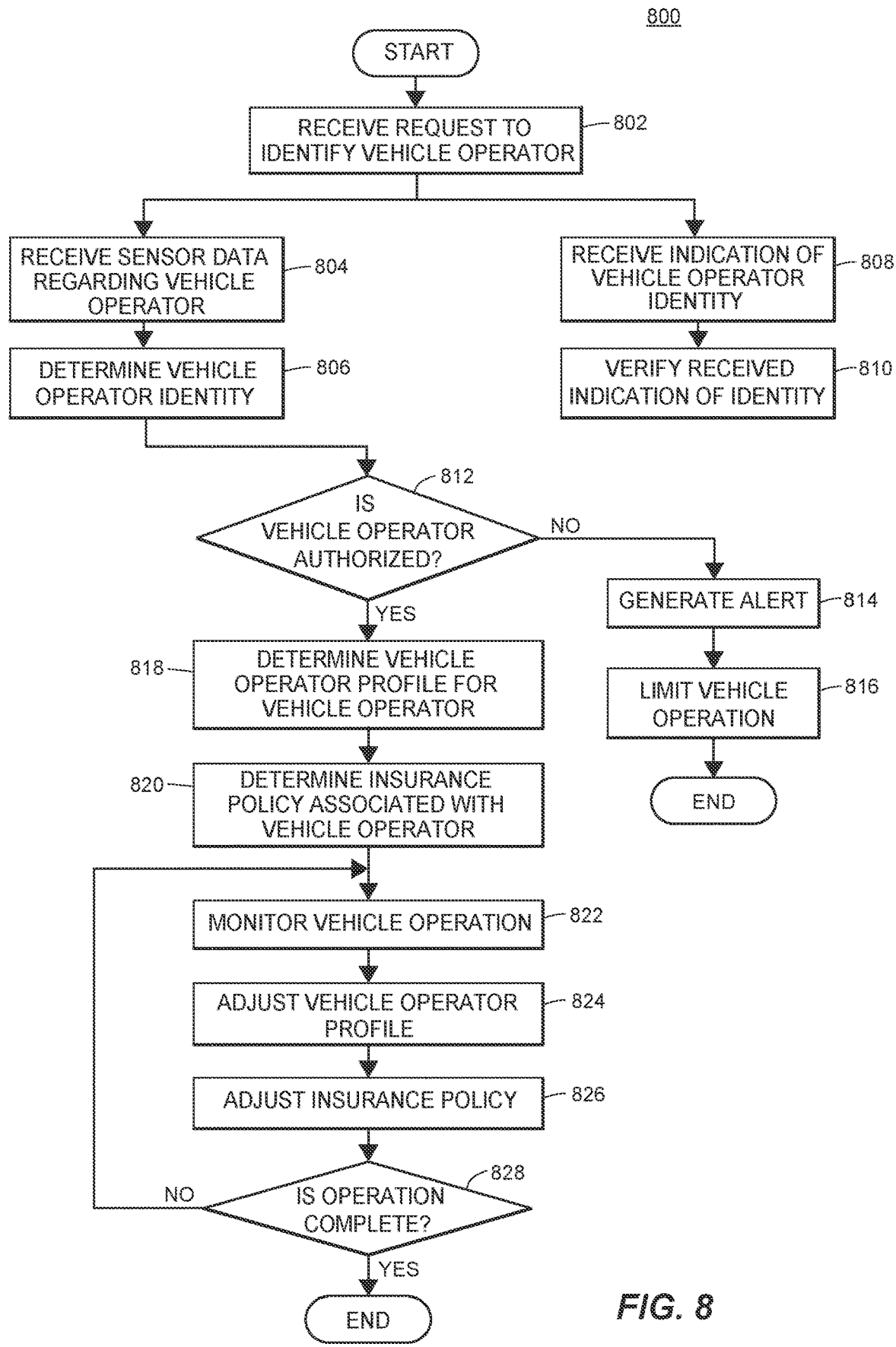
FIG. 8 illustrates a flow diagram depicting an exemplary vehicle operator identification method in accordance with the presently described embodiments.

FIG. 8 illustrates a flow diagram depicting an exemplary vehicle operator identification method 800 that may be used to adjust an insurance policy associated with the vehicle operator or vehicle 108. The exemplary method 800 may begin with receipt of a request to identify the vehicle operator of the vehicle at block 802. At blocks 804-810, the vehicle operator may be identified by sensor data or received indications of identity, such as from a mobile device 110. Once the identity of the vehicle operator has been determined (or cannot be determined), the method 800 may further determine whether the vehicle operator is authorized to operate the vehicle 108 at block 812. If the vehicle operator is not authorized, an alert may be generated and vehicle operations may be limited at blocks 814-816. If the vehicle operator is authorized, a vehicle operator profile associated with the vehicle operator may be obtained at block 818, and/or an insurance policy associated with the vehicle 108 or the vehicle operator may be identified at block 820. During vehicle operation, operating data of the vehicle 108 may be received and used to adjust the vehicle operator profile and the insurance policy at blocks 822-826. When vehicle operation has been determined to be complete at block 828, the method 800 may terminate. Although the exemplary embodiment is described as primarily performed by the on-board computer 114, the method 800 may be implemented by the mobile device 110, the on-board computer 114, the server 140, and/or a combination thereof.

Exemplary Methods for Monitoring Use by Vehicle Opera Tors

Figure 9:
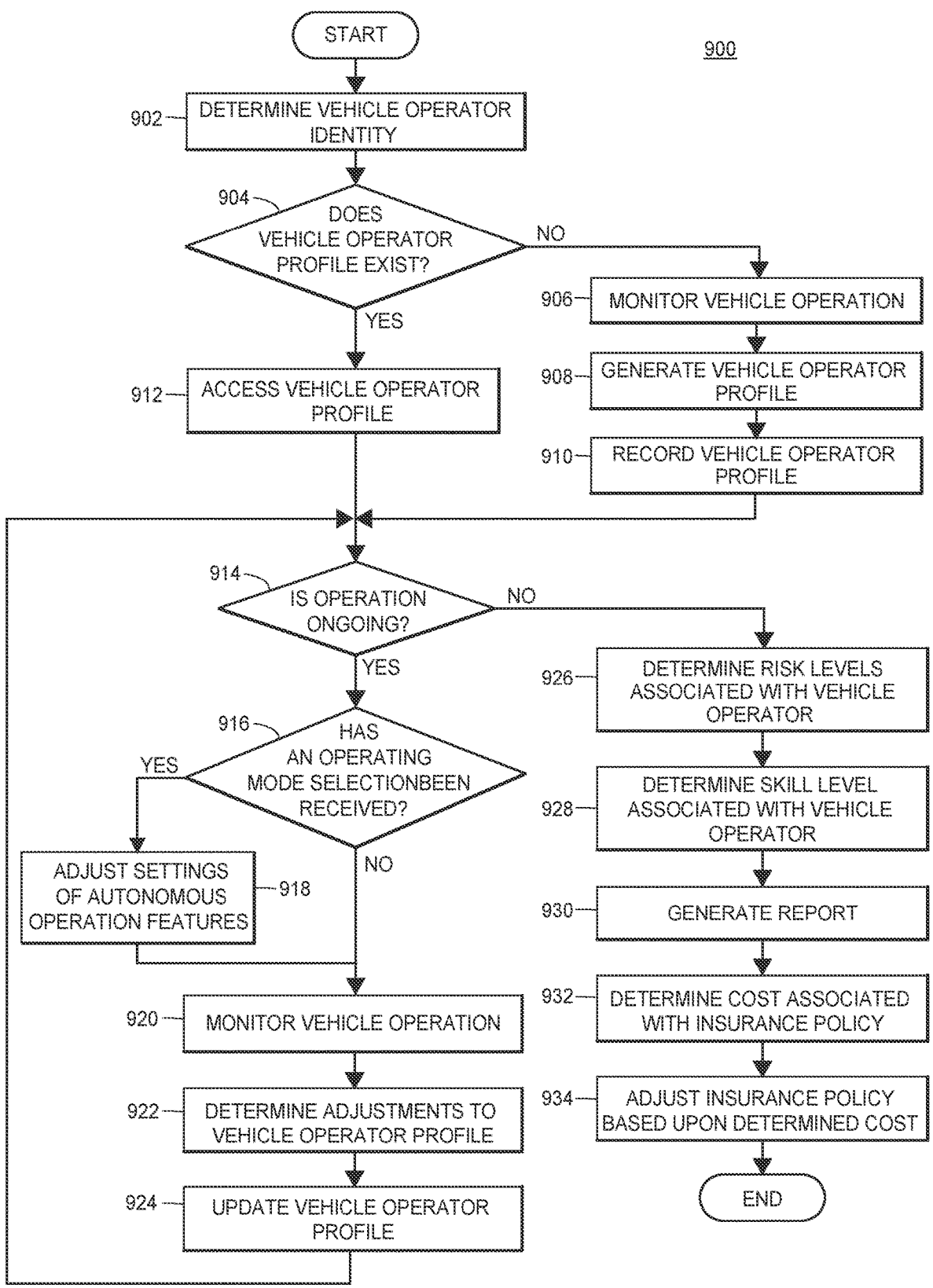
FIG. 9 illustrates a flow diagram depicting an exemplary vehicle operator use monitoring and evaluation method in accordance with the presently described embodiments.

FIG. 9 illustrates a flow diagram depicting an exemplary vehicle operator use monitoring and evaluation method 900 that may be used to determine skill or risk levels associated with a vehicle operator or adjust an insurance policy. The exemplary method 900 may begin with determining the identity of the vehicle operator at block 902. If a vehicle operator profile can be found for the vehicle operator at block 904, the vehicle operator profile may be accessed at block 912. If no vehicle operator profile can be found for the vehicle operator at block 904, a vehicle operator profile may be created based upon vehicle operations and stored for future use at blocks 906-910. The newly created vehicle operator profile may be generated at block 908 with vehicle operating data from only a short time period or may include only information regarding configuration and/or settings of the autonomous operation features, in which case operation of the vehicle may continue after the vehicle operator profile is generated. If operation is determined to be ongoing at block 914, vehicle operation may be monitored and the vehicle operator profile may be updated at blocks 916-924. In some embodiments, the vehicle operator may be able to select an option of a mode for vehicle operation. If such a mode selection is detected at block 916, the settings of the autonomous operation features may be adjusted at block 918. Vehicle operation may be monitored at block 920 based upon received operating data, which may be used to determine adjustments to the vehicle operator profile at block 922. The adjustments may then be used to update the vehicle operator profile at block 924. When operation is complete, the method 900 may determine risk or skill levels associated with the vehicle operator at blocks 926-928. These determined levels may be used at blocks 930-934 to generate a report or adjust an insurance policy. Although the exemplary embodiment is described as primarily performed by the on-board computer 114, the method 900 may be implemented by the mobile device 110, the on-board computer 114, the server 140, and/or a combination thereof.

The vehicle operator profile may include information regarding the vehicle operator, including an operating style of the vehicle operation. The operating style may include information regarding frequency with which the vehicle operator operates the vehicle manually, uses one or more autonomous operation features, selects one or more settings for the autonomous operation features, and/or takes control from the autonomous operation features under various conditions. The operating style may further include information regarding observed control decisions made by the vehicle operator, such as rate of acceleration, frequency of lane changes, use of vehicle signaling devices, distances maintained from other vehicles or pedestrians, and/or other aspects of vehicle operation. For example, vehicle operator decisions regarding how long to stop at a stop sign or when to begin accelerating from such a stop in the presence of other vehicles or pedestrians may be included in the operating style. The vehicle operator profile may further include information regarding vehicle operator skill levels, as described below. In some embodiments, the vehicle operator profile may include a risk profile or information regarding one or more risk levels associated with operation of the vehicle by the vehicle operator. Such risk levels may be associated with particular configurations or settings of autonomous operation features and/or particular conditions of the vehicle environment (e.g., time of day, traffic levels, weather, etc.).

In further embodiments, the vehicle operator profile may include information regarding attentiveness of the vehicle operator while the vehicle is being autonomously operated. For example, some vehicle operators may typically pay attention to road conditions while a vehicle is operating in a fully autonomous mode, while other vehicle operators may typically engage in other activities. In some embodiments, the vehicle operator profile may include information regarding decisions made by the vehicle operator regarding actions that would result in adjustments to costs associated with an insurance policy (e.g., accepting or rejecting recommendations to optimize autonomous operation feature use to lower insurance costs).

The vehicle operator profile or vehicle operator behavior data may indicate how well the specific vehicle operator drives in rain, snow, sleet, ice, heavy traffic, road construction, stop-and-go traffic, bumper-to-bumper traffic, country or rural traffic, and/or city or downtown street traffic. The current environment (or condition) may include or be rain, ice, snow, fog, heavy traffic, bumper-to-bumper traffic, road construction, city traffic, country or rural traffic, and/or may be associated with a type of road, such as a two-lane or four-lane highway, and/or downtown city street or other street having several traffic lights.

The operating mode may include one or more settings or configurations of autonomous operation features. For example, operating modes may include adjustments to settings that cause the autonomous operation features to control the vehicle 108 in a more or less aggressive manner with respect to speed, distance from other vehicles, distance from pedestrians, etc. As an example, the settings may cause the vehicle 108 to remain at least a minimum distance from other vehicles (which may depend upon vehicle speed or road conditions), and/or modes may set different minimum distances. Examples of modes may include a city driving mode, a highway driving mode, a rush operation mode, a smooth operation mode, a cautious mode, and/or a user-defined mode.

In some embodiments, an operating mode may be based upon the vehicle operator profile. For example, the vehicle profile may include information indicating an operating style of the vehicle operator based upon observations of control commands by the vehicle operator, which profile information may be used to generate an operation mode that mimics the style of the vehicle operator. Thus, if the vehicle operator typically stops at stop signs for a particular length of time, the operating style may mimic this length of time to provide an experience that seems normal or customary to the vehicle operator.

Exemplary Methods for Comparing Costs

Figure 10:
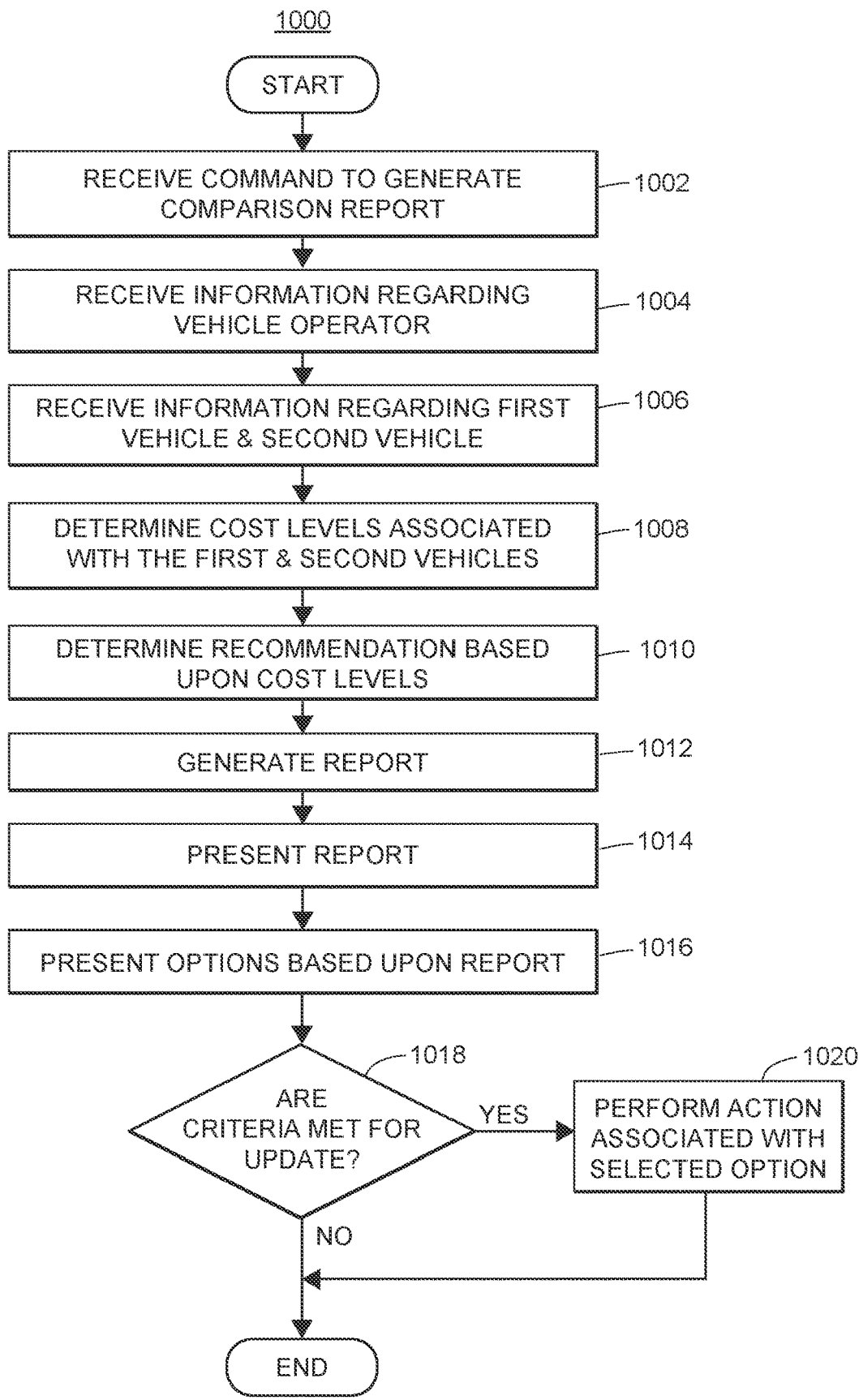
FIG. 10 illustrates a flow diagram depicting an exemplary cost comparison method in accordance with the presently described embodiments.

FIG. 10 illustrates a flow diagram depicting an exemplary cost comparison method 1000 that may be used to compare costs associated with vehicles, some of which may include autonomous operation features. The exemplary method 1000 may begin by receiving a command to generate a comparison report between two or more alternative transportation options for an insurance customer or other user. The method 1000 may further receive information regarding one or more vehicle operators may be received at block 1004 and/or information regarding a first vehicle and a second vehicle at block 1006. The first and second vehicles may differ in autonomous operation features or other characteristics. Cost levels associated with obtaining, operating, and insuring the first vehicle and the second vehicle may be determined at block 1008, and/or a recommendation based upon the costs may be determined at block 1010. A report including the costs levels, recommendation, and/or related information may be generated at block 1012 and presented to the insurance customer or other user at block 1014. Additionally, one or more options may be presented along with the report at block 1016, such as options to perform another comparison or present additional information. If an option is selected at block 1018, the corresponding action may be performed at block 1020. Although the exemplary embodiment is described as primarily performed by the server 140, the method 1000 may be implemented by the mobile device 110, the on-board computer 114, the server 140, and/or a combination thereof.

Exemplary Methods for Updating Autonomous Operation Features

Figure 11:
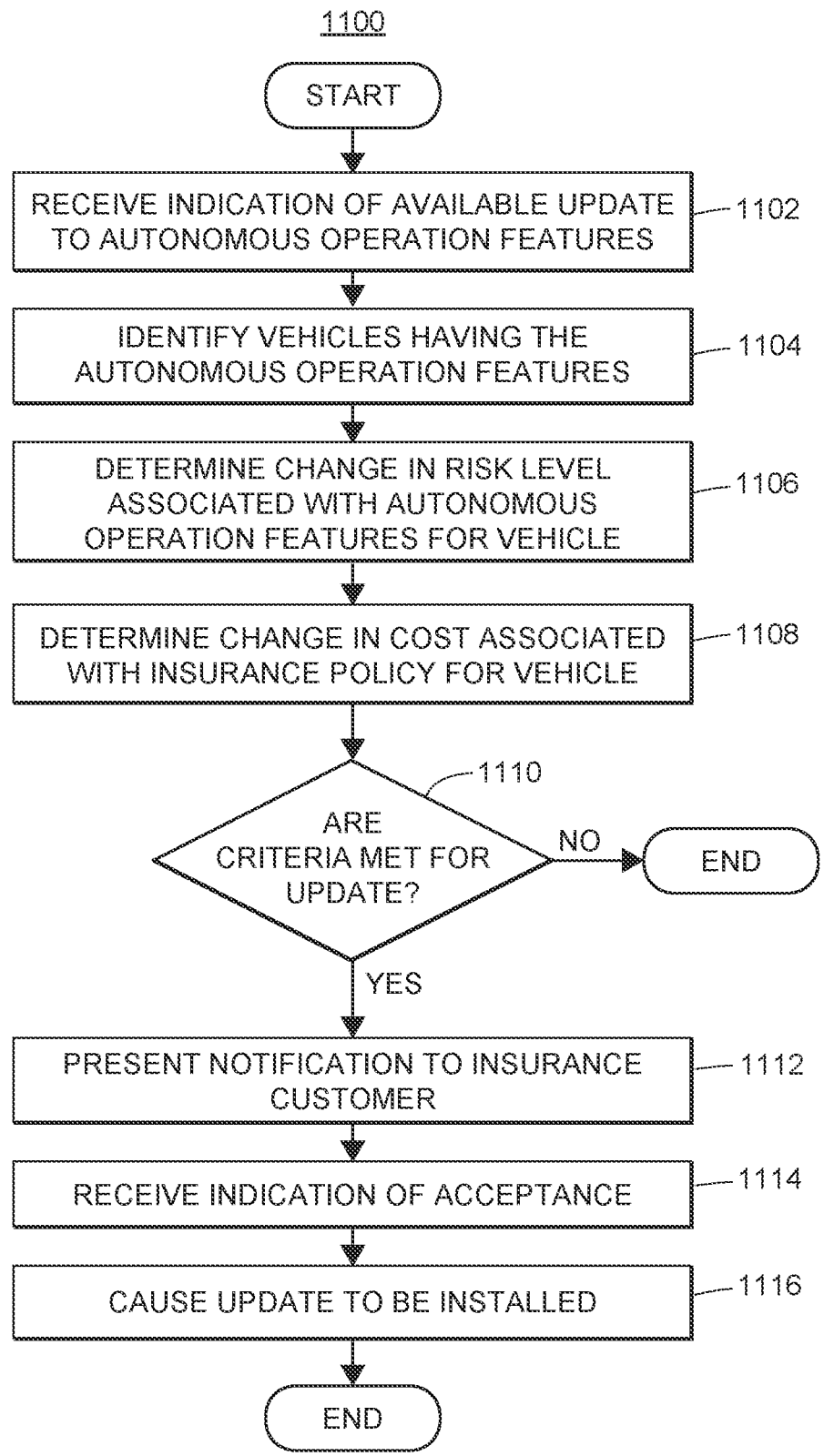
FIG. 11 illustrates a flow diagram depicting an exemplary autonomous operation feature update method in accordance with the presently described embodiments.

FIG. 11 illustrates a flow diagram depicting an exemplary autonomous operation feature update method 1100 that may be used to identify, recommend, and/or install updates to autonomous operation features in appropriate autonomous or semi-autonomous vehicles. In some embodiments, the updates may include software version updates. The exemplary method 1100 may begin with the receipt of an indication of an available update to an autonomous operation feature at block 1102, which may include an update to a version of autonomous operation feature software. A plurality of vehicles having the autonomous operation feature may be identified at block 1104 based upon recorded features or communication with the plurality of vehicles. A change in one or more risk levels associated with the update may be determined for some or all of the identified vehicles at block 1106, and/or a change in a cost associated with one or more of the plurality of vehicles may be determined at block 1108. If the determined changes in risk levels or insurance costs meet certain criteria for installing the update at block 1110, a notification regarding the update may be presented to an insurance customer at block 1112. The notification may further include information regarding costs associated with the update. If an indication of acceptance of the update is received at block 1114, the update may be installed at block 1116. Although the exemplary embodiment is described as primarily performed by the server 140, the method 1100 may be implemented by the mobile device 110, the on-board computer 114, the server 140, and/or a combination thereof.

Exemplary Methods for Repair of an Autonomous Vehicle

Figure 12:
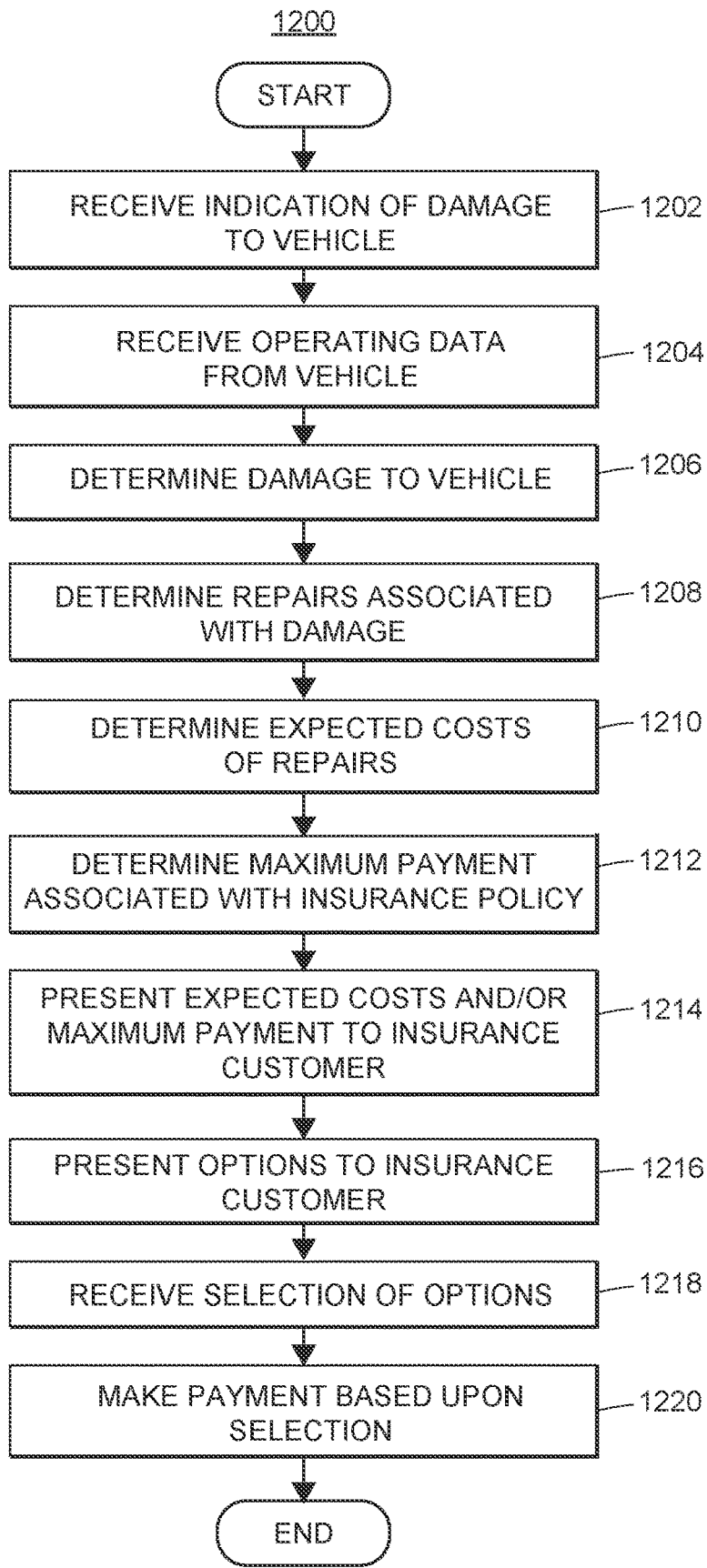
FIG. 12 illustrates a flow diagram depicting an exemplary autonomous vehicle repair method in accordance with the presently described embodiments.

FIG. 12 illustrates a flow diagram depicting an exemplary autonomous vehicle repair method 1200 that may be used to determine repairs needed as a result of damage to an autonomous or semi-autonomous vehicle. The exemplary method 1200 may begin by receiving an indication of damage to the vehicle 108 at block 1202 and/or receiving operating data associated with the vehicle 108 at block 1204. Based upon the operating data, the type and extent of damage to the vehicle 108 may be determined at block 1206, and/or repairs needed to fix the damage may be determined at block 1208. Additionally, one or more expected costs (or ranges of costs) for the repairs may be estimated at block 1210. An insurance policy associated with the vehicle 108 may be identified, and/or a maximum payment for the repairs may be determined at block 1212 based upon the estimated costs and the insurance policy. Information regarding the estimated cost or costs and the maximum payment under the insurance policy may be presented to an insurance customer at block 1214. Additionally, options associated with the repairs may be presented to the insurance customer at block 1216, and/or a selection of one or more options may be received at block 1218. An insurer or other party may cause a payment to be made at block 1220 to the insurance customer, beneficiary, or other relevant party based upon the estimated costs of repairing the damage and the selected option. Although the exemplary embodiment is described as primarily performed by the server 140, the method 1200 may be implemented by the mobile device 110, the on-board computer 114, the server 140, and/or a combination thereof.

Exemplary Methods for Infrastructure Communications

Figure 13:
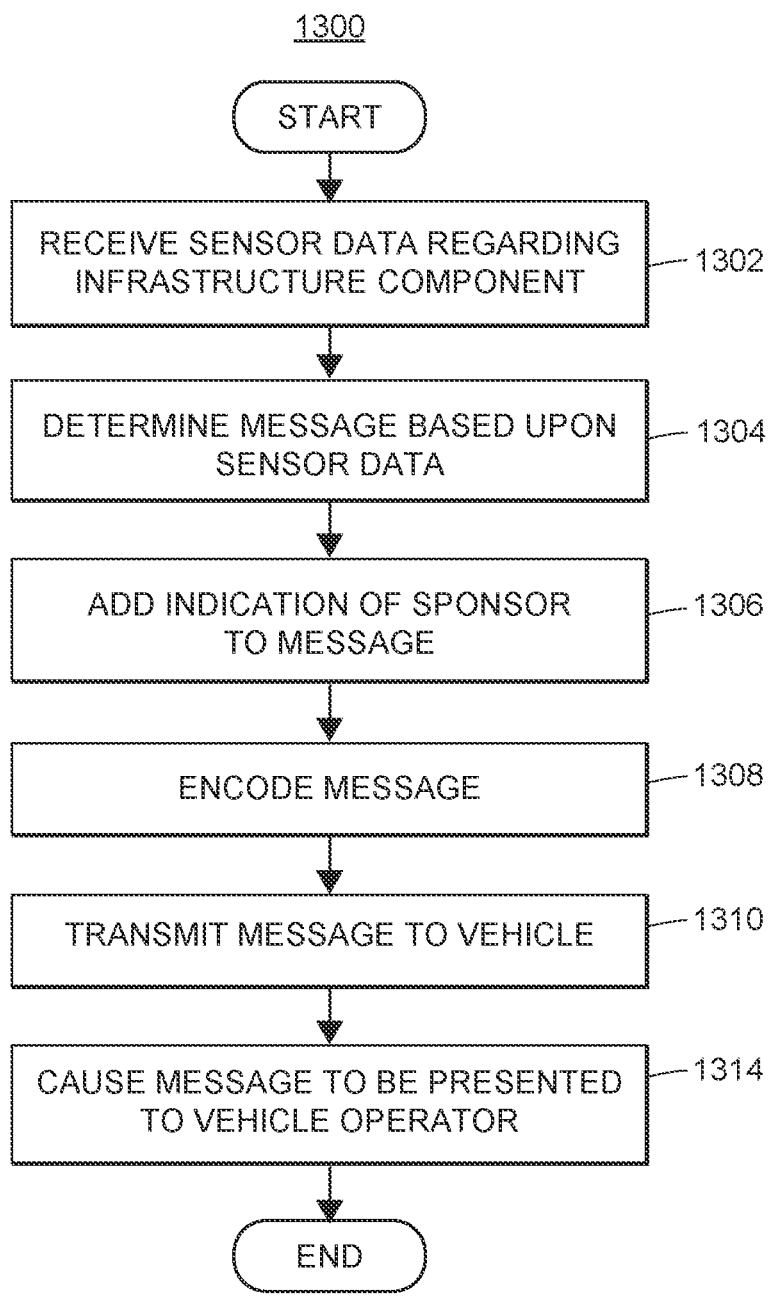
FIG. 13 illustrates a flow diagram depicting an exemplary infrastructure communication method in accordance with the presently described embodiments.

FIG. 13 illustrates a flow diagram depicting an exemplary infrastructure communication method 1300 that may be used to detect and communicate information regarding infrastructure components to vehicles. The exemplary method 1300 may begin with the infrastructure communication device 124 receiving information regarding the infrastructure component 126 from one or more sensors at block 1302. The information may be used at block 1304 to determine a message regarding the infrastructure component 126. In some embodiments, the message may be augmented at block 1306 by information associated with a sponsor or other party affiliated with the infrastructure communication device 124. The message may then be encoded at block 1308 and transmitted at block 1310, which may cause the message to be presented to the vehicle operator of the vehicle 108 at block 1312. Although the exemplary embodiment describes one infrastructure communication device 124 communicating with one vehicle 108, it should be understood than any number of infrastructure communication devices 124 may communicate with any number of vehicles 108.

Updating Insurance Policies

In one aspect, a computer-implemented method of updating an insurance policy may be provided. The method may include (a) gathering or receiving, at or via one or more processors (such as either a local processor associated with a smart vehicle and/or a remote processor or server associated with an insurance provider), data indicative of (1) vehicle usage, and/or (2) vehicle drivers for an insured vehicle; (b) analyzing the data, via the one or more processors, to determine (i) an amount and/or (ii) type of vehicle usage for each vehicle driver; (c) based upon the amount of vehicle usage for each vehicle driver and/or the type of vehicle usage for each vehicle driver, via the one or more processors, updating or adjusting an insurance policy (such as a premium, rate, rewards or points program, discount, etc.) for the insured vehicle; (d) transmitting, under the direction or control of the one or more processors, the updated or adjusted insurance policy (or otherwise causing the updated or adjusted insurance policy to be presented or displayed to the insured) to a mobile device of the insured for their review, modification, and/or approval; and/or (e) receiving, at or via the one or more processors, from the mobile device of the insured (such as via wireless communication) an approval of the updated or adjusted insurance policy of the insured to facilitate more accurate insurance pricing and/or insurance cost savings. The method may include additional, fewer, or alternate actions, including those discussed elsewhere herein.

For instance, the amount of vehicle usage may include an amount of time and/or miles that each individual vehicle driver drives the vehicle. The type of vehicle usage may include characterizing various periods of driving and/or trips as city driving; country driving; freeway or highway driving city street driving; heavy traffic or congested traffic driving; driving in good weather; driving in hazardous weather; rush hour driving; and/or time-of-day driving.

The vehicle drivers may be identified from mobile device signature; seat pressure sensors and weight; image recognition techniques performed upon images of the driver; and/or biometric devices (such as heart beat or rate characteristics; voice print; and/or thumb or finger prints).

Biometric Device Data

In one aspect, a computer-implemented method of updating an insurance policy using biometric device data may be provided. The method may include (a) gathering or receiving, at or via one or more processors (such as either a local processor associated with a smart vehicle and/or a remote processor or server associated with an insurance provider), data from a biometric device indicative of whom is driving an insured vehicle; (b) gathering or receiving, at or via the one or more processors, data indicative of vehicle usage for a single trip and/or driving or driver behavior during the single trip; (c) updating or adjusting, at or via the one or more processors, an insurance policy (such as a premium, rate, rewards or points program, discount, etc.) for the insured vehicle based upon (1) whom is driving the insured vehicle (and/or his or her driving profile or score), and/or (2) the data indicative of vehicle usage for the single trip and/or the driving or driver behavior exhibited during the single trip to facilitate more accurate risk assessment and/or cost savings to the insured. The method may include additional, fewer, or alternate actions, including those discussed elsewhere herein. For instance, the biometric device may verify an identity of the driver based upon heartbeat, facial recognition techniques, and/or mood.

In another aspect, a computer-implemented method of updating an insurance policy may be provided. The method may include (1) gathering or receiving, at or via one or more processors (such as either a local processor associated with a smart vehicle and/or a remote processor or server associated with an insurance provider), data from a biometric device identifying a driver of an insured vehicle; (2) gathering or receiving, at or via the one or more processors, data indicative of driving or driver behavior for the driver identified from the biometric device data; (3) generating, at or via the one or more processors, a usage-based insurance policy for the insured vehicle based upon (i) the identity of the driver determined from the biometric device data, and/or (ii) the data indicative of driving or driver behavior exhibited by the driver to facilitate more accurate risk assessment and/or provide cost savings to the insured. The method may include additional, fewer, or alternate actions, including those discussed elsewhere herein.

Software Versions

In one aspect, a computer-implemented method of updating an insurance policy may be provided. The method may include (1) gathering or receiving, at or via one or more processors (such as either a local processor associated with a smart vehicle and/or a remote processor or server associated with an insurance provider), data indicative of a software version installed on or in an insured vehicle that is associated with an autonomous or semi-autonomous functionality; (2) determining, at or via the one or more processors, that the software version is out of date or a (safer or less risky) new software version exists and/or is available for download; (3) generating, at or via the one or more processors, a recommendation to an insured to update or upgrade to the new software version, and transmitting that recommendation under the direction or control of the one or more processors to a mobile device or insured vehicle controller (such as via wireless communication or data transmission); (4) determining, at or via the one or more processors, (or receiving an indication) that the insured has updated or upgraded to the new software version associated with the autonomous or semi-autonomous functionality; and/or (5) updating or adjusting, at or via the one or more processors, an insurance policy (such as a premium, rate, rewards or points program, discount, etc.) for the insured vehicle based upon the insured updating or upgrading to the new software version associated with an autonomous or semi-autonomous functionality to facilitate providing cost savings to the insured and/or enticing drivers to update vehicle software to most recent versions and/or versions that perform better. The method may include additional, fewer, or alternate actions, including those discussed elsewhere herein.

Exemplary Autonomous Vehicle Insurance Risk and Price Determination Methods

Risk profiles or risk levels associated with one or more autonomous operation features determined above may be further used to determine risk categories or premiums for vehicle insurance policies covering autonomous vehicles. In some embodiments or under some conditions, the vehicle 108 may be a fully autonomous vehicle operating without a vehicle operator's input or presence. In other embodiments or under other conditions, the vehicle operator may control the vehicle 108 with or without the assistance of the vehicle's autonomous operation features. For example, the vehicle may be fully autonomous only above a minimum speed threshold or may require the vehicle operator to control the vehicle during periods of heavy precipitation. Alternatively, the autonomous vehicle may perform all relevant control functions using the autonomous operation features under all ordinary operating conditions. In still further embodiments, the vehicle 108 may operate in either a fully or a partially autonomous state, while receiving or transmitting autonomous communications.

Where the vehicle 108 operates only under fully autonomous control by the autonomous operation features under ordinary operating conditions or where control by a vehicle operator may be disregarded for insurance risk and price determination, the risk level or premium associated with an insurance policy covering the autonomous vehicle may be determined based upon the risks associated with the autonomous operation features, without reference to risks associated with the vehicle operator. Where the vehicle 108 may be operated manually under some conditions, the risk level or premium associated with an insurance policy covering the autonomous vehicle may be based upon risks associated with both the autonomous operation features and the vehicle operator performing manual vehicle operation. Where the vehicle 108 may be operated with the assistance of autonomous communications features, the risk level or premium associated with an insurance policy covering the autonomous vehicle may be determined based in part upon a determination of the expected use of autonomous communication features by external sources in the relevant environment of the vehicle 108 during operation of the vehicle 108.

Data Acquisition

In one aspect, the present embodiments may relate to data acquisition. Data may be gathered via devices employing wireless communication technology, such as Bluetooth or other IEEE communication standards. In one embodiment, a Bluetooth enabled smartphone or mobile device, and/or an in-dash smart and/or communications device may collect data. The data associated with the vehicle, and/or vehicle or driver performance, that is gathered or collected at, or on, the vehicle may be wirelessly transmitted to a remote processor or server, such as a remote processor or server associated with an insurance provider. The mobile device 110 may receive the data from the on-board computer 114 or the sensors 120, and may transmit the received data to the server 140 via the network 130, and the data may be stored in the database 146. In some embodiments, the transmitted data may include real-time sensor data, a summary of the sensor data, processed sensor data, operating data, environmental data, communication data, or a log such data.

Data may be generated by autonomous or semi-autonomous vehicles and/or vehicle mounted sensors (or smart sensors), and then collected by vehicle mounted equipment or processors, including Bluetooth devices, and/or an insurance provider remote processor or server. The data gathered may be used to analyze vehicle decision making. A processor may be configured to generate data on what an autonomous or semi-autonomous vehicle would have done in a given situation had the driver not taken over manual control/driving of the vehicle or alternative control actions not taken by the autonomous or semi-autonomous operation features. This type of control decision data (related to vehicle decision making) may be useful with respect to analyzing hypothetical situations.

In one embodiment, an application, or other computer or processor instructions, may interact with a vehicle to receive and/or retrieve data from autonomous or semi-autonomous processors and sensors. The data retrieved may be related to radar, cameras, sensor output, computer instructions or application output. Other data related to a smart vehicle controller, car navigation unit information (including route history information and typical routes taken), GPS unit information, odometer and/or speedometer information, and smart equipment data may also be gathered or collected. The application and/or other computer instructions may be associated with an insurance provider remote processor or server.

The control decision data may further include information regarding control decisions generated by one or more autonomous operation features within the vehicle. The operating data and control decision data gathered, collected, and/or acquired may facilitate remote evaluation and/or analysis of what the autonomous or semi-autonomous vehicle was "trying to do" (brake, slow, turn, accelerate, etc.) during operation, as well as what the vehicle actually did do. The data may reveal decisions, and the appropriateness thereof, made by the artificial intelligence or computer instructions associated with one or more autonomous or semi-autonomous vehicle technologies, functionalities, systems, and/or pieces of equipment. The data may include information related to what the vehicle would have done in a situation if the driver had not taken over (beginning manual vehicle control). Such data may include both the control actions taken by the vehicle and control actions the autonomous or semi-autonomous operation features would have caused the vehicle to take. Thus, in some embodiments, the control decisions data may include information regarding control decisions not implemented by the autonomous operation features to control the vehicle. This may occur when an autonomous operation feature generates a control decision or associated control signal, but the control decision or signal is prevented from controlling the vehicle because the autonomous feature or function is disabled, the control decision is overridden by the vehicle operator, the control signal would conflict with another control signal generated by another autonomous operation feature, a more preferred control decision is generated, and/or an error occurs in the on-board computer 114 or the control system of the vehicle.

For example, a vehicle operator may disable or constrain the operation of some or all autonomous operation features, such as where the vehicle is operated manually or semi-autonomously. The disabled or constrained autonomous operation features may however, continue to receive sensor data and generate control decision data that is not implemented. Similarly, one or more autonomous operation features may generate more than one control decision in a relevant period of time as alternative control decisions. Some of these alternative control decisions may not be selected by the autonomous operation feature or an autonomous operation control system to control the vehicle. For example, such alternative control decisions may be generated based upon different sets of sensor or communication data from different sensors 120 or include or excluding autonomous communication data. As another example, the alternative control decisions may be generated faster than they can be implemented by the control system of the vehicle, thus preventing all control decisions from being implemented.

In addition to control decision data, other information regarding the vehicle, the vehicle environment, or vehicle operation may be collected, generated, transmitted, received, requested, stored, and/or recorded in connection with the control decision data. Additional operating data including sensor data from the sensors 120, autonomous communication data from the communication component 122 or the communication unit 220, location data, environmental data, time data, settings data, configuration data, and/or other relevant data may be associated with the control decision data. In some embodiments, a database or log may store the control decision data and associated information. In further embodiments, the entries in such log or database may include a timestamp indicating the date, time, location, vehicle environment, vehicle condition, autonomous operation feature settings, and/or autonomous operation feature configuration information associated with each entry. Such data may facilitate evaluating the autonomous or semi-autonomous technology, functionality, system, and/or equipment in hypothetical situations and/or may be used to calculate risk, and in turn adjust insurance policies, premiums, discounts, etc.

Autonomous Vehicle Insurance Policies

The disclosure herein relates to insurance policies for vehicles with autonomous operation features. Accordingly, as used herein, the term "vehicle" may refer to any of a number of motorized transportation devices. A vehicle may be a car, truck, bus, train, boat, plane, motorcycle, snowmobile, other personal transport devices, etc. Also as used herein, an "autonomous operation feature" of a vehicle means a hardware or software component or system operating within the vehicle to control an aspect of vehicle operation without direct input from a vehicle operator once the autonomous operation feature is enabled or engaged. The term "autonomous vehicle" means a vehicle including at least one autonomous operation feature. A "fully autonomous vehicle" means a vehicle with one or more autonomous operation features capable of operating the vehicle in the absence of or without operating input from a vehicle operator.

Additionally, the term "insurance policy" or "vehicle insurance policy," as used herein, generally refers to a contract between an insurer and an insured. In exchange for payments from the insured, the insurer pays for damages to the insured which are caused by covered perils, acts, or events as specified by the language of the insurance policy. The payments from the insured are generally referred to as "premiums," and typically are paid by or on behalf of the insured upon purchase of the insurance policy or over time at periodic intervals. Although insurance policy premiums are typically associated with an insurance policy covering a specified period of time, they may likewise be associated with other measures of a duration of an insurance policy, such as a specified distance traveled or a specified number of trips. The amount of the damages payment is generally referred to as a "coverage amount" or a "face amount" of the insurance policy. An insurance policy may remain (or have a status or state of) "in-force" while premium payments are made during the term or length of coverage of the policy as indicated in the policy. An insurance policy may "lapse" (or have a status or state of "lapsed"), for example, when the parameters of the insurance policy have expired, when premium payments are not being paid, when a cash value of a policy falls below an amount specified in the policy, or if the insured or the insurer cancels the policy.

The terms "insurer," "insuring party," and "insurance provider" are used interchangeably herein to generally refer to a party or entity (e.g., a business or other organizational entity) that provides insurance products, e.g., by offering and issuing insurance policies. Typically, but not necessarily, an insurance provider may be an insurance company. The terms "insured," "insured party," "policyholder," and "customer" are used interchangeably herein to refer to a person, party, or entity (e.g., a business or other organizational entity) that is covered by the insurance policy, e.g., whose insured article or entity is covered by the policy. Typically, a person or customer (or an agent of the person or customer) of an insurance provider fills out an application for an insurance policy. In some cases, the data for an application may be automatically determined or already associated with a potential customer. The application may undergo underwriting to assess the eligibility of the party and/or desired insured article or entity to be covered by the insurance policy, and, in some cases, to determine any specific terms or conditions that are to be associated with the insurance policy, e.g., amount of the premium, riders or exclusions, waivers, and the like. Upon approval by underwriting, acceptance of the applicant to the terms or conditions, and payment of the initial premium, the insurance policy may be in-force, (i.e., the policyholder is enrolled).

Although the exemplary embodiments discussed herein relate to automobile insurance policies, it should be appreciated that an insurance provider may offer or provide one or more different types of insurance policies. Other types of insurance policies may include, for example, commercial automobile insurance, inland marine and mobile property insurance, ocean marine insurance, boat insurance, motorcycle insurance, farm vehicle insurance, aircraft or aviation insurance, and other types of insurance products.

Other Matters

Although the text herein sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

In one aspect, autonomous or semi-autonomous vehicle; telematics; interconnected home; mobile device; and/or other data, including that discussed elsewhere herein, may be collected or received by an insurance provider remote server, such as via direct or indirect wireless communication or data transmission, after a customer affirmatively consents or otherwise opts into an insurance discount, reward, or other program. The insurance provider may then analyze the data received with the customer's permission to provide benefits to the customer. As a result, risk averse customers may receive insurance discounts or other insurance cost savings based upon data that reflects low risk behavior and/or technology that mitigates or prevents risk to (i) insured assets, such as autonomous or semi-autonomous vehicles, and/or (ii) autonomous or semi-autonomous vehicle operators or passengers.

It should also be understood that, unless a term is expressly defined in this patent using the sentence "As used herein, the term '_' is hereby defined to mean . . . " or a similar sentence, there is no intent to limit the meaning of that term, either expressly or by implication, beyond its plain or ordinary meaning, and such term should not be interpreted to be limited in scope based upon any statement made in any section of this patent (other than the language of the claims). To the extent that any term recited in the claims at the end of this disclosure is referred to in this disclosure in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based upon the application of 35 U.S.C. § 112(f).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware is temporarily configured (e.g., programmed), the hardware need not be configured or instantiated at any one instance in time. Software may accordingly configure a processor, for example, to constitute a particular hardware module at one instance of time and to constitute a different hardware module at a different instance of time. Hardware elements can provide information to, and receive information from, other hardware elements. Accordingly, the described hardware may be regarded as being communicatively coupled.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may in some example embodiments, comprise processor-implemented modules. Similarly, the methods or routines described herein may be at least partially processor-implemented. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information. As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment. Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. In addition, use of the "a" or "an" are employed to describe elements and components of the embodiments herein. This is done merely for convenience and to give a general sense of the description. In this description, and the claims that follow, the singular also includes the plural unless it is obvious that it is meant otherwise. This detailed description is to be construed as exemplary only and does not describe every possible embodiment, as describing every possible embodiment would be impractical, if not impossible. One could implement numerous alternate embodiments, using either current technology or technology developed after the filing date of this application.

Upon reading this disclosure, those of skill in the art will appreciate still additional alternative structural and functional designs for system and a method for assigning mobile device data to a vehicle through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

What is claimed is:

1. A computer-implemented method for operating an autonomous or semi-autonomous vehicle, comprising, during operation of the vehicle:
    receiving, by a processor, operating data related to an autonomous operation feature of the vehicle, the operating data indicating a current operating environment of the vehicle;
    receiving, by the processor, a request to disable the autonomous operation feature;
    determining, by the processor and based on the operating data,
        a first risk level associated with operating the vehicle, in the current operating environment, under control of the autonomous operation feature, and
        a second risk level associated with operating the vehicle, in the current operating environment, under control of an operator;
    in response to the request, and based on the first risk level and the second risk level, determining, by the processor, whether to disable the autonomous operation feature; and
    causing, by the processor, a display carried by the vehicle to provide an output indicating whether to disable the autonomous operation feature.

2. The computer-implemented method of claim 1, further comprising:
    determining, by the processor, a preparedness level of the operator to assume control of the vehicle,
    wherein whether to disable the autonomous operation feature is determined based on the preparedness level of the operator.

3. The computer-implemented method of claim 1, further comprising:
    causing, by the processor and via the display, presentation of an option to override a determination to not disable the autonomous operation feature;
    receiving, by the processor and via the display, a selection of the option to override; and
    causing, by the processor and in response to the selection, to disable the autonomous operation feature.

4. The computer-implemented method of claim 3, the method further comprising:
    determining, by the processor, a third risk level associated with disabling the autonomous operation feature;
    determining, by the processor, that the third risk level does not satisfy a safety threshold; and causing, by the processor and based on the third risk level not satisfying the safety threshold, the autonomous operation feature to remain engaged.

5. The computer-implemented method of claim 3, wherein the output indicates that, the method further comprising:
determining, by the processor, that the selection is not received within a threshold amount of time from the presentation of the option to override; and
based on determining that the selection is not received within the threshold amount of time, causing, by the processor, the autonomous operation feature to remain engaged.

6. The computer-implemented method of claim 3, further comprising:
adjusting, by the processor and based on receiving the selection of the option to override, a value of a policy associated with the autonomous or semi-autonomous vehicle.

7. The computer-implemented method of claim 1, further comprising:
determining, by the processor, an identity of the operator; and
accessing, by the processor, an operator profile associated with the operator,
wherein the second risk level is determined based at least in part on information included in the operator profile.

8. The computer-implemented method of claim 7, wherein the second risk level is determined based on a setting of the autonomous operation feature, selected by the operator, and stored in the operator profile.

9. The computer-implemented method of claim 1, wherein the current operating environment of the vehicle includes one or more of: a traffic condition, a construction, a type of road, a geographical location, a time of day, or a weather condition.

10. The computer-implemented method of claim 9, wherein the current operating environment is determined based on at least one of sensor data received from one or more sensors carried by the vehicle, or information from an external data source.

11. The computer-implemented method of claim 1, wherein the request is received from a mobile device associated with the operator, and via a wireless communication network.

12. The computer-implemented method of claim 1, wherein the autonomous operation feature is related to one of:
steering;
accelerating;
braking;
monitoring blind spots;
presenting a collision warning;
adaptive cruise control;
parking;
driver alertness monitoring;
driver responsiveness monitoring;
pedestrian detection;
a back-up system;
a navigation system;
a positioning system;
a security system;
an anti-hacking measure;
a theft prevention system; or
remote vehicle location determination.

13. A system for operating an autonomous or semiautonomous vehicle, comprising:
a processor; and
computer-readable media storing instructions which, when executed by the processor, causes the processor to:
receive operating data related to an autonomous operation feature of the vehicle, the operating data indicating a current operating environment of the vehicle;
receive a request to disable the autonomous operation feature;
determine, based on the operating data,
a first risk level associated with operating the vehicle, in the current operating environment, under control of the autonomous operation feature, and
a second risk level associated with operating the vehicle, in the current operating environment, under control of an operator;
in response to the request, and based on the first risk level and the second risk level, determine whether to disable the autonomous operation feature; and
cause a display carried by the vehicle to provide an output indicating whether to disable the autonomous operation feature.

14. The system of claim 13, wherein the instructions, when executed, further cause the processor to:
cause, via the display, presentation of an option to override a determination to not disable the autonomous operation feature;
receive a selection of the option to override;
determine a third risk level associated with disabling the autonomous operation feature;
determine that the third risk level does not satisfy a safety threshold; and
cause, based on the third risk level not satisfying the safety threshold, the autonomous operation feature to remain engaged.

15. The system of claim 14, wherein the instructions, when executed, further cause the processor to:
adjust, based on receiving the selection of the option to override, a value of a policy associated with the autonomous or semi-autonomous vehicle.

16. The system of claim 13, wherein the instructions, when executed, further cause the processor to:
determine an identity of the operator; and
access an operator profile associated with the operator,
wherein the second risk level is determined based at least in part on information included in the operator profile.

17. The system of claim 13, wherein the current operating environment of the vehicle includes one or more of: a traffic condition, a construction, a type of road, a geographical location, a time of day, or a weather condition.

18. A non-transitory computer-readable medium storing instructions which, when executed by a processor causes the processor to:
receive operating data related to an autonomous operation feature of a vehicle, the operating data indicating a current operating environment of the vehicle;
receive a request to disable the autonomous operation feature;
determine, based on the operating data,
a first risk level associated with operating the vehicle, in the current operating environment, under control of the autonomous operation feature, and
a second risk level associated with operating the vehicle, in the current operating environment, under control of an operator;

in response to the request, and based on the first risk level and the second risk level, determine whether to disable the autonomous operation feature; and cause a display carried by the vehicle to provide an output indicating whether to disable the autonomous operation feature.

19. The non-transitory computer-readable medium of claim 18, wherein the instructions further cause the processor to:

cause, via the display, presentation of an option to override a determination to not disable the autonomous operation feature;

receive a selection of the option to override; and based on receiving the selection, adjust a value of a policy associated with the autonomous or semi-autonomous vehicle.

20. The non-transitory computer-readable medium of claim 18, wherein the instructions further cause the processor to:

determine an identity of the operator; and access an operator profile associated with the operator, wherein the second risk level is determined based at least in part on information included in the operator profile.

* * * * *